United States Patent
Holoshitz et al.

(10) Patent No.: US 7,208,154 B2
(45) Date of Patent: Apr. 24, 2007

(54) METHODS AND COMPOSITIONS FOR THE TREATMENT OF MHC-ASSOCIATED CONDITIONS

(75) Inventors: Joseph Holoshitz, Ann Arbor, MI (US); Song Ling, Ypsilanti, MI (US)

(73) Assignee: Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 10/845,407

(22) Filed: May 13, 2004

(65) Prior Publication Data

US 2005/0013820 A1 Jan. 20, 2005

Related U.S. Application Data

(63) Continuation-in-part of application No. 10/161,959, filed on Jun. 3, 2002, now abandoned.

(51) Int. Cl.
*A61K 38/04* (2006.01)
(52) U.S. Cl. .................. 424/178.1; 514/2; 530/330
(58) Field of Classification Search ..................... None
See application file for complete search history.

(56) References Cited

U.S. PATENT DOCUMENTS

2002/0045230 A1* 4/2002 Rosen et al. ............... 435/183

OTHER PUBLICATIONS

Perdriger et al., 1997, J Rheumatol., vol. 24, pp. 1272-1276.*
Hossain et al., Neuroscience Res., 2000, vol. 36, pp. 285-290.*
Auger I et al. Nature Med 2:306-310 (1996).
Harris ED. N. Engl J Med 322:1277-1289 (1990).
Galena E and Feinstein DL. FASEB J 13:2125-2137 (1999).
Denninger JW and Marletta MA. Biochim Biophys Acta 1411:334-350 (1999).
Nepom GT et al. Arthritis Rheum 32:15-21 (1989).
Gregersen PK et al. Arthritis Rheum 30:1205-1213 (1987).
Brown KA. Br J Rheumatol 27: 150-155, (1988).
Maurice MM et al. J Immunol 158: 1458-1465, (1997).
Cemerski S et al. J Biol Chem 277: 19585-19593, (2002).
Cemerski S et al. Eur J Immunol 33: 2178-2185, (2003).
Yamanishi Y et al. Proc Natl Acad Sci (USA) 99: 10025-10030, (2002).
Migita K et al. Immunology 103: 362-367, (2001).
Ueki Y et al. J Rheumatol 23: 230-236, (1996).
Rall LC et al. J Nutr Biochem 11: 581-584, (2000).
Jikimoto T et al. Mol Immunol 38: 765-772, (2001).
Gonzalez-Escribano MF et al. Hum Immunol 60: 1259-1265 (1999).
Valenzuela A et al. Hum Immunol 60:250-254 (1999).
Jenkinson et al. Br J Rheumatol 28:86-88 (1989).
Aisen PS et al. J Neurol Sci 161:66-69 (1998).
Basu et al., Immunity 14:303-313 (2001).
Cunningham et al., Exp Neurol 163: 457-468 (2000).
Colaco CB et al. Clin Exp Immunol 72:15-19 (1988).
Taneja V et al. Arthritis Res. 2, 205-207, (2000).
Holmdahl R. et al. Ageing Res Rev. 1, 135-147, (2002).
Holoshitz J et al. Science 219, 56-58, (1983).
Kyburz D and Corr M et al. Springer Semin Immunopathol, 25: 79-90 (2003).
Zamani et al., Am J Med genet 76: 183-194, 1998.
Seigel JM. Narcolepsy: A key role for hypocretins (orexins). Cell 98: 409-412, 1999.
Sánchez et al., J Autoimmunity 15: 441-449, 2000.
Misko et al., Anal Biochem 214: 11-16, 1993.
Sakaguchi N et al. Nature. 426: 454-460, (2003).
Allen M. Miles, Yan Chen, Michael W. Owens, and Matthew B Grisham. Fluorometric Determination of Nitric Oxide. Methods, 7, 40-47, 1995.
Baksh S, Burns K, Busaa J, and Michalak M. Expression and purification of recombinant and native calreticulin. Protein Expr Purif., 3, 322-331, 1992.
Chemelli RM et al. Narcolepsy in orexin knockout mice: Molecular genetics of sleep regulation. Cell 98: 437-451, 1999.
Dorak et al., Int J Cancer 65:134-139 (1996).
Harris G et al. Radiosensitivity of peripheral blood lymphocytes in autoimmune disease. Int J Radiat Biol Relat Stud Phys Chem Med 47:689-699, 1985.
Henson PM, Bratton DL and Fadok V. The phosphatidylserine receptor: a crucial molecular switch? Nat Rev Mol Cell Biol 2: 627-633, 2001.
Johnsson et al., J Mol Recognit., 8, 125-131, 1995.
Karlsson et al., J. Immunol. Methods, 200, 121-133. 1997.
Löfås et al.,. Biosensors & Bioelectronics, 10, 813-822, 1995.
Lysiak et al., J Biol Chem 270: 21919-21927, 1995.
Lin L, et al. Cell 98: 365-376, 1999.
Miles AM, Chen Y, Owens MW, and Grisham MB. Fluorometric determination of nitric oxide. Methods 7: 40-47, 1995.

* cited by examiner

*Primary Examiner*—Gary B. Nickel
*Assistant Examiner*—Xiaozhen Xie
(74) *Attorney, Agent, or Firm*—Medlen & Carroll, LLP

(57) ABSTRACT

The present invention relates to methods and compositions for counteracting and reversing disease-causing signaling defects in disorders with underlying signal transduction aberrations, including but not limited to rheumatoid arthritis.

7 Claims, 25 Drawing Sheets

| | | |
|---|---|---|
| HLA-DRβ*0401 | $X_nQKRAAX_n$ | $Xaa_n$ Gln Lys Arg Ala Ala$Xaa_n$ [SEQ ID NO:28] [SEQ ID NO:35] |
| *0402 | $X_nDERAAX_n$ | $Xaa_n$ Asp Glu Arg Ala Ala$Xaa_n$ [SEQ ID NO:29] [SEQ ID NO:36] |
| *0403 | $X_nQRRAEX_n$ | $Xaa_n$ Gln Arg Arg Ala Glu$Xaa_n$ [SEQ ID NO:30] |
| *0404 | $X_nQRRAAX_n$ | $Xaa_n$ Gln Arg Arg Ala Ala$Xaa_n$ [SEQ ID NO:31] |
| H. Laminin β2 | $X_nQRRAAX_n$ | $Xaa_n$ Gln Arg Arg Ala Ala$Xaa_n$ [SEQ ID NO:31] |
| M. Laminin β2 | $X_nQRRTAX_n$ | $Xaa_n$ Gln Arg Arg Thr Ala$Xaa_n$ [SEQ ID NO:32] |
| APLP1 | $X_nQRRAAX_n$ | $Xaa_n$ Gln Arg Arg Ala Ala$Xaa_n$ [SEQ ID NO:31] |
| ApoE ε4 | $X_nQKRLAX_n$ | $Xaa_n$ Gln Lys Arg Leu Ala$Xaa_n$ [SEQ ID NO:33] |
| ε3 | $X_nQKRLAX_n$ | $Xaa_n$ Gln Lys Arg Leu Ala$Xaa_n$ [SEQ ID NO:33] |
| ε2 | $X_nQKCLAX_n$ | $Xaa_n$ Gln Lys Cys Leu Ala$Xaa_n$ [SEQ ID NO:34] |

FIG. 7

HBc*0401 [SEQ ID NO:17]

MDIDPYKEFGATVELLSFLPSDFFPSVRDLLDNASALYREALESPEHCSPHHTALRQAILCWGELMTLATWVGGNLED
HKDLLEQKRAAVDTYCVDPISRDLVVSYVNTNMGLKFRQLLWFHISCLTFGRETVIEYLVSFGVWIRTPPAYRPPNAP
ILSTLPAWARVIN

Met Asp Ile Asp Pro Tyr Lys Glu Phe Gly Ala Thr Val Glu Leu Leu Ser Phe Leu Pro
Ser Asp Phe Phe Pro Ser Val Arg Asp Leu Leu Asp Asn Ala Ser Ala Leu Tyr Arg Glu
Ala Leu Glu Ser Pro Glu His Cys Ser Pro His His Thr Ala Leu Arg Gln Ala Ile Leu
Cys Trp Gly Glu Leu Met Thr Leu Ala Thr Trp Val Gly Gly Asn Leu Glu Asp His Lys
Asp Leu Leu Glu Gln Lys Arg Ala Ala Val Asp Thr Tyr Cys Val Asp Pro Ile Ser Arg
Asp Leu Val Val Ser Tyr Val Asn Thr Asn Met Gly Leu Lys Phe Arg Gln Leu Leu Trp
Phe His Ile Ser Cys Leu Thr Phe Gly Arg Glu Thr Val Ile Glu Tyr Leu Val Ser Phe
Gly Val Trp Ile Arg Thr Pro Pro Ala Tyr Arg Pro Pro Asn Ala Pro Ile Leu Ser Thr
Leu Pro Ala Trp Ala Arg Val Ile Asn

FIG. 11 A

HBc*0402 [SEQ ID NO:18]

MDIDPYKEFGATVELLSFLPSDFFPSVRDLLDNASALYREALESPEHCSPHHTALRQAILCWGELMTLATWVGGNLED
HKDILEDERAAVDTYCVDPISRDLVVSYVNTNMGLKFRQLLWFHISCLTFGRETVIEYLVSFGVWIRTPPAYRPPNAP
ILSTLPAWARVIN

Met Asp Ile Asp Pro Tyr Lys Glu Phe Gly Ala Thr Val Glu Leu Leu Ser Phe Leu Pro
Ser Asp Phe Phe Pro Ser Val Arg Asp Leu Leu Asp Asn Ala Ser Ala Leu Tyr Arg Glu
Ala Leu Glu Ser Pro Glu His Cys Ser Pro His His Thr Ala Leu Arg Gln Ala Ile Leu
Cys Trp Gly Glu Leu Met Thr Leu Ala Thr Trp Val Gly Gly Asn Leu Glu Asp His Lys
Asp Ile Leu Glu Asp Glu Arg Ala Ala Val Asp Thr Tyr Cys Val Asp Pro Ile Ser Arg
Asp Leu Val Val Ser Tyr Val Asn Thr Asn Met Gly Leu Lys Phe Arg Gln Leu Leu Trp
Phe His Ile Ser Cys Leu Thr Phe Gly Arg Glu Thr Val Ile Glu Tyr Leu Val Ser Phe
Gly Val Trp Ile Arg Thr Pro Pro Ala Tyr Arg Pro Pro Asn Ala Pro Ile Leu Ser Thr
Leu Pro Ala Trp Ala Arg Val Ile Asn

FIG. 11 A Cont.

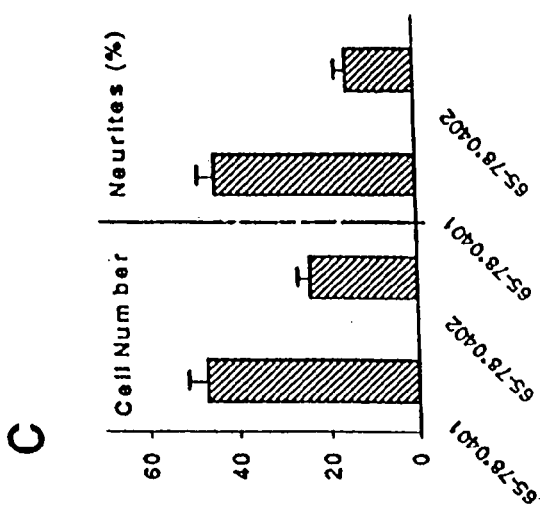
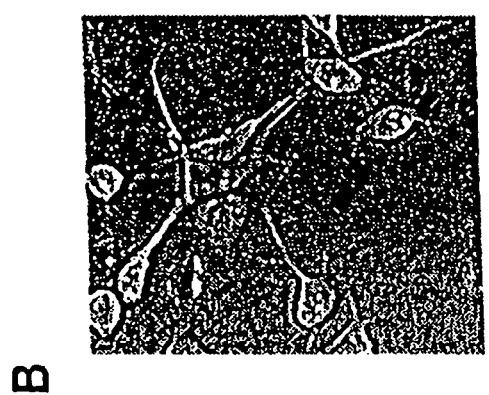
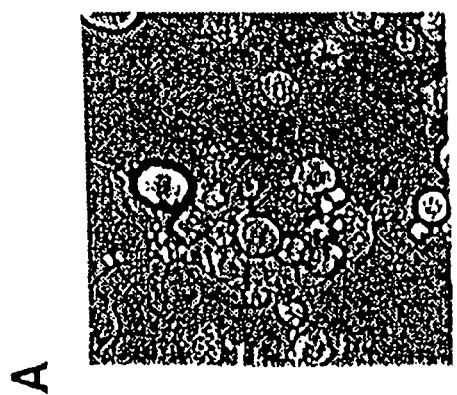
FIG. 12

```
  1 mllsvplllg llglavaepa vyfkeqfldg dgwtsrwies khksdfgkfv lssgkfygde
 61 ekdkglqtsq darfyalsas fepfsnkgqt lvvqftvkhe qmidcgggyv klfpnsldqt
121 dmhgdseyni mfgpdicgpg tkkvhvifny kgknvlinkd irckddefth lytlivrpdn
181 tyevkidnsq vesgsleddw dflppkkikd pdaskpedwd erakiddptd skpedwdkpe
241 hipdpdakkp edwdeemdge weppviqnpe ykgewkprqi dnpdykgtwi hpeidnpeys
301 pdpsiyaydn fgvlgldlwq vksgtifdnf litndeayae efgnetwgvt kaaekqmkdk
361 qdeeqrlkee eedkkrkeee eaedkedded kdedeedeed keedeeedvp gqakdel
```

FIG. 14

SEQUENCE LISTING

```
<160> NUMBER OF SEQ ID NOS: 38

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Gln Lys Arg Ala Ala
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic

<400> SEQUENCE: 2

Gln Arg Arg Ala Ala
1               5

<210> SEQ ID NO 3
<211> LENGTH: 5
<212> TYPE: PRT
<213> ORGANISM: Escherichia coli
<220> FEATURE:
<221> NAME/KEY: MISC_FEATURE
<222> LOCATION: (2)..(2)
<223> OTHER INFORMATION: The residue at this position can be lysine or
      arginine.
<220> FEATURE:
<221> NAME/KEY: MISC_FEATURE
<222> LOCATION: (3)..(4)
<223> OTHER INFORMATION: The residues at these positions can be any
      amino acid.

<400> SEQUENCE: 3

Gln Xaa Xaa Xaa Ala
1               5

<210> SEQ ID NO 4
<211> LENGTH: 5
<212> TYPE: PRT
<213> ORGANISM: Escherichia coli
<220> FEATURE:
<221> NAME/KEY: MISC_FEATURE
<222> LOCATION: (3)..(4)
<223> OTHER INFORMATION: The residues at these positions can be any
      amino acid.

<400> SEQUENCE: 4
```

Gln His Xaa Xaa Ala
1               5

<210> SEQ ID NO 5
<211> LENGTH: 15
<212> TYPE: PRT
<213> ORGANISM: Artificial Sequence
<220> FEATURE:
<223> OTHER INFORMATION: Synthetic

<400> SEQUENCE: 5

Lys Asp Leu Leu Glu Gln Lys Arg Ala Ala Val Asp Thr Tyr Cys
1               5                   10                  15

<210> SEQ ID NO 6
<211> LENGTH: 14
<212> TYPE: PRT
<213> ORGANISM: Artificial Sequence
<220> FEATURE:
<223> OTHER INFORMATION: Synthetic

<400> SEQUENCE: 6

Lys Asp Leu Leu Glu Gln Lys Arg Ala Ala Val Asp Thr Tyr
1               5                   10

<210> SEQ ID NO 7
<211> LENGTH: 15
<212> TYPE: PRT
<213> ORGANISM: Artificial Sequence
<220> FEATURE:
<223> OTHER INFORMATION: Synthetic

<400> SEQUENCE: 7

Lys Asp Ile Leu Glu Asp Glu Arg Ala Ala Val Asp Thr Tyr Cys
1               5                   10                  15

<210> SEQ ID NO 8
<211> LENGTH: 14
<212> TYPE: PRT
<213> ORGANISM: Artificial Sequence
<220> FEATURE:
<223> OTHER INFORMATION: Synthetic

<400> SEQUENCE: 8

Lys Asp Ile Leu Glu Asp Glu Arg Ala Ala Val Asp Thr Tyr
1               5                   10

<210> SEQ ID NO 9
<211> LENGTH: 15
<212> TYPE: PRT
<213> ORGANISM: Artificial Sequence
<220> FEATURE:
<223> OTHER INFORMATION: Synthetic

<400> SEQUENCE: 9

Lys Asp Leu Leu Glu Gln Arg Arg Ala Glu Val Asp Thr Tyr Cys
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic

<400> SEQUENCE: 10

Lys Asp Leu Leu Glu Gln Arg Arg Ala Ala Val Asp Thr Tyr Cys

```
<210> SEQ ID NO 11
<211> LENGTH: 5
<212> TYPE: PRT
<213> ORGANISM: Artificial Sequence
<220> FEATURE:
<223> OTHER INFORMATION: Synthetic

<400> SEQUENCE: 11

Gln Lys Arg Leu Ala
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic

<400> SEQUENCE: 12

Gln Lys Cys Leu Ala
1               5

<210> SEQ ID NO 13
<211> LENGTH: 5
<212> TYPE: PRT
<213> ORGANISM: Escherichia coli
<220> FEATURE:
<221> NAME/KEY: MISC_FEATURE
<222> LOCATION: (2)..(2)
<223> OTHER INFORMATION: The residue at this position is dLys.

<400> SEQUENCE: 13

Gln Lys Arg Ala Ala
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic

<400> SEQUENCE: 14

Gln Lys Arg Ala Glu
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic

<400> SEQUENCE: 15

Gln Glu Cys Leu Ala
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic

<400> SEQUENCE: 16
```

Asp Lys Cys Leu Ala
1               5

<210> SEQ ID NO 17
<211> LENGTH: 169
<212> TYPE: PRT
<213> ORGANISM: Artificial Sequence
<220> FEATURE:
<223> OTHER INFORMATION: Synthetic

<400> SEQUENCE: 17

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Asn Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Gly Asn Leu Glu Asp His Lys
65                  70                  75                  80

Asp Leu Leu Glu Gln Lys Arg Ala Ala Val Asp Thr Tyr Cys Val Asp
                85                  90                  95

Pro Ile Ser Arg Asp Leu Val Val Ser Tyr Val Asn Thr Asn Met Gly
            100                 105                 110

Leu Lys Phe Arg Gln Leu Leu Trp Phe His Ile Ser Cys Leu Thr Phe
        115                 120                 125

Gly Arg Glu Thr Val Ile Glu Tyr Leu Val Ser Phe Gly Val Trp Ile
    130                 135                 140

Arg Thr Pro Pro Ala Tyr Arg Pro Pro Asn Ala Pro Ile Leu Ser Thr
145                 150                 155                 160

Leu Pro Ala Trp Ala Arg Val Ile Asn
                165

<210> SEQ ID NO 18
<211> LENGTH: 169
<212> TYPE: PRT
<213> ORGANISM: Artificial Sequence
<220> FEATURE:
<223> OTHER INFORMATION: Synthetic

<400> SEQUENCE: 18

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Asn Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Gly Asn Leu Glu Asp His Lys
65                  70                  75                  80

Asp Ile Leu Glu Asp Glu Arg Ala Ala Val Asp Thr Tyr Cys Val Asp
                85                  90                  95

Pro Ile Ser Arg Asp Leu Val Val Ser Tyr Val Asn Thr Asn Met Gly
            100                 105                 110

Leu Lys Phe Arg Gln Leu Leu Trp Phe His Ile Ser Cys Leu Thr Phe
        115                 120                 125

Gly Arg Glu Thr Val Ile Glu Tyr Leu Val Ser Phe Gly Val Trp Ile
        130                 135                 140

Arg Thr Pro Pro Ala Tyr Arg Pro Pro Asn Ala Pro Ile Leu Ser Thr
145                 150                 155                 160

Leu Pro Ala Trp Ala Arg Val Ile Asn
                165

<210> SEQ ID NO 19
<211> LENGTH: 54
<212> TYPE: DNA
<213> ORGANISM: Artificial Sequence
<220> FEATURE:
<223> OTHER INFORMATION: Synthetic

<400> SEQUENCE: 19
cacaaggacc tcctggagca gaagcgggcc gcggtggaca cctactgcgt agat            54

<210> SEQ ID NO 20
<211> LENGTH: 54
<212> TYPE: DNA
<213> ORGANISM: Artificial Sequence
<220> FEATURE:
<223> OTHER INFORMATION: Synthetic

<400> SEQUENCE: 20
cacaaggaca tcctggaaga cgagcgggcc gcggtggaca cctactgcgt agat            54

<210> SEQ ID NO 21
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The amino acid at this position can be lysine,
      arginine, or histidine.
<220> FEATURE:
<221> NAME/KEY: MISC_FEATURE
<222> LOCATION: (3)..(4)
<223> OTHER INFORMATION: The amino acids at these positions can be any
      amino acid.

<400> SEQUENCE: 21

Gln Xaa Xaa Xaa Ala
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic

<400> SEQUENCE: 22

Gln Arg Ala Cys Ala
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic

<400> SEQUENCE: 23

```
Gln Lys Arg Ala Ala Cys
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic

<400> SEQUENCE: 24

Cys Gln Lys Arg Ala Ala
1               5

<210> SEQ ID NO 25
<211> LENGTH: 5
<212> TYPE: PRT
<213> ORGANISM: Escherichia coli
<220> FEATURE:
<221> NAME/KEY: MISC_FEATURE
<222> LOCATION: (3)..(3)
<223> OTHER INFORMATION: The amino acid at this position is selected
      from the group of amino acids consisting of alanine, valine,
      leucine, isoleucine, serine, threonine and asparagine.
<220> FEATURE:
<221> NAME/KEY: MISC_FEATURE
<222> LOCATION: (4)..(4)
<223> OTHER INFORMATION: The amino acid at this position is selected
      from the group of amino acids consisting of alanine, valine,
      isoleucine, serine, threonine and asparagine.

<400> SEQUENCE: 25

Gln Arg Xaa Xaa Ala
1               5

<210> SEQ ID NO 26
<211> LENGTH: 5
<212> TYPE: PRT
<213> ORGANISM: Escherichia coli
<220> FEATURE:
<221> NAME/KEY: MISC_FEATURE
<222> LOCATION: (3)..(3)
<223> OTHER INFORMATION: The amino acid at this position is selected
      from the group of amino acids consisting of alanine, valine,
      leucine, isoleucine, serine, threonine and asparagine.
<220> FEATURE:
<221> NAME/KEY: MISC_FEATURE
<222> LOCATION: (4)..(4)
<223> OTHER INFORMATION: The amino acid at this position is selected
      from the group of amino acids consisting of alanine, valine,
      isoleucine, serine, threonine and asparagine.

<400> SEQUENCE: 26

Gln Lys Xaa Xaa Ala
1               5

<210> SEQ ID NO 27
<211> LENGTH: 5
<212> TYPE: PRT
<213> ORGANISM: Escherichia coli
<220> FEATURE:
<221> NAME/KEY: MISC_FEATURE
<222> LOCATION: (3)..(3)
<223> OTHER INFORMATION: The amino acid at this position is selected
      from the group of amino acids consisting of alanine, valine,
      leucine, isoleucine, serine, threonine and asparagine.
<220> FEATURE:
<221> NAME/KEY: MISC_FEATURE
<222> LOCATION: (4)..(4)
<223> OTHER INFORMATION: The amino acid at this position is 2 is
      selected from the group of amino acids consisting of alanine,
``` valine, isoleucine, serine, threonine and asparagine.

<400> SEQUENCE: 27

Gln His Xaa Xaa Ala
1               5

<210> SEQ ID NO 28
<211> LENGTH: 14
<212> TYPE: PRT
<213> ORGANISM: Artificial Sequence
<220> FEATURE:
<223> OTHER INFORMATION: Synthetic

<400> SEQUENCE: 28

Lys Asp Leu Leu Glu Gln Arg Arg Ala Ala Val Asp Thr Tyr
1               5                   10

<210> SEQ ID NO 29
<211> LENGTH: 417
<212> TYPE: PRT
<213> ORGANISM: Artificial Sequence
<220> FEATURE:
<223> OTHER INFORMATION: Synthetic

<400> SEQUENCE: 29

Met Leu Leu Ser Val Pro Leu Leu Gly Leu Leu Gly Leu Ala Val
1               5                   10                  15

Ala Glu Pro Ala Val Tyr Phe Lys Glu Gln Phe Leu Asp Gly Asp
                20                  25                  30

Trp Thr Ser Arg Trp Ile Glu Ser Lys His Lys Ser Asp Phe Gly Lys
                35                  40                  45

Phe Val Leu Ser Ser Gly Lys Phe Tyr Gly Asp Glu Glu Lys Asp Lys
                50                  55                  60

Gly Leu Gln Thr Ser Gln Asp Ala Arg Phe Tyr Ala Leu Ser Ala Ser
65                  70                  75                  80

Phe Glu Pro Phe Ser Asn Lys Gly Gln Thr Leu Val Val Gln Phe Thr
                85                  90                  95

Val Lys His Glu Gln Asn Ile Asp Cys Gly Gly Gly Tyr Val Lys Leu
                100                 105                 110

Phe Pro Asn Ser Leu Asp Gln Thr Asp Met His Gly Asp Ser Glu Tyr
                115                 120                 125

Asn Ile Met Phe Gly Pro Asp Ile Cys Gly Pro Gly Thr Lys Lys Val
                130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
                180                 185                 190

Ser Gly Ser Leu Glu Asp Asp Trp Asp Phe Leu Pro Pro Lys Lys Ile
                195                 200                 205

Lys Asp Pro Asp Ala Ser Lys Pro Glu Asp Trp Asp Glu Arg Ala Lys
                210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys

-continued

```
                    260                 265                 270
Gly Glu Trp Lys Pro Arg Gln Ile Asp Asn Pro Asp Tyr Lys Gly Thr
            275                 280                 285

Trp Ile His Pro Glu Ile Asp Asn Pro Glu Tyr Ser Pro Asp Pro Ser
        290                 295                 300

Ile Tyr Ala Tyr Asp Asn Phe Gly Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Ala
            340                 345                 350

Ala Glu Lys Gln Met Lys Asp Lys Gln Asp Glu Glu Gln Arg Leu Lys
        355                 360                 365

Glu Glu Glu Glu Asp Lys Lys Arg Lys Glu Glu Glu Ala Glu Asp
    370                 375                 380

Lys Glu Asp Asp Glu Asp Lys Asp Glu Asp Glu Asp Glu Asp Glu Asp
385                 390                 395                 400

Lys Glu Glu Asp Glu Glu Glu Asp Val Pro Gly Gln Ala Lys Asp Glu
                405                 410                 415

Leu
```

```
<210> SEQ ID NO 30
<211> LENGTH: 7
<212> TYPE: PRT
<213> ORGANISM: Escherichia coli
<220> FEATURE:
<221> NAME/KEY: MISC_FEATURE
<222> LOCATION: (1)..(1)
<223> OTHER INFORMATION: The residue at this position can be any amino
      acid.
<220> FEATURE:
<221> NAME/KEY: MISC_FEATURE
<222> LOCATION: (7)..(7)
<223> OTHER INFORMATION: The residue at this position can be any amino
      acid.

<400> SEQUENCE: 30

Xaa Gln Arg Arg Ala Glu Xaa
1               5
```

```
<210> SEQ ID NO 31
<211> LENGTH: 7
<212> TYPE: PRT
<213> ORGANISM: Escherichia coli
<220> FEATURE:
<221> NAME/KEY: MISC_FEATURE
<222> LOCATION: (1)..(1)
<223> OTHER INFORMATION: The residue at this position can be any amino
      acid.
<220> FEATURE:
<221> NAME/KEY: MISC_FEATURE
<222> LOCATION: (7)..(7)
<223> OTHER INFORMATION: The residue at this position can be any amino
      acid.

<400> SEQUENCE: 31

Xaa Gln Arg Arg Ala Ala Xaa
1               5
```

```
<210> SEQ ID NO 32
<211> LENGTH: 7
<212> TYPE: PRT
<213> ORGANISM: Escherichia coli
<220> FEATURE:
```

```
<221> NAME/KEY: MISC_FEATURE
<222> LOCATION: (1)..(1)
<223> OTHER INFORMATION: The residue at this position can be any amino
      acid.
<220> FEATURE:
<221> NAME/KEY: MISC_FEATURE
<222> LOCATION: (7)..(7)
<223> OTHER INFORMATION: The residue at this position can be any amino
      acid.

<400> SEQUENCE: 32

Xaa Gln Arg Arg Thr Ala Xaa
1               5

<210> SEQ ID NO 33
<211> LENGTH: 7
<212> TYPE: PRT
<213> ORGANISM: Escherichia coli
<220> FEATURE:
<221> NAME/KEY: MISC_FEATURE
<222> LOCATION: (1)..(1)
<223> OTHER INFORMATION: The residue at this position can be any amino
      acid.
<220> FEATURE:
<221> NAME/KEY: MISC_FEATURE
<222> LOCATION: (7)..(7)
<223> OTHER INFORMATION: The residue at this position can be any amino
      acid.

<400> SEQUENCE: 33

Xaa Gln Lys Arg Leu Ala Xaa
1               5

<210> SEQ ID NO 34
<211> LENGTH: 7
<212> TYPE: PRT
<213> ORGANISM: Escherichia coli
<220> FEATURE:
<221> NAME/KEY: MISC_FEATURE
<222> LOCATION: (1)..(1)
<223> OTHER INFORMATION: The residue at this position can be any amino
      acid.
<220> FEATURE:
<221> NAME/KEY: MISC_FEATURE
<222> LOCATION: (7)..(7)
<223> OTHER INFORMATION: The residue at this position can be any amino
      acid.

<400> SEQUENCE: 34

Xaa Gln Lys Cys Leu Ala Xaa
1               5

<210> SEQ ID NO 35
<211> LENGTH: 7
<212> TYPE: PRT
<213> ORGANISM: Escherichia coli
<220> FEATURE:
<221> NAME/KEY: MISC_FEATURE
<222> LOCATION: (1)..(1)
<223> OTHER INFORMATION: The residue at this position can be any amino
      acid.
<220> FEATURE:
<221> NAME/KEY: MISC_FEATURE
<222> LOCATION: (7)..(7)
<223> OTHER INFORMATION: The residue at this position can be any amino
      acid.

<400> SEQUENCE: 35

Xaa Gln Lys Arg Ala Ala Xaa
1               5
```

```
<210> SEQ ID NO 36
<211> LENGTH: 7
<212> TYPE: PRT
<213> ORGANISM: Escherichia coli
<220> FEATURE:
<221> NAME/KEY: MISC_FEATURE
<222> LOCATION: (1)..(1)
<223> OTHER INFORMATION: The residue at this position can be any amino
      acid.
<220> FEATURE:
<221> NAME/KEY: MISC_FEATURE
<222> LOCATION: (7)..(7)
<223> OTHER INFORMATION: The residue at this position can be any amino
      acid.

<400> SEQUENCE: 36

Xaa Asp Glu Arg Ala Ala Xaa
1               5

<210> SEQ ID NO 37
<211> LENGTH: 21
<212> TYPE: DNA
<213> ORGANISM: Artificial Sequence
<220> FEATURE:
<223> OTHER INFORMATION: Synthetic

<400> SEQUENCE: 37
ggatagcagc atggcgggcc g                                             21

<210> SEQ ID NO 38
<211> LENGTH: 21
<212> TYPE: DNA
<213> ORGANISM: Artificial Sequence
<220> FEATURE:
<223> OTHER INFORMATION: Synthetic

<400> SEQUENCE: 38
cggcccgcca tgctgctatc c                                             21
```

METHODS AND COMPOSITIONS FOR THE TREATMENT OF MHC-ASSOCIATED CONDITIONS

This application is a continuation-in-part of patent application Ser. No. 10/161,959, filed Jun. 3, 2002, now abandoned herein incorporated by reference in its entirety.

The present invention was made, in part, with government support under Grant No. R01 AI47331 awarded by the National Institutes of Health. The government may have certain rights in the invention.

FIELD OF THE INVENTION

The present invention relates to methods and compositions for counteracting and reversing disease-causing signaling defects in disorders with underlying signal transduction aberrations, including but not limited to rheumatoid arthritis.

BACKGROUND

Several signaling pathways are involved in a wide range of physiologic functions in the immune, cardiovascular, endocrine and nervous systems. Two of these pathways are the cyclic adenosine 3',5' monophosphate (cAMP)-mediated pathway and the nitric oxide (NO)-mediated pathway. These pathways interact at a number of levels.

The diseases associated with signal transduction abnormalities (either increased or decreased signaling) include (but are not limited to) Alzheimer's disease, polycystic kidney disease, prostate cancer, atopic dermatitis, osteoarthritis, septic shock, congestive heart failure and rheumatoid arthritis (RA). Over 50 diseases are known to be associated with specific major histocompatibility (MHC) alleles. Of these, RA is among the most prevalent, affecting 1–2% of the population. Over 50,000,000 individuals are afflicted with RA worldwide. At present, there is no cure for RA. What is needed is a way to counteract and reverse disease-causing signaling defects in conditions associated with major histocompatibility (MHC) aberrations, including but not limited to rheumatoid arthritis.

SUMMARY OF THE INVENTION

In one embodiment, the present invention provides a method of treating a disease with an underlying signal transduction aberration (including, but not limited to those diseases listed in Tables 1 and 2) comprising: a) providing: i) a subject with one or more symptoms of a disease with an underlying signal transduction aberration, and ii) a preparation comprising a shared epitope (SE) antagonist-containing peptide; and b) administering said preparation to said subject. In one embodiment, said administration to said subject is under conditions such that said one or more signs and symptoms are improved.

In some embodiments, said shared epitope antagonist-containing peptides are synthetic peptides. In some embodiments, the shared epitope antagonist-containing peptides are naturally occurring peptides or fragments thereof. In still other embodiments, said shared epitope antagonist-containing peptides are non-naturally occurring. In other embodiments, said shared epitope antagonist-containing peptides range in length from five amino acids to 75 amino acids. In other embodiments, said shared epitope antagonist-containing peptides range in length from five amino acids to 25 amino acids, more preferably from five amino acids to 15 amino acids. In other embodiments, shared epitope antagonist-containing peptides may be longer than 75 amino acids.

In some embodiments, said shared epitope antagonist-containing peptides are conjugates, coupled to at least one moiety. In some embodiments, shared epitope antagonist-containing peptides are synthetic peptides that are conjugates, coupled to at least one moiety. In one embodiment, said conjugation is at the N-terminus of said peptides. In other embodiments, said conjugation is at the C-terminus of said peptides. In yet other embodiments, said conjugation is at both the N- and the C-terminus of said peptides. In other embodiments, said conjugated moiety is a carrier molecule. In such embodiments, said shared epitope antagonist-containing peptide is conjugated to at least one carrier. Such carrier molecules facilitate targeting or delivery of the conjugate composition to a particular tissue or organ (e.g. a carrier molecule having affinity for a surface antigen of said tissue or organ). In some embodiments, said carrier molecule is selected from the group consisting of lipophilic moieties, antibodies (including antibody fragments such as Fc, Fab, single chain, and $Fab_2$) and polyamines. In some embodiments, said carrier molecule is directly conjugated, while in other embodiments, said carrier molecule is conjugated via a crosslinker. In some embodiments, said lipophilic moiety is in the form of a saturated or unsaturated radical, such as hydrocarbyl or carboxylic acyl having at least five carbon atoms. In some embodiments, said lipophilic moiety is conjugated at the N terminus of said synthetic peptide, in other embodiments, said lipophilic moiety is conjugated at the C terminus of said synthetic peptide. In yet other embodiments, said lipophilic moiety is conjugated to both the N and the C terminus.

In some embodiments, said shared epitope antagonist-containing peptide comprises SEQ ID NO:16 or structure or function equivalents.

In another embodiment, the present invention contemplates a method of treating a disease with an underlying signal transduction aberration (including, but not limited to those diseases listed in Tables 1 and 2) comprising: a) providing: i) a subject with one or more signs and symptoms of a disease with an underlying signal transduction aberration, and ii) a preparation comprising an shared epitope antagonist-containing peptide-mimicking agent, such as an analogue, derivative or mimetic of a shared epitope antagonist-containing peptides; and b) administering said preparation to said subject. In one embodiment, said administration to said subject is under conditions such that said one or more signs and symptoms are improved. In another embodiment, said analogues, derivatives or mimetics still retain biological activity.

In another embodiment, the present invention contemplates a method of treating a disease with an underlying signal transduction aberration (including, but not limited to those diseases listed in Tables 1 and 2) comprising: a) providing: i) a subject with one or more signs and symptoms of a disease with an underlying signal transduction aberration, and ii) a preparation comprising an antagonist of an shared epitope- or shared epitope motif-containing peptide; and b) administering said preparation to said subject. In one embodiment, said administration to said subject is under conditions such that said one or more signs and symptoms are reduced. In another embodiment, said antagonist retains biological activity. In still further embodiments, the biological activity of said antagonists is reduced or absent. In some embodiments, said antagonists with reduced or absent biological activity retain binding affinity for a receptor molecule. In still further embodiments said receptor molecule is calreticulin.

In some embodiments, the method of the present invention employs shared epitope antagonist-containing peptide-mimicking agents. In some embodiments, the shared epitope antagonist-containing peptide-mimicking agents (such as analogues, derivatives or mimetics of shared epitope antagonist-containing peptides) are peptides. In other embodiments, said analogues, derivatives, or mimetics of shared epitope antagonist-containing peptides are non-peptide compounds. In cases where said shared epitope antagonist-containing peptide analogues, derivatives, or mimetics are peptides, the length of said peptides may vary. In one embodiment, said peptides range in length from five amino acids to 75 amino acids. In other embodiments, said peptides range in length from five amino acids to 25 amino acids, and more preferably from five amino acids to fifteen amino acids.

In another embodiment, said shared epitope antagonist-containing peptide analogues, derivatives, or mimetics are conjugates, coupled to at least one moiety. In one embodiment, said conjugation is at the N-terminus of said analogues, derivatives, or mimetics. In other embodiments, said conjugation is at the C-terminus of said analogues, derivatives, or mimetics. In yet other embodiments, said conjugation is at both the N- and the C-terminus of said analogues, derivatives, or mimetics. In other embodiments, said conjugated moiety is a carrier molecule. In such embodiments, said analogues, derivatives, or mimetics are conjugated to at least one carrier. Such carrier molecules facilitate targeting or delivery of the conjugate composition to a particular tissue or organ (e.g. by affinity for a target molecule on said organ or tissue). In some embodiments, said carrier molecule is selected from the group consisting of lipophilic moieties, antibodies (including fragments) and polyamines. In some embodiments, said carrier molecule is directly conjugated, while in other embodiments, said carrier molecule is conjugated via a crosslinker. In some embodiments, said lipophilic moiety is in the form of a saturated or unsaturated radical, such as hydrocarbyl or carboxylic acyl having at least five carbon atoms. In some embodiments, said lipophilic moiety is conjugated at the C terminus, while in other embodiments, said lipophilic moiety is conjugated at the N terminus. In other embodiments, said lipophilic moiety is conjugated to both the N and the C terminus.

In yet other embodiments, said shared epitope antagonist-containing peptide analogues, derivatives, or mimetics are biologically active nonpeptide compounds. In such cases, conjugation (e.g. to a carrier molecule) may be direct or through a crosslinker, to an appropriate region of said nonpeptide compound (so as not to interfere with the biological activity of said nonpeptide compound).

A variety of modes of administration of the compounds of the present invention are contemplated. In some embodiments, said administration is parenteral (e.g. intravenous), in other embodiments, said administration is oral. In other embodiments, said administration is intranasal or respiratory. In yet other embodiments, said administration is cutaneous, transdermal or transmucosal (e.g. by application of a composition comprising the compounds of the invention to a body surface). In yet other embodiments, said administration is by injection directly to an affected area (e.g. a joint or a particular organ). A variety of pharmaceutically acceptable formulations are contemplated in the present invention. Among dosage forms contemplated (as appropriate for the mode of administration and desired target organ or tissue) are pills, tablets, lozenges, suspensions, aqueous or organic solutions, capsules, aerosols, creams, lotions, jellies, patches, powders and the like. Such dosage forms are formulated with pharmaceutically acceptable vehicles as is known in the art.

In one embodiment, the present invention contemplates a method of treating rheumatoid arthritis comprising: a) providing: i) a subject with one or more signs or symptoms of rheumatoid arthritis, and ii) a preparation comprising an shared epitope antagonist-containing peptide; and b) administering said preparation to said subject. In one embodiment, said administration to said subject is under conditions such that said one or more signs or symptoms are improved.

In some embodiments, said shared epitope antagonist-containing peptides are synthetic peptides. In further embodiments, said synthetic peptide comprises (or consists of) the sequence DKCLA [Asp Lys Cys Leu Ala] [SEQ ID NO: 16].

In some embodiments, the peptides are naturally occurring peptides or fragments thereof. In further embodiments, said shared epitope antagonist-containing peptides are non-naturally occurring. In other embodiments, said shared epitope antagonist-containing peptides range in length from five amino acids to 75 amino acids. In other embodiments, said shared epitope antagonist-containing peptides range in length from five amino acids to 25 amino acids, more preferably from five amino acids to 15 amino acids. In other embodiments, said shared epitope antagonist-containing peptides may be longer than 75 amino acids.

In some embodiments, said shared epitope antagonist-containing peptides are synthetic peptides that are conjugates, coupled to at least one moiety. In one embodiment, said conjugation is at the N-terminus of said peptides. In other embodiments, said conjugation is at the C-terminus of said peptides. In yet other embodiments, said conjugation is at both the N- and the C-terminus of said peptides. In other embodiments, said conjugated moiety is a carrier molecule. In such embodiments, said shared epitope antagonist-containing peptide is conjugated to at least one carrier. Such carrier molecules facilitate targeting or delivery of the conjugate composition to a particular tissue or organ (e.g. by affinity binding to a target molecule on tissue, such as synovial tissue). In a preferred embodiment, said tissue or organ comprises synovial tissue in a joint. In some embodiments, said carrier molecule is selected from the group consisting of lipophilic moieties, antibodies (including fragments) and polyamines. In some embodiments, said carrier molecule is directly conjugated, while in other embodiments, said carrier molecule is conjugated via a crosslinker. In some embodiments, said lipophilic moiety is in the form of a saturated or unsaturated radical, such as hydrocarbyl or carboxylic acyl having at least five carbon atoms. In some embodiments, said lipophilic moiety is conjugated at the N terminus of said synthetic peptide, in other embodiments, said lipophilic moiety is conjugated at the C terminus of said synthetic peptide. In yet other embodiments, said lipophilic moiety is conjugated to both the N and the C terminus.

In another embodiment, the present invention contemplates a method of treating rheumatoid arthritis comprising: a) providing: i) a subject with one or more signs or symptoms of rheumatoid arthritis, and ii) a preparation comprising an analogue, derivative, mimetic of a shared epitope antagonist-containing peptide; and b) administering said preparation to said subject. In one embodiment, said administration to said subject is under conditions such that said one or more signs or symptoms are improved. In another embodiment, said analogues, derivatives, or mimetics retain biological activity. In still further embodiments, the biological activity of said antagonists is reduced or absent. In some embodiments, said antagonists with reduced or absent biological activity retain binding affinity for a receptor molecule. In still further embodiments said receptor molecule is calreticulin.

In one embodiment, said shared epitope antagonist-containing peptide analogues, derivatives, or mimetics are conjugates, coupled to at least one moiety. In some embodiments, said analogues, derivatives or mimetics are synthetic peptides that are conjugates, coupled to at least one moiety. In one embodiment, said conjugation is at the N-terminus of said shared epitope antagonist-containing peptide analogues, derivatives, mimetics or antagonists. In other embodiments, said conjugation is at the C-terminus of said analogues, derivatives, mimetics or antagonists. In yet other embodiments, said conjugation is at both the N- and the C-terminus of said shared epitope antagonist-containing peptide analogues, derivatives, mimetics or antagonists. In other embodiments, said conjugated moiety is a carrier molecule. In such embodiments, said shared epitope antagonist-containing peptide analogues, derivatives or mimetics are conjugated to at least one carrier. Such carrier molecules facilitate targeting or delivery of the conjugate composition to a particular tissue or organ. In a preferred embodiment, said tissue or organ comprises synovial tissue in a joint. In some embodiments, said carrier molecule is selected from the group consisting of lipophilic moieties, antibodies and polyamines. In some embodiments, said carrier molecule is directly conjugated, while in other embodiments, said carrier molecule is conjugated via a crosslinker. In some embodiments, said lipophilic moiety is in the form of a saturated or unsaturated radical, such as hydrocarbyl or carboxylic acyl having at least five carbon atoms. In some embodiments, said lipophilic moiety is conjugated at the N terminus, in other embodiments, said lipophilic moiety is conjugated at the C terminus. In yet other embodiments, said conjugation is at both the N and the C terminus.

In yet other embodiments, said shared epitope antagonist-containing peptide analogues, derivatives, and mimetics are biologically active nonpeptide compounds. In such cases, conjugation (e.g. to a carrier molecule) may be direct or through a crosslinker, to an appropriate region of said nonpeptide compound (so as not to interfere with the biological activity of said nonpeptide compound).

A variety of methods of administration of the compounds of the present invention for the treatment of rheumatoid arthritis are contemplated. In some embodiments, said administration is parenteral (e.g. intravenous), in other embodiments, said administration is oral. In other embodiments, said administration is intranasal or respiratory. In yet other embodiments, said administration is cutaneous, transdermal or transmucosal (e.g. by application of a composition comprising the compounds of the invention to a body surface). In yet other embodiments, said administration is by injection directly to an affected area (e.g. a particular organ). A variety of pharmaceutically acceptable formulations are contemplated in the present invention. Among dosage forms contemplated (as appropriate for the mode of administration and desired target organ or tissue) are pills, tablets, lozenges, suspensions, aqueous or organic solutions, capsules, aerosols, creams, lotions, jellies, patches, powders and the like. Such dosage forms are formulated with pharmaceutically acceptable vehicles as is known in the art. In the case of treatment of rheumatoid arthritis, one preferred embodiment is direct application of compositions comprising compounds of the present invention directly to the joint. Such application may be accomplished, in one embodiment, by direct injection, or by implantation of a catheter and pump system for delivery into the joint.

The dosage of the compositions used in the methods of the present invention (shared epitope antagonist-containing peptides, or shared epitope antagonist-containing peptide analogues, derivatives, or mimetics) is any that is effective to improve one or more signs or symptoms of the subject. In some embodiments, the dosage is sufficient to attain a serum or local concentration in the range of approximately 0.5 µg/ml to approximately 500 µg/ml. In a preferred embodiment, the serum concentration is in the range of approximately 5 µg/ml to approximately 100 µg/ml, and even more preferably in the range of approximately 10 µg/ml to approximately 50 µg/ml.

In one embodiment, the present invention contemplates a method of treating a disease with an underlying signal transduction aberration (including, but not limited to those diseases listed in Tables 1 and 2) comprising: a) providing: i) a subject with one or more symptoms of a disease with an underlying signal transduction aberration, and ii) a preparation comprising an antagonist of a shared epitope- or shared epitope motif-containing peptide; and b) administering said preparation to said subject. In one embodiment, said administration to said subject is under conditions such that said one or more symptoms are reduced.

In some embodiments said disease with an underlying signal transduction aberration is caused by decreased cAMP signaling, including, for example, asthma, atopic dermatitis, glomerulonephritis, psoriasis, rheumatoid arthritis, or systemic lupus erythematosus. In other embodiments, said disease with an underlying signal transduction aberration is caused by increased NO signaling including, for example, infectious disease, inflammatory bowel disease, osteoarthritis, septic shock, or uremia. In still further embodiments, said disease with an underlying signal transduction aberration is associated with shared epitope positive HLA-DRB1 alleles, including, for example, polymyalgia rheumatica, giant cell arteritis, insulin dependent diabetes mellitus, autoimmune hepatitis, early-onset chronic lymphoid leukemia, or solid organ or formed element transplantation rejection. In yet other embodiments, said disease with an underlying signal transduction abnormality is caused by oxidative DNA damage. In preferred embodiments, said disease with an underlying signal transduction abnormality is caused by oxidative stress. In a preferred embodiment, said disease with an underlying signal transduction aberration is prevented in a genetically susceptible subject before the onset of signs or symptoms by the administration of preparation comprising an antagonist of a shared epitope- or shared epitope motif-containing peptide.

In some embodiments, said antagonist is a conjugate, coupled to another moiety. In some embodiments, said conjugated moiety is a carrier molecule. Such carrier molecules facilitate targeting or delivery of the conjugate composition to a particular tissue or organ. In some embodiments, said carrier molecule is selected from the group consisting of lipophilic moieties, antibodies (including fragments) and polyamines. In some embodiments, said carrier molecule is directly conjugated, while in other embodiments, said carrier molecule is conjugated via a crosslinker.

In some embodiments, said shared epitope or shared epitope motif-containing peptide antagonists are synthetic peptides. In other emobidments, said synthetic peptides comprise (or consist of) shared epitope antagonist-containing peptides. In particularly preferred embodiments, said shared epitope antagonist-containing peptide comprises (or consists of) the sequence DKCLA [Asp Lys Cys Leu Ala] [SEQ ID NO: 16]. In further embodiments, said shared epitope antagonist-containing peptide comprises the motif Q-(K/R)-X-X-A in which Q is replaced by D. In still further embodiments, shared epitope antagonist-containing peptides comprise the HLA-DRB1 70–74 sequence in rheumatoid arthritis-protective alleles.

In yet other embodiments, said antagonists are biologically active nonpeptide compounds. In still further embodiments, the biological activity of said antagonists is reduced or absent. In some embodiments, said anagonists with reduced or absent biological activity retain binding affinity for a receptor molecule. Conjugation of said anatagonists (e.g. to a carrier molecule) may be direct or through a crosslinker, to an appropriate region of said nonpeptide compound (so as not to interfere with the biological activity of said nonpeptide compound).

A variety of methods of administration of the compounds of the present invention for the treatment of said disease with an underlying signal transduction aberration are contemplated. In some embodiments, said administration is parenteral (e.g. intravenous), in other embodiments, said administration is oral. In other embodiments, said administration is intranasal or respiratory. In yet other embodiments, said administration is cutaneous, transdermal or transmucosal (e.g. by application of a composition comprising the compounds of the invention to a body surface). In yet other embodiments, said administration is by injection directly to an affected area (e.g. a joint or a particular organ). A variety of pharmaceutically acceptable formulations are contemplated in the present invention. Among dosage forms contemplated (as appropriate for the mode of administration and desired target organ or tissue) are pills, tablets, lozenges, suspensions, aqueous or organic solutions, capsules, aerosols, creams, lotions, jellies, patches, powders and the like. Such dosage forms are formulated with pharmaceutically acceptable vehicles as is known in the art. In the case of treatment of rheumatoid arthritis, one preferred embodiment is direct injection of compositions comprising compounds of the present invention directly into an affected joint. In other embodiments, such compositions suitable for intra-articular injection further comprise an anesthetic.

The present invention also contemplates the in vivo delivery of exogenous nucleic acids encoding a shared epitope antagonist-containing peptide. While nucleic acids can be introduced to mammalian cells in vitro by a variety of physical methods, including transfection, direct microinjection, electroporation, and coprecipitation with calcium phosphate, most of these techniques are impractical for delivering genes to cells within intact animals. Therefore, a preferred approach is Receptor-Mediated DNA Delivery In Vivo or any of a variety of methods known in the art.

Receptor-mediated gene transfer has been shown to be successful in introducing transgenes into suitable recipient cells, both in vitro and in vivo. This procedure involves linking the DNA to a polycationic protein (usually poly-L-lysine) containing a covalently attached ligand, which is selected to target a specific receptor on the surface of the tissue of interest. The gene is taken up by the tissue, transported to the nucleus of the cell and expressed for varying times. The overall level of expression of the transgene in the target tissue is dependent on several factors: the stability of the DNA-carrier complex, the presence and number of specific receptors on the surface of the targeted cell, the receptor-carrier ligand interaction, endocytosis and transport of the complex to the nucleus, and the efficiency of gene transcription in the nuclei of the target cells.

Wu, et al., U.S. Pat. No. 5,166,320 (hereby incorporated by reference) discloses tissue-specific delivery of DNA using a conjugate of a polynucleic acid binding agent (such as polylysine, polyarginine, polyonithine, histone, avidin, or protamine) and a tissue receptor-specific protein ligand. For targeting liver cells, Wu suggests "asialoglycoprotein (galactose-terminal) ligands".

Wagner, et al., *Proc. Natl. Acad. Sci.,* 88:4255–4259 (1991) and U.S. Pat. No. 5,354,844 (hereby incorporated by reference) disclose complexing a transferrin-polylysine conjugate with DNA for delivering DNA to cells via receptor mediated endocytosis. Wagner, et al., teach that it is important that there be sufficient polycation in the mixture to ensure compaction of plasmid DNA into toroidal structures of 80–100 nm diameter, which, they speculate, facilitate the endocytic event.

The possibility of detecting gene expression by directly injecting naked DNA into animal tissues was demonstrated first by Dubenski et al., *Proc. Nat. Acad. Sci. USA,* 81:7529–33 (1984), who showed that viral or plasmid DNA injected into the liver or spleen of mice was expressed at detectable levels. The DNA was precipitated using calcium phosphate and injected together with hyaluronidase and collagenase. The transfected gene was shown to replicate in the liver of the host animal. Benvenisty and Reshef, *Proc. Nat. Acad. Sci. USA,* 83:9551–55 (1986) injected calcium phosphate precipitated DNA intraperitoneally into newborn rats and noted gene expression in the livers of the animals 48 hours after transfection. In 1990, Wolff et al., *Science,* 247:1456–68 (1990), reported that the direct injection of DNA or RNA expression vectors into the muscle of mice resulted in the detectable expression of the genes for periods for up to 2 months. This technique has been extended by Acsadi et al., *New Biologist,* 3:71–81 (1991) to include direct injection of naked DNA into rat hearts; the injected genes were expressed in the heart of the animals for up to 25 days. Other genes, including the gene for dystrophin have been injected into the muscle of mice using this technique.

In one embodiment of the present invention, the DNA used is compacted to improve its survival in the cell, its uptake into the nucleus or its rate of transcription in the nucleus of the target cells. For example, the nucleic acid can be compacted at high concentrations with the carrier molecule at a critical salt concentration. The nucleic acid-loaded carrier molecule is then administered. In some embodiments, a tissue-specific carrier molecule is prepared, which is a bifunctional molecule having a nucleic acid-binding moiety and a target tissue-binding moiety.

In one embodiment, the present invention contemplates a method for delivering an oligonucleotide to cells of an animal, comprising: a) providing: i) a target binding moiety capable of binding to a polymeric immunoglobulin receptor present on the surface of a cell in a tissue of an animal; ii) a nucleic acid binding moiety; iii) an expression vector comprising an oligonucleotide encoding a shared epitope antagonist-containing peptide; iv) a subject; b) conjugating said target binding moiety to said nucleic acid binding moiety to form a carrier; c) coupling said carrier with said expression vector to form a pharmaceutical composition; and d) administering said composition to said subject. It is preferred that said expression vector (i.e., nucleic acid) is compacted.

In a preferred embodiment, the oligonucleotide is delivered to a tissue such as the synovium or joint space. In a preferred embodiment, the expression vector further comprises a promoter sequence operably linked to the oligonucleotide. The invention is not limited by the nature of the promoter sequence chosen. In one embodiment, said target binding moiety is an antibody directed against a target molecule on synovial tissue. It is preferred that said antibody is a monoclonal antibody or fragment thereof.

It is not intended that the present invention be limited by the nature of the nucleic acid binding moiety. In one embodiment, the nucleic acid binding moiety is a polycation, such as poly-L-lysine.

It is also not intended that the present invention be limited by the nature of the administration of the composition. In one embodiment, said administering comprises injection of said composition into said recipient animal (e.g., by intravenous injection).

In one embodiment, the present invention contemplates a method, comprising: a) providing: i) a subject having one or more signs or symptoms of rheumatoid arthritis, and ii) a preparation comprising a a calreticulin antagonist compound, and b) administering said preparation to said subject under conditions such that said one or more signs or symptoms are reduced. In a further embodiment, said rheumatoid arthritis is prevented in a genetically susceptible subject before the onset of signs or symptoms by the administration of a preparation comprising said calreticulin antagonist compound.

In one embodiment, said calreticulin antagonist compound is a shared epitope antagonist-containing peptide. In a further embodiment, said shared epitope antagonist-containing peptide is a synthetic peptide. In a preferred embodiment, said synthetic peptide comprises SEQ ID NO: 16.

In another embodiment, said synthetic peptides are conjugates, coupled to at least one moiety, wherein said moiety is a lipophilic moiety, in the form of saturated or unsaturated radical, such as hydrocarbyl or carboxylic acyl having at least 5 carbon atoms.

In one embodiment, said lipophilic moiety is conjugated at the C-terminus of said synthetic peptide. In another embodiment, said lipophilic moiety is conjugated at the N-terminus of said synthetic peptide. In a further embodiment, said lipophilic moiety is conjugated to both the N-terminus and the C-terminus.

In one embodiment, the present invention contemplates a shared epitope antagonist-containing peptide conjugated to at least one carrier molecule, wherein said carrier molecule is an antibody.

The present invention also contemplates the use of non-peptide mimetics of shared epitope antagonist-containing peptide peptides.

In one embodiment, said calreticulin antagonist compound is one or more antibodies. In a further embodiment, said antibodes comprise an anti-calreticulin antibody. In another embodiment, said calreticulin antagonist compound is an antisense oliogonucleotide configured to inhibit expression of calreticulin. In a still further embodiment, said calreticulin antagonist compound is a small interfering RNA duplex, or vectors encoding said small interfering RNA duplex, configured to inhibit expression of calreticulin.

BRIEF DESCRIPTION OF THE DRAWINGS

FIG. 1A is a bar graph that shows PKA activation in different cell types, with or without forskolin stimulation. (FIG. 1A abbreviations: NL, normal donors: RA, rheumatoid arthritis; HZ; homozygous tissue typing lines expressing the RA shared epitope; FSK, forskolin; PKA, protein kinase A.) FIG. 1B shows PKA activation over time in different cells. (FIG. 1B. abbreviations: L565, murine L cells transfected with HLA-DRB1*0401; L259, murine L cells transfected with HLA-DRB1*0403, L300, murine L cells transfected with HLA-DRB1*0404 mm, minutes.) FIG. 1C is a bar graph that shows relative PKA activation in different cells expressing different HLA DRB1 alleles. (FIG. 1C abbreviations: WT, wild type; *0404, murine L cell transfectants expressing HLA-DRB1*0404, *0403, murine L cell transfectants expressing HLA-DRB1*0403; Q70D, substitution of residue number 70 from glutamine to aspartic acid; R71K, substitution of residue number 71 from arginine to lysine; R71E, substitution of residue number 71 from arginine to glutamic acid; A74E, substitution of residue number 74 from alanine to glutamic acid; E47A, substitution of residue number 74 from glutamic acid to alanine.)

(FIG. 2 abbreviations: 2CA, 2-chloroadenosine; $PGE_1$, prostaglandin E1, FSK, forskolin; 8-Br-cAMP, 8-bromo-cyclic AMP; H-89, a chemical inhibitor of protein kinase A; 8-Br-cGMP, 8-bromo-cyclic GMP; SNAP, S-nitroso-N-acetyl-penicillamine.) FIG. 2A is a graph which shows DNA repair in the presence of different concentrations of 2CA. FIG. 2B is a graph which shows DNA repair in the presence of different concentrations of PGE.sub.1. FIG. 2C is a graph which shows DNA repair in the presence of different concentrations of forskolin. FIG. 2D is a graph which shows DNA repair in the presence of different concentrations of 8-Br-cAMP. FIG. 2E is a graph that shows DNA repair in the presence of different concentrations of enprofylline. FIG. 2F is a graph which shows DNA repair in the presence of different concentrations of H-89. FIG. 2G is a graph that shows DNA repair in the presence of different concentrations of 8-Br-cGMP. FIG. 2H is a bar graph which shows DNA repair in the presence or absence of SNAP.

FIG. 3A shows DNA repair in HEK293/A.sub.2a transfectants in the presence of different concentrations of 2CA. (FIG. 3A abbreviations: HEK293/A2a, human embryonic kidney 293 cells transfected with A2a adenosine receptor; 2CA, 2-chloroadenosine; M, Molar.) FIG. 3B shows DNA repair in HEK293/A.sub.2b transfectants in the presence of different concentrations of 2CA. (FIG. 3B abbreviations: HEK293/A2b, human embryonic kidney 293 cells transfected with A2b adenosine receptor; 2CA, 2-chloroadenosine; M, Molar.) FIG. 3C is a bar graph that shows DNA repair in HEK293/A.sub.1 transfectants in the presence of different concentrations of 2CA and cAMP. (FIG. 3C abbreviations: HEK293/A1, human embryonic kidney 293 cells transfected with A1 adenosine receptor; 2CA, 2-chloroadenosine; cAMP, cyclic AMP.)

FIG. 4A is a graph showing DNA repair over time in two transfected cell lines. (FIG. 4A abbreviations; L514, L cells transfected with HLA-DRB1*0402; L565, L cells transfected with HLA-DRB1*0401.) FIG. 4B is a bar graph which shows DNA repair in different L cell transfectants. (FIG. 1B abbreviations: L565, L cells transfected with HLA-DRB1*0401; L514, L cells transfected with HLA-DRB1*0402; L259, L cells transfected with HLA-DRB1*0403.)

(FIG. 5 abbreviations:

65–79*0401, synthetic peptide corresponding to amino acids 65–79 of the β chain encoded by the HLA-DRB*0401 allele; 65–79*0402, synthetic peptide corresponding to amino acids 65–79 of the β chain encoded by the HLA-DRB*0402 allele; 65–79*0403, synthetic peptide corresponding to amino acids 65–79 of the β chain encoded by the HLA-DRB*0403 allele; 65–79*0404, synthetic peptide corresponding to amino acids 65–79 of the β chain encoded by the HLA-DRB*0404 allele.)

Figure 6:
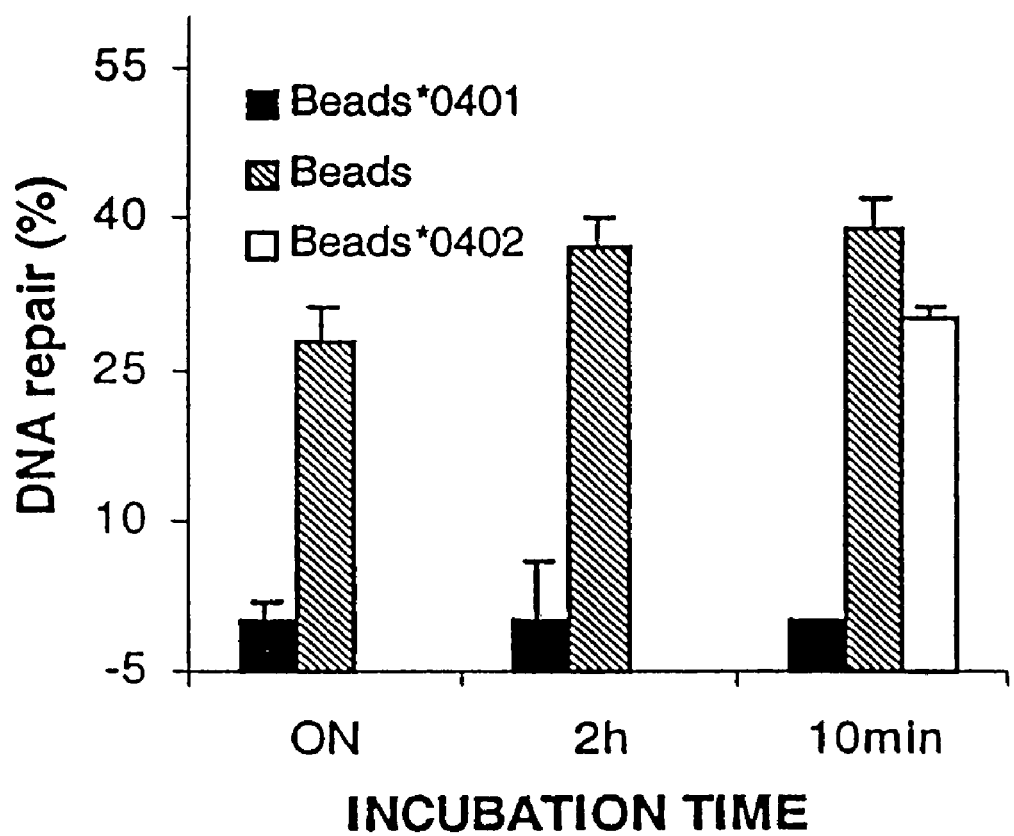

FIG. 6 is a bar graph that depicts the experimental results demonstrating the inhibition of cAMP-mediated inducible DNA repair by shared epitope-containing peptide-conjugated beads. (FIG. 6 abbreviations; Bead*0401, peptide 65–79*0401 (corresponding to amino acids 65–79 of the β chain encoded by the HLA-DRB*0401 allele) chemically conjugated to Sepharose beads; Beads, unconjugated Sepharose beads; Bead*0402, peptide 65–79*0402 (corresponding to amino acids 65–79 of the β chain encoded by the HLA-DRB*0402 allele) chemically conjugated to Sepharose beads; ON, overnight; h, hours; min, minutes.)

FIG. 7 is an alignment that depicts shared eptiope homologies in several proteins. (FIG. 7 abbreviations; H. Laminin, human laminin; M. laminin, mouse laminin; APLP1, amyloid precursor protein-like protein 1; ApoE, apolipoprotein E.)

Figure 8:
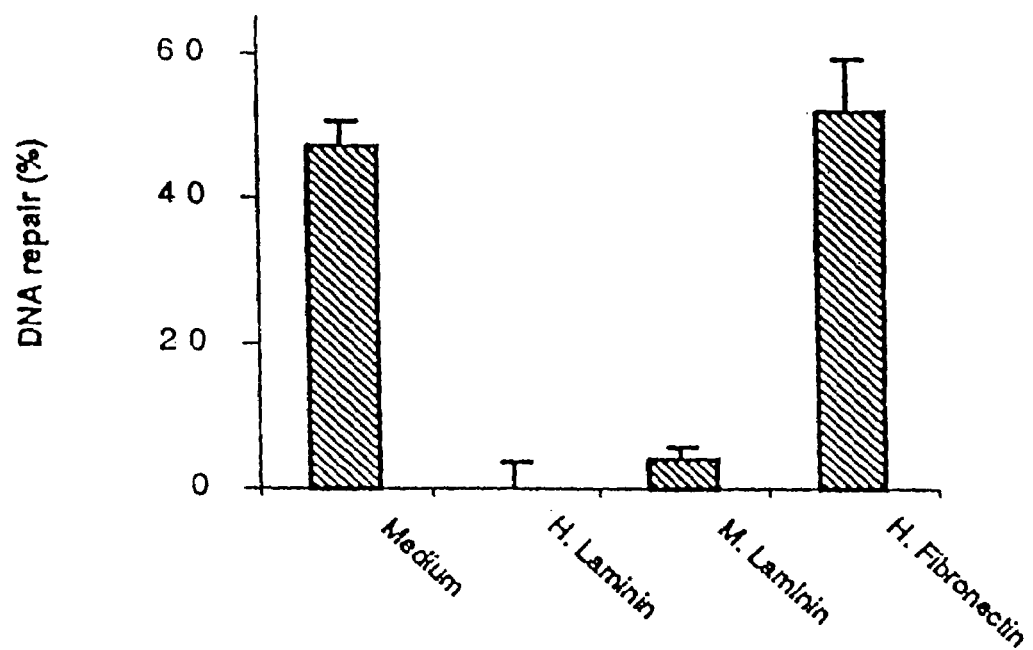

FIG. 8 is a bar graph which depicts the inhibition of cAMP-dependent DNA repair by shared epitope-containing, non DRβ proteins. (FIG. 8 abbreviations: H. Laminin, human laminin; M. laminin, mouse laminin; H. Fibronectin, human fibronectin.)

Figure 9:
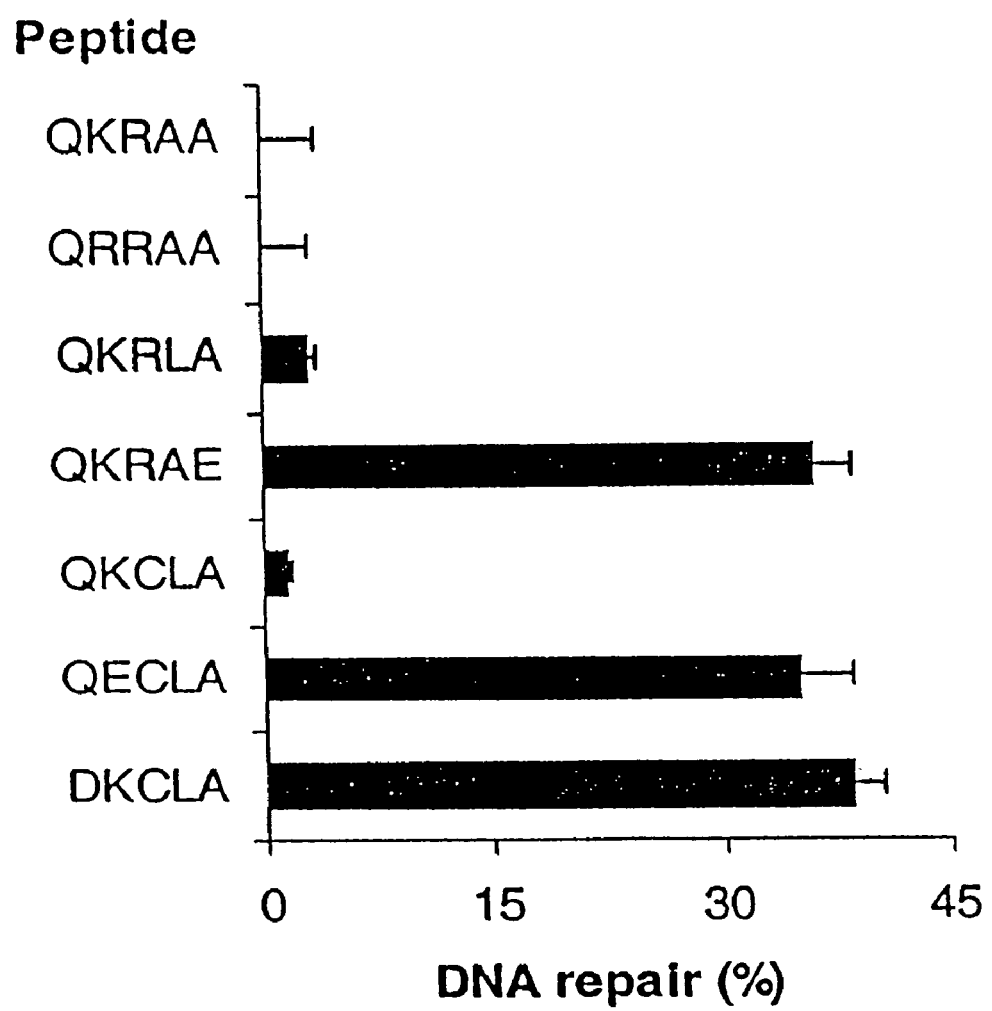

FIG. 9, respectively, (SEQ ID NOS: 1, 2, 11, 14, 12, 15 and 16) is a bar graph that depicts the results of experiments carried out to determine the shared epitope motif.

Figure 10:
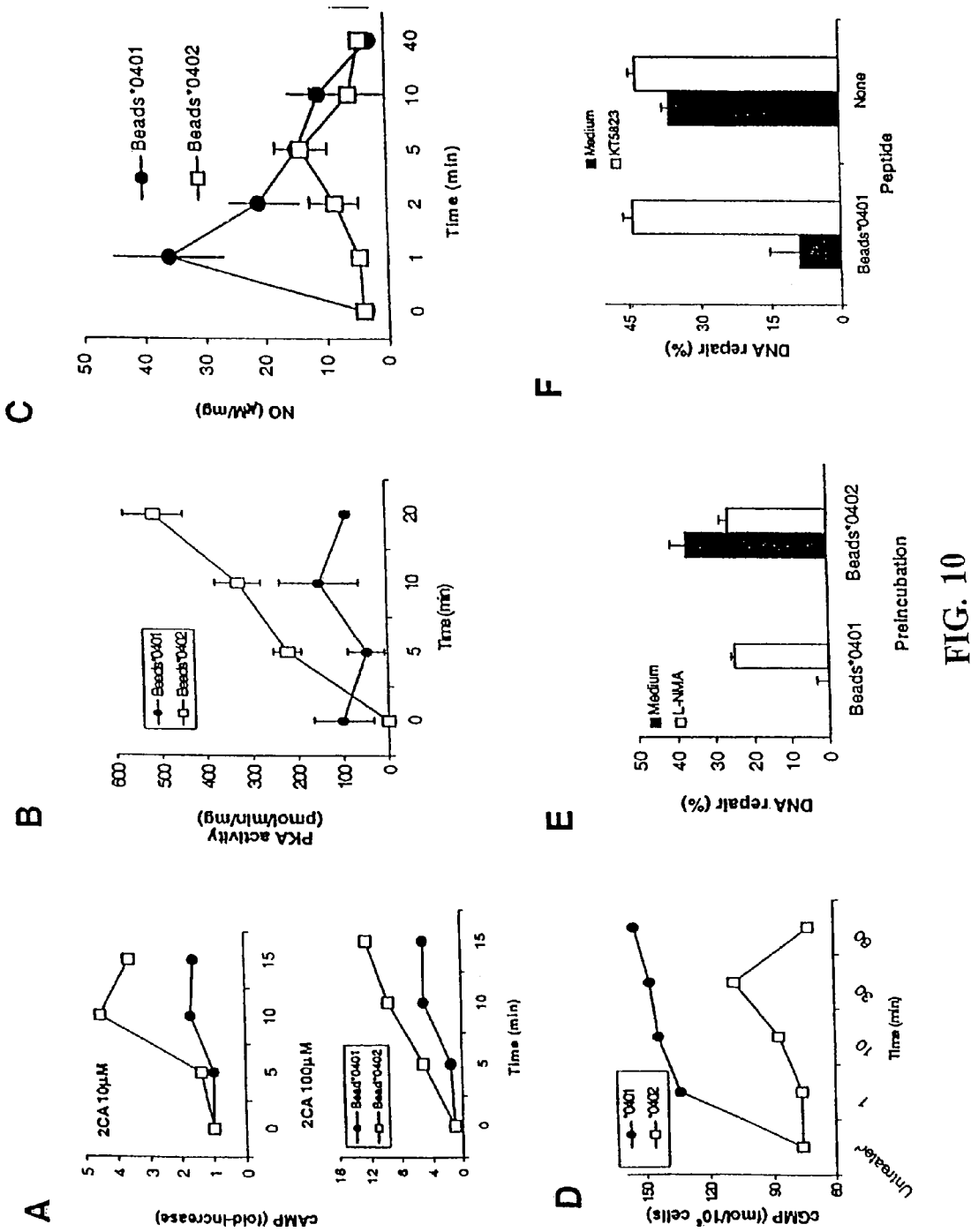

FIG. 10 presents a characterization of shared epitope-triggered intracellular signaling. FIG. 10A shows cAMP levels in the presence of different concentrations of 2CA and after preincubation with different peptide-conjugated beads. (FIG. 10A abbreviations; 2CA, 2-chloroadenosine; Bead*0401, peptide 65–79*0401 (corresponding to amino acids 65–79 of the β chain encoded by the HLA-DRB*0401 allele) chemically conjugated to Sepharose beads; Bead*0402, peptide 65–79*0402 (corresponding to amino acids 65–79 of the β chain encoded by the HLA-DRB*0402 allele) chemically conjugated to Sepharose beads; min, minutes; cAMP, cyclic AMP.) FIG. 10B shows PKA activity following preincubation with different peptide-conjugated beads. (FIG. 10B abbreviations: Bead*0401, peptide 65–79*0401 (corresponding to amino acids 65–79 of the β chain encoded by the HLA-DRB*0401 allele) chemically conjugated to Sepharose beads; Bead*0402, peptide 65–79*0402 (corresponding to amino acids 65–79 of the β chain encoded by the HLA-DRB*0402 allele) chemically conjugated to Sepharose beads; PKA, protein kinase A; min, minutes.) FIG. 10C shows NO levels following preincubation with different peptide-conjugated beads. (FIG. 10C. abbreviations; NO, nitric oxide; Bead*0401, peptide 65–79*0401 (corresponding to amino acids 65–79 of the β chain encoded by the HLA-DRB*0401 allele) chemically conjugated to Sepharose beads; Bead*0402, peptide 65–79*0402 (corresponding to amino acids 65–79 of the β chain encoded by the HLA-DRB*0402 allele) chemically conjugated to Sepharose beads; min, minutes.) FIG. 10D shows cGMP levels following exposure to different soluble peptides. (FIG. 10D abbreviations: *0401, soluble peptide 65–79*0401 (corresponding to amino acids 65–79 of the β chain encoded by the HLA-DRB*0401 allele) *0402, soluble peptide 65–79*0402 (corresponding to amino acids 65–79 of the β chain encoded by the HLA-DRB*0402 allele); cGMP, cyclic GMP; min, minutes.) FIG. 10E is a bar graph that shows DNA repair in cells exposed or not to L-NMA and different peptide-conjugated beads. (FIG. 10E abbreviations: Bead*0401, peptide 65–79*0401 (corresponding to amino acids 65–79 of the β chain encoded by the HLA-DRB*0401 allele) chemically conjugated to Sepharose beads; Bead*0402, peptide 65–79*0402 (corresponding to amino acids 65–79 of the β chain encoded by the HLA-DRB*0402 allele) chemically conjugated to Sepharose beads; L-NMA, $N^G$-monomeththyl-L-arginine.) FIG. 10F is a bar graph that shows DNA repair in cells preincubated or not with KT5823 and preincubated with different peptide-conjugated beads. (FIG. 10F abbreviations: Bead*0401, peptide 65–79*0401 (corresponding to amino acids 65–79 of the β chain encoded by the HLA-DRB*0401 allele) chemically conjugated to Sepharose beads; KT5823, a chemical inhibitor of protein kinase G.)

Figure 11B:
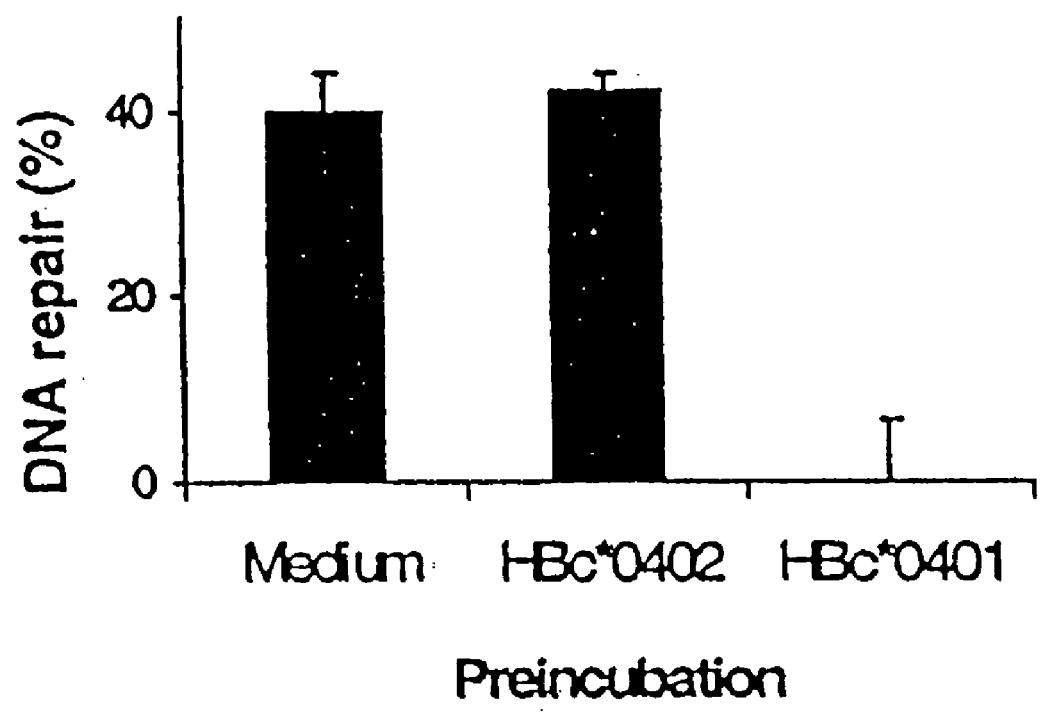

FIG. 11 shows the inhibition of cAMP signaling by shared epitope genetically inserted into foreign proteins. FIG. 11A (SEQ ID NOS: 17 and 18) shows the amino acid sequence of the recombinant HBc proteins containing residues 65–79 of DR.beta.*0401 and DR.beta.*0402. (FIG. 11A abbreviations: HBc*0401, a recombinant chimeric protein, consisted of hepatitis β core protein (HBc) with an insertion of a sequence corresponding to amino acids 65–79 of the β chain encoded by the HLA-DRB*0401 allele; HBc*0402, a recombinant chimeric protein, consisted of hepatitis B core protein (HBc) with an insertion of a sequence corresponding to amino acids 65–79 of the β chain encoded by the HLA-DRB*0402 allele.) FIG. 11B is a bar graph which shows DNA repair in M1 cells preincubated overnight with HBc*0401 or HBc*0404. (FIG. 11B abbreviations: HBc*0402, a recombinant chimeric protein, consisted of hepatitis B core protein (HBc) with an insertion of a sequence corresponding to amino acids 65–79 of the β chain encoded by the HLA-DRB*0402 allele; HBc*0401, a recombinant chimeric protein, consisted of hepatitis B core protein (HBc) with an insertion of a sequence corresponding to amino acids 65–79 of the β chain encoded by the HLA-DRB*0401 allele.)

FIG. 12 depicts the neuroprotective effect shared eptiope-containing peptides. (FIG. 12 abbreviations: 65–78*0401, synthetic peptide corresponding to amino acids 65–78 of the β chain encoded by the HLA-DRB*0401 allele; 65–78*0402, synthetic peptide corresponding to amino acids 65–78 of the β chain encoded by the HLA-DRB*0402 allele.) FIG. 12A depicts NG108-15 cells after 24 hours of incubation with peptide 65–78*0402. FIG. 12B depicts NG108-15 cells after 24 hours of incubation with peptide 65–78*0401. FIG. 12C is a bar graph that shows cell number and neurites in NG108-15 cells following exposure to different peptides.

Figure 13A:
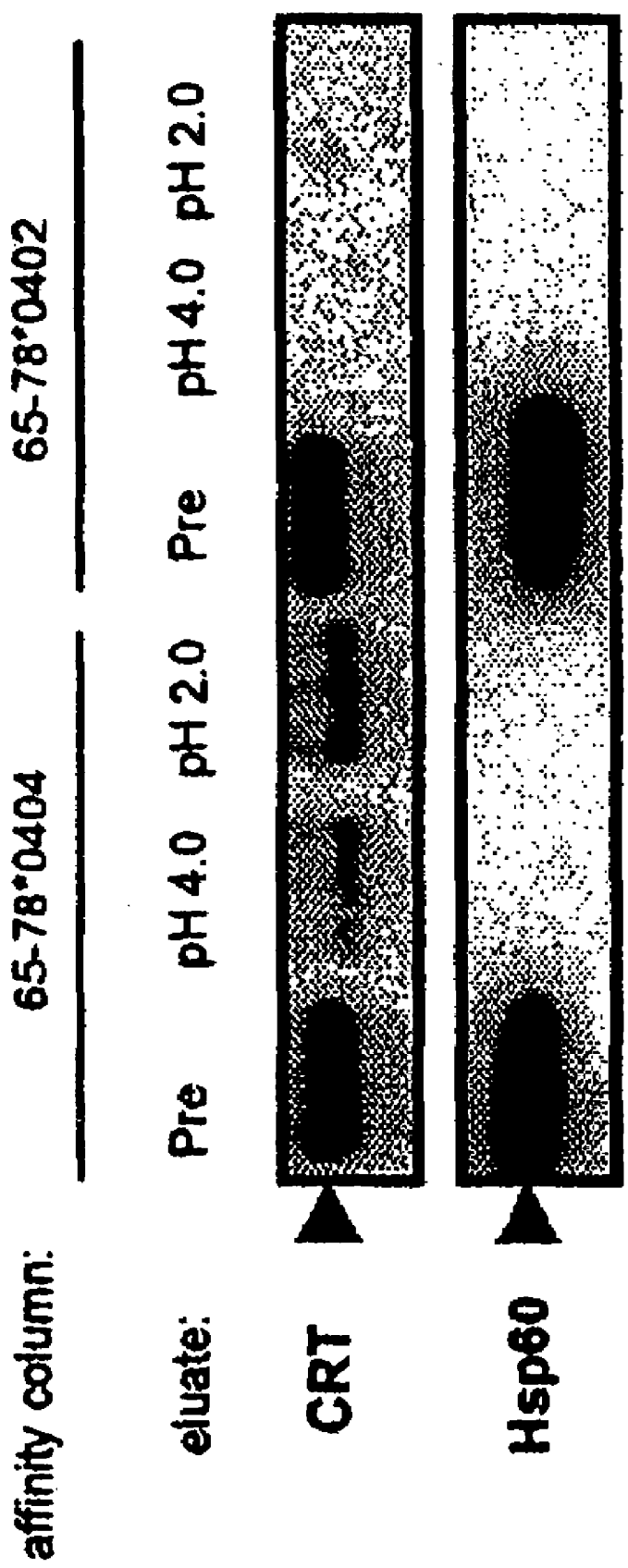
Figure 13B:
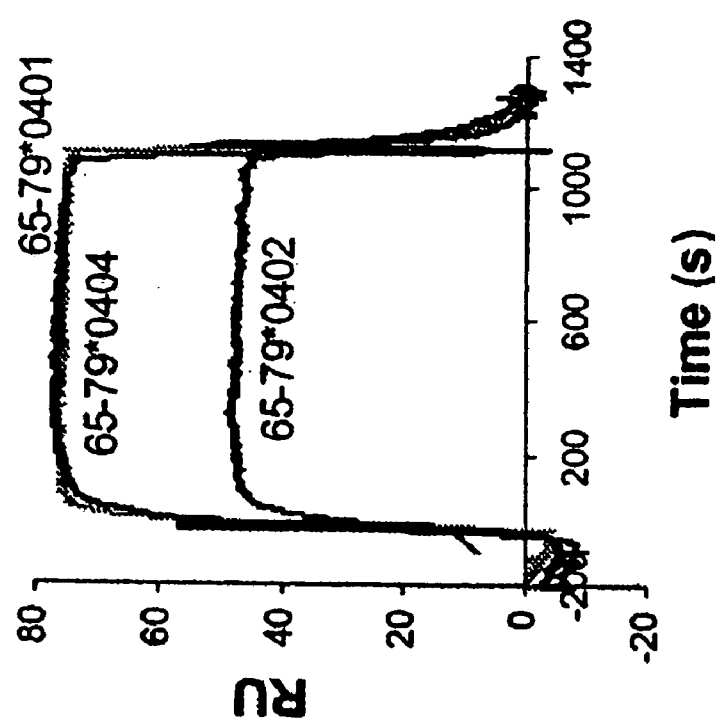
Figure 13C:
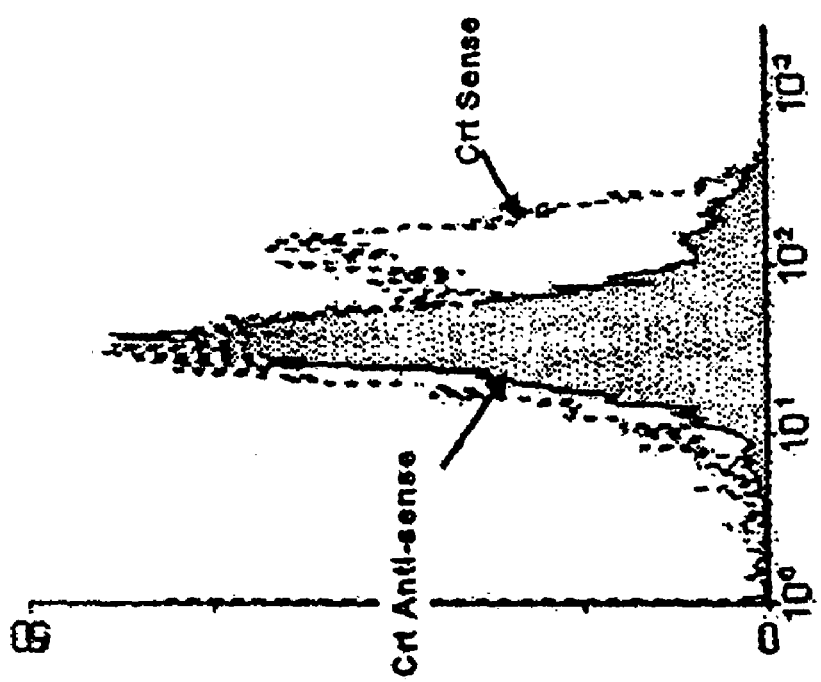
Figure 13D:
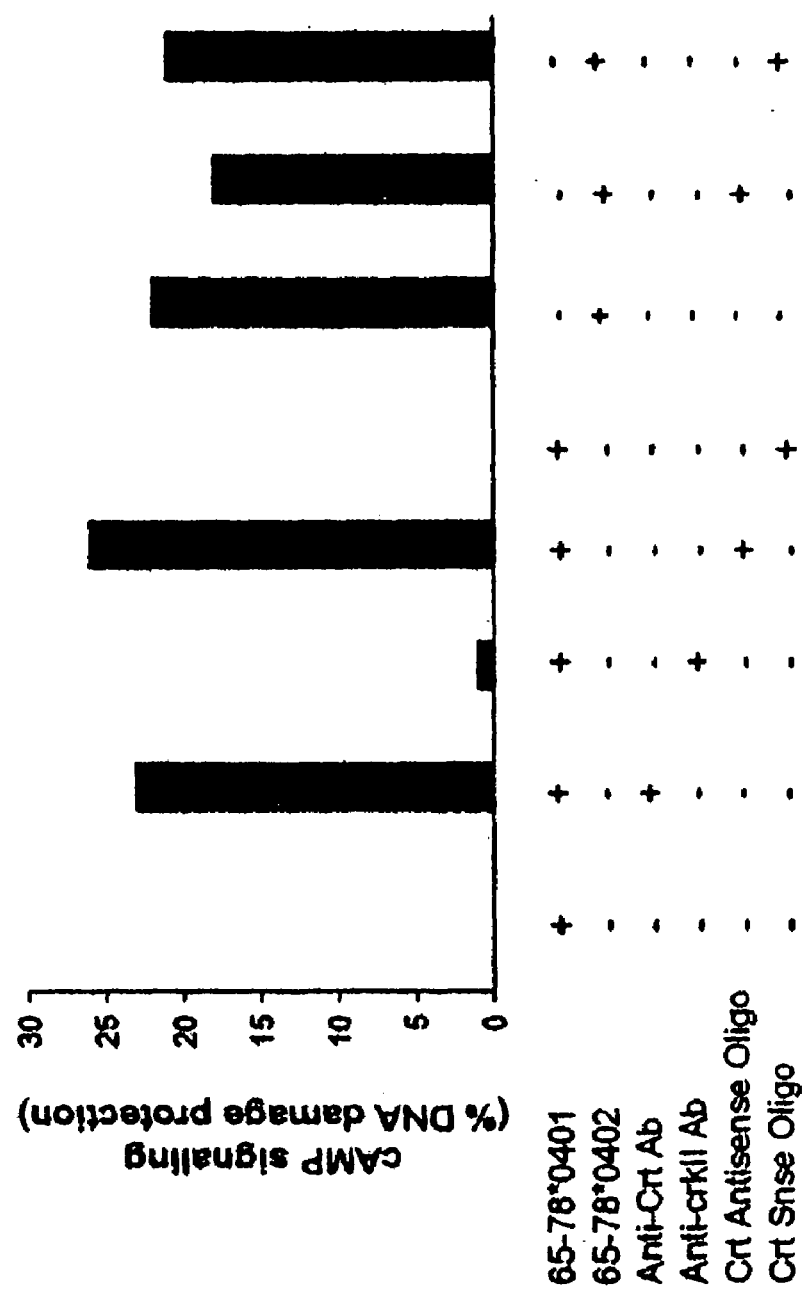

FIG. 13A–D presents data showing that shared epitope-containing peptides bind to and transduce signaling through the cell surface receptor; calreticulin. FIG. 13A shows immunoblots of recombinant human calreticulin and HSP60 (eluted from peptide affinity chromatography). (FIG. 13A abbreviations: 65–78*0404, synthetic peptide corresponding to amino acids 65–78 of the β chain encoded by the HLA-DRB*0404 allele; 65–78*0402, synthetic peptide corresponding to amino acids 65–78 of the β chain encoded by the HLA-DRB*0402 allele; CRT, calreticulin; Hsp60, human 65 kD heat shock protein.) FIG. 13B shows surface plasmon resonance profiles. (FIG. 13B abbreviations: 65–79*0401, synthetic peptide corresponding to amino acids 65–79 of the β chain encoded by the HLA-DRB*0401 allele; 65–79*0402, synthetic peptide corresponding to amino acids 65–79 of the β chain encoded by the HLA-DRB*0402 allele; 65–79*0404, synthetic peptide corresponding to amino acids 65–79 of the β chain encoded by the HLA-DRB*0404 allele; RU, response units; s, seconds.) FIG. 13C shows that calreticulin anti-sense oligonucleotides suppress calreticulin surface expression. (FIG. 13C abbreviations: Crt, calreticulin; Crt Anti-sense, cells transfected with Crt anti-sense oligonucleotides; Crt Sense, cells transfected with Crt sense oligonucleotides.) FIG. 13D shows that anti-calreticulin antibodies and anti-sense oligonucleotides block the cAMP-inhibitory effect of shared epitope-containing peptides. (FIG. 13D abbreviations: 65–78*0401, synthetic peptide corresponding to amino acids 65–78 of the β chain encoded by the HLA-DRB*0401 allele; 65–78*0402, synthetic neptide corresponding to amino acids 65–78 of the β chain encoded by the HLA-DRB*0402 allele; Crt, calreticulin; Ab, antibody; crkII, control antibody; Crt Antisense Oligo, cells transfected with Crt anti-sense oligonucleotides; Crt Sense Oligo, cells transfected with Crt sense oligonucleotides.)

FIG. 14 ([SEQ ID NO: 29]) projects the amino acid sequence of the recombinantly produced calreticulin referenced in the instant application.

Figure 15:
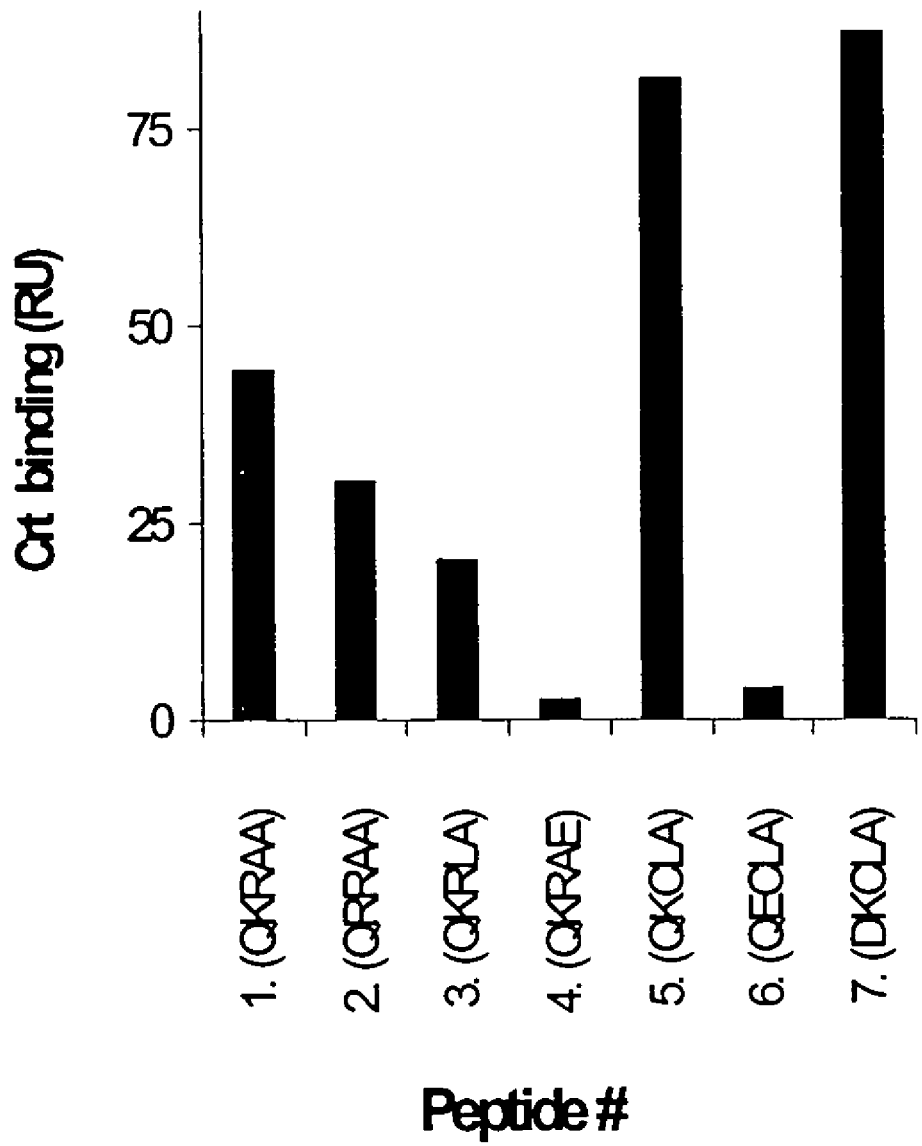

FIG. 15 depicts specific binding between recombinant calreticulin immobilized on a CM5 biosensor chip (Biacore) and shared epitope pentapeptides. (FIG. 15 abbreviations: Crt, calreticulin; RU, response units).

FIG. 16 shows competitive inhibition of shared epitope-calreticulin binding by peptide DKCLA. (FIG. 16 abbreviation: RU, response units.) FIG. 16A and FIG. 16B show that binding of 14-mer, shared epitope-expressing peptides 65–78*0401 (the synthetic peptide corresponding to amino acids 65–78 of the β chain encoded by the HLA-DRB*0401 allele) (FIG. 16A) and 65–78*0404 (the synthetic peptide corresponding to amino acids 65–79 of the β chain encoded by the HLA-DRB*0404 allele) (FIG. 16B) to calreticulin is inhibited by peptide DKCLA. FIG. 16C and FIG. 16D show dose-response analysis of the inhibitory effect of DKCLA on calreticulin binding of 14-mer peptides 65–78*0401 (FIG. 16C) and 65–78*0404 (FIG. 16D).

Figure 17:
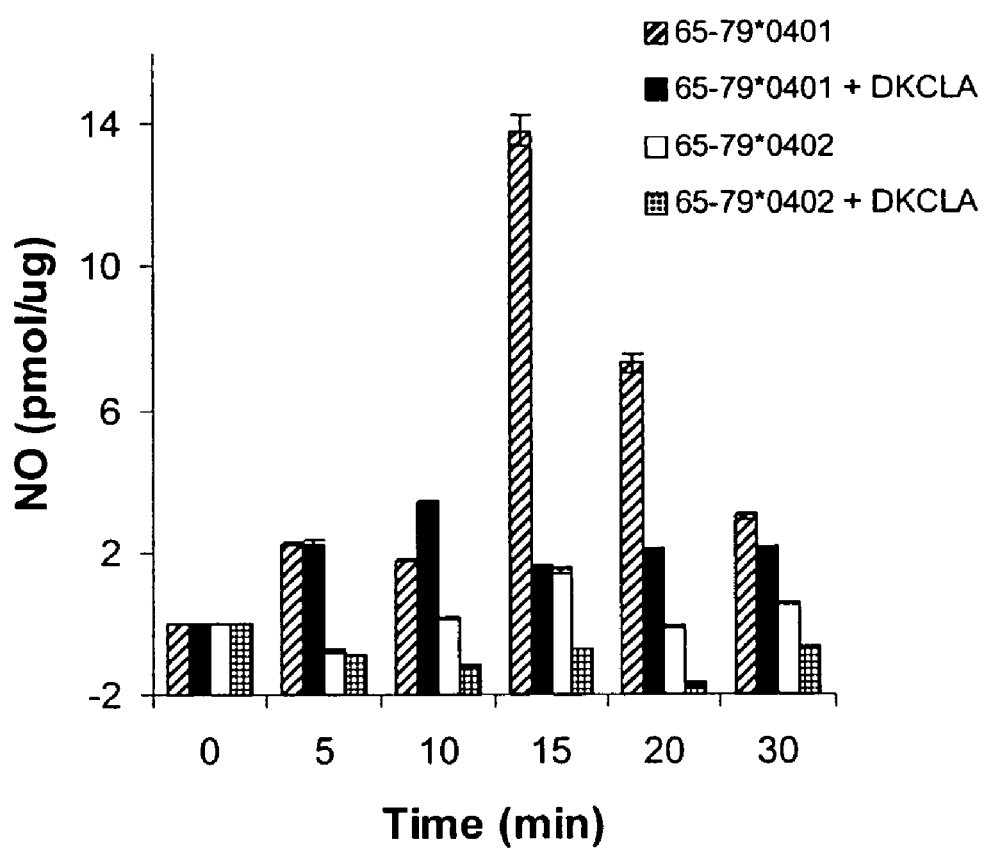

FIG. 17 shows that DKCLA blocks shared epitope-induced signaling in M1 cells incubated overnight with DKCLA and subsequently stimulated with Sepharose bead-coated peptide 65–79*0401 (hatched bars) or the control peptide, 65–79*0402 (open bars). (FIG. 17 abbreviations: 65–79*0401, synthetic peptide corresponding to amino acids 65–79 of the β chain encoded by the HLA-DRB*0401 allele; 65–79*0402, synthetic peptide corresponding to amino acids 65–79 of the β chain encoded by the HLA-DRB*0402 allele; NO, nitric oxide; min, minutes)

DEFINITIONS

As used herein, "one or more symptoms of Alzheimer's disease" (AD; Alzheimer's disease) can be grouped into symptoms at three stages of the disease. Mild symptoms include confusion and memory loss, disorientation (getting lost in familiar surroundings), problems with routine tasks and changes in personality and judgement. Moderate symptoms include difficulty with activities of daily living (such as feeding and bathing), anxiety, suspiciousness, agitation, sleep disturbances, wandering, pacing and difficulty recognizing family and friends. Severe symptoms include loss of speech, loss of appetite and weight, loss of bladder and bowel control and total dependence on the caregiver.

As used herein, "one or more signs or symptoms of rheumatoid arthritis" (RA; rheumatoid arthritis) include tender, warm, swollen joints, usually affected in a symmetrical pattern. Other symptoms of rheumatoid arthritis include fatigue and occasional fever or malaise. Pain and stiffness lasting more than 30 minutes in the morning or after a long rest are also common symptoms of rheumatoid arthritis. As used herein, "improved" means a reduction in the severity of the signs or symptoms of rheumatoid arthritis and a return towards normal function.

As used herein, "treatment" refers to a reduction of signs or symptoms, or to a reduction of side effects. Symptoms are "reduced" when the magnitude (e.g. intensity) or frequency of symptoms is reduced. In the case of AD, symptoms are reduced when (for example) the subject experiences an improvement in memory, experiences fewer episodes of disorientation, is better able to recognize family and friends and/or is more easily able to perform routine tasks and is less reliant on the caregiver. In the case of RA, symptoms are reduced when the subject experiences less pain, a shorter duration of morning joint stiffness, and less swelling in the affected joints. It is not intended that the present invention be limited only to cases where the symptoms are eliminated. The present invention specifically contemplates treatment such that symptoms are reduced (and the condition of the subject is thereby "improved"), albeit not completely eliminated.

As used herein, "shared epitope-containing peptides" are peptides which comprise the amino acid sequence QKRAA [Gln Lys Arg Ala Ala] [SEQ ID NO: 1] or QRRAA [Gln Arg Arg Ala Ala] [SEQ ID NO: 2]. Shared epitope-containing peptides can be pentapeptides or longer peptides. Shared epitope-containing peptides can range in length from five to hundreds of amino acids. In some embodiments, shared epitope-containing peptides are 15 amino acids in length (for example, the peptides defined by SEQ ID NOs: 5 and 10). In other embodiments, shared epitope-containing peptides are 14 amino acids in length (for example, SEQ ID NO: 6). In yet other embodiments, shared epitope-containing peptides are between five and 75 amino acids in length. "shared epitope motif-containing peptides" comprise amino acid sequences defined by the consensus Q(K/R)XXA [Gln (Lys/Arg) Xaa Xaa Ala; wherein Xaa represents any amino acid] sequence [SEQ ID NO: 3]. Shared epitope motif-containing peptides can be pentapeptides or longer peptides. Shared epitope motif-containing peptides can range in length from five to hundreds of amino acids. In preferred embodiments, shared epitope motif-containing peptides are between five and twenty amino acids in length, and even more preferably, between five and fifteen amino acids in length. In other embodiments, shared epitope motif-containing peptides are between five and 75 amino acids in length.

As used herein, "derivatives" or "analogues" of shared epitope-containing or shared epitope motif-containing peptides can refer to a number of alterations in such peptides. In some embodiments, the derivatives comprise peptides with amino acid sequence changes. Such changes can be conservative amino acid substitutions amino acid deletions or amino acid insertions, provided that the shared epitope or shared epitope motif activity is substantially (50% or greater) retained. Analogues have amino acid analogues in place of the corresponding natural amino acids. Examples of such analogues include (but are not limited to) p-fluorophenylalanine (an analogue of phenylalanine) and ethionine and norleucine. Analogues also include incorporation of D-amino acids at particular points along the peptide chain. Derivatives and analogues may be conjugated (see below).

As used herein "protease resistant peptides" refers to peptides with a reduced susceptibility to protease digestion. For example, a protease resistant peptide may comprise a protecting group, or may comprise at least one D-amino acid. It is not intended that the present invention be limited to complete protease resistance. It is enough if susceptibility to protease digestion is reduced.

As used herein, "antagonists" of shared epitope or shared epitope motif-containing peptides refers to molecules or compounds which are "inhibitory" to shared epitope or shared epitope motif-containing peptides. Shared epitope peptide antagonists may be peptides, for example shared epitope antagonist-containing peptides, or non-peptide compounds. Antagonists may or may not be homologous to the native compound that they inhibit with respect to conformation, charge or other characteristics. Thus, antagonists may be recognized by the same or different receptors that are recognized by the natural compound. Antagonists may have direct inhibitory activity on receptors by which they are recognized, or they may bind with high affinity to receptors by which they are recognized but lack specific activity, thereby blocking access to the receptor of other molecules or compounds. Shared epitope- or shared epitope motif-containing antagonists are contemplated to be useful in the treatment of diseases which have signal transduction aberrations comprising reduced cAMP-mediated signaling or over-active NO-mediated signaling (see Tables 1 and 2). Rheumatoid arthritis is one example of such a disease.

As used herein, "conjugates" of shared epitope or shared epitope motif-containing peptides, peptide derivatives, analogues or antagonists refers to such peptides with a moiety linked to said peptide. In some embodiments, said linkage is to the N- or C-terminus, or both, of the peptide. In some embodiments, conjugation is achieved through the introduction of a cysteine into the peptide. While the cysteine can be added at the N or C termini, it can also be introduced into the middle of the motif. In some embodiments, the conjugate comprises linkage of a lipophilic or hydrophobic moiety. In some embodiments, the conjugate comprises linkage of a carrier molecule, including but not limited to an antibody. The linkage between the peptide and the moiety can be a direct chemical linkage, or the linkage can be through a linking agent, such as a cross-linker.

As used herein, "signal transduction aberrations" include (but are not limited to) over-activity or reduced activity of the cAMP-mediated, and NO-mediated intracellular signaling pathways. Signal transduction aberrations also include disruptions in the balance between signaling pathways, such as the cAMP- and NO-mediated pathways. Signal transduction aberrations can also include alterations to intercellular signaling pathways.

As used herein, "diseases with underlying signal transduction aberrations" include, but are not limited to those diseases listed in Tables 1 and Tables 2. In such diseases, intercellular and intracellular signal transduction aberrations may underlie the pathogenesis of the disease.

As used herein, "synthetic peptide" refers to a peptide made by chemical or enzymatic synthetic procedures well known in the art. Synthetic shared epitope- and shared epitope motif-containing peptides, derivatives, analogues and mimetics are contemplated.

As used herein, "protecting groups" are those groups that prevent undesirable reactions (such as proteolysis) involving unprotected functional groups. Protecting groups can be added to the N-terminus, C-terminus or both of an shared epitope-containing or shared epitope motif-containing peptide. In one embodiment, the present invention contemplates that the protecting group is an acyl or an amide. In one embodiment, the acyl is acetate. In another embodiment, the protecting group is a benzyl group. In another embodiment, the protecting group is a benzoyl group. The present invention also contemplates combinations of such protecting groups.

As used herein, "biological activity" of shared epitope- or shared epitope motif-containing peptides, derivatives or analogues, mimetics and antagonists refers to the ability of said peptides, derivatives or analogues, mimetics and antagonists to modulate signal transduction pathways. Such activity can be assayed by a number of means. For example, biological activity can be assayed in an in vitro cAMP-mediated assay for DNA repair following induction of DNA damage. Shared epitope-containing peptides inhibit DNA repair in such an assay. Biological activity of such peptides can also be determined by measuring intracellular cAMP levels or protein kinase A activation following application of said peptides to cells.

As used herein, "calreticulin" is a ubiquitous multifunctional calcium-binding protein. As used herein, a "calreticulin antagonist compound" is a compound that antagonizes the biological activity of calreticulin. In one embodiment, the calreticulin antagonist compound is a shared epitope antagonist-containing pepetide. In a further embodiment, the calreticulin antagonist compound is an anti-calreticulin antibody. In another embodiment, the calreticulin antagonist compound is an anti-calreticulin antisense oligonucleotide compound. In a still further embodiment, the calreticulin antagonist compound is a small interfering RNA duplex, or vectors encoding said small interfering RNA duplex.

As used herein, the "N-terminus" of a peptide refers to the end of the peptide with a free amino group. Note that the N-terminus amino group does not necessarily have to be "free", for example, it may be involved in linking of moieties to the N-terminus in conjugates.

As used herein, the "C-terminus" of a peptide refers to the end with a free carboxyl group. Note that the C-terminus carboxyl group does not necessarily have to be "free", for example, it may be involved in linking moieties to the C-terminus in conjugates.

As used herein, a "carrier molecule" refers to a moiety used to facilitate transport of compounds of the invention (for example, shared epitope antagonist-containing peptides) to synovial tissue. The carrier molecule can be directly linked to the compounds of the invention, linked by a cross-linker or physically associated with the compounds of the invention. Carrier molecules include, but are not limited to, lipophilic or hydrophobic moieties, antibodies (and fragments thereof) or other molecules (such as polyamines, including but not limited to spermine).

As used herein, an "antibody" is a molecule produced by specific cells of the immune system. An antibody specifically recognizes and binds to another compound. The present invention contemplates the use of both polyclonal and monoclonal antibodies (and fragments thereof).

As used herein, "subject" refers to a human or animal.

As used herein, "HLA-DR4", or "DR4" refers to a particular human leukocyte antigen (HLA or major histocompatibility complex (MHC) antigen), as determined serologically. The DR4 antigen is associated with the DR locus B1β chain ("DRB1"). Multiple alleles of DRB1 are associated with the DR4 antigen. For example, DRB1*0401 and DRB1*0402 refer to the alleles, while the corresponding β chains are referred to as DRβ*0401 and DRβ*0402, respectively.

As used herein, "single dosage" refers to a pharmaceutical composition of a formulation that is capable of achieving its intended effect in a single application or administration (e.g. once a day).

As used herein, "oral administration" or "orally" refers to the introduction of a pharmaceutical composition into a subject by way of the oral cavity (e.g., in aqueous liquid or solid form).

As used herein, "sublingual administration" or "sublingually" refers to the introduction of a pharmaceutical composition into a subject by application to the mucosal surface under the tongue (within the oral cavity) such that the composition is absorbed into the subject.

As used herein, "buccal administration" or "buccal" refers to the introduction of a pharmaceutical composition into a subject by application to the mucosal surface lining the cheek (within the oral cavity) such that the composition is absorbed into the subject.

As used herein, "intranasal administration" or "intranasally" refers to the introduction of a pharmaceutical composition within the nasal cavity.

As used herein, "respiratory inhalation" refers to the introduction of a pharmaceutical composition within the respiratory tract.

As used herein, "intrapulmonary delivery" refers comprises administration to the lung. Intrapulmonary delivery of pharmacologic agents to patients can be accomplished via aerosolization. Alternatively, the agent may be administered to the lung through a bronchoscope.

As used herein, "transdermal administration" or "transdermally" or "cutaneously" refers to the introduction of a pharmaceutical composition into a subject by application to the surface of the skin such that the composition is absorbed into the subject.

As used herein, "injection" or "standard injection" refers to the placement of a pharmaceutical composition into a subject (e.g., with a hypodermic needle). For example, such injection can be made subcutaneously, intravenously, intramuscularly, intracavemosally, etc.

As used herein, "intra-articular" injection refers to direct injection of a pharmaceutical composition into a joint (for example, in a method of treatment of rheumatoid arthritis).

As used herein, "genoprotective" refers to protection of DNA from damage, for example, a signal that protects DNA from oxidative damage is genoprotective.

As used herein, "oxidative damage" to DNA refers to modifications in DNA including base and sugar lesions, strand breaks, DNA-protein cross-links, covalent modifications, and base-free sites caused by oxygen-derived, free radical reactive oxygen species (ROS) including, for example, superoxide radical $O2^-$, hydroxy radical $OH^-$, hydrogen peroxide $H_2O_2$, and peroxynitrite.

As used herein, "oxidative stress" refers to the condition of increased ROS production in cells resulting in cellular degeneration. As used herein, "pro-oxidative" refers to ROS production. As used herein, "anti-oxidative" refers to inhibition of ROS formation.

The term "gene" refers to a nucleic acid (e.g., DNA) sequence that comprises coding sequences necessary for the production of a polypeptide, RNA (e.g., including but not limited to, mRNA, tRNA and rRNA) or precursor (e.g., calreticulin). The polypeptide, RNA, or precursor can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In particular, the term "calreticulin gene" refers to the full-length calreticulin nucleotide sequence (e.g., contained in SEQ ID NO: 1). However, it is also intended that the term encompass fragments of the calreticulin sequence, mutants as well as other domains within the full-length calreticulin nucleotide sequence. Furthermore, the terms "calreticulin nucleotide sequence" or "calreticulin polynucleotide sequence" encompasses DNA, cDNA, and RNA (e.g., mRNA) sequences.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified," "mutant," "polymorphism," and "variant" refer to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or, in other words, the nucleic acid sequence that encodes a gene product. The coding region may be present in a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "complementary" or "complementarity" are used in reference to polynucleotides (i.e., a sequence of nucleotides) related by the base-pairing rules. For example, for the sequence 5'-"A-G-T-3'," is complementary to the sequence 3'-"T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "competes for binding" is used in reference to a first polypeptide with an activity which binds to the same substrate as does a second polypeptide with an activity, where the second polypeptide is a variant of the first polypeptide or a related or dissimilar polypeptide. The efficiency (e.g., kinetics or thermodynamics) of binding by the first polypeptide may be the same as or greater than or less than the efficiency substrate binding by the second polypeptide. For example, the equilibrium binding constant ($K_D$) for binding to the substrate may be different for the two polypeptides. The term "$K_m$" as used herein refers to the Michaelis-Menton constant for an enzyme and is defined as the concentration of the specific substrate at which a given enzyme yields one-half its maximum velocity in an enzyme catalyzed reaction.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m = 81.5 + 0.41(\% \text{ G+C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85–100% identity, preferably about 70–100% identity). With medium stringency conditions, nucleic acid base pairing will occur between nucleic acids with an intermediate frequency of complementary base sequences (e.g., hybridization under "medium stringency" conditions may occur between homologs with about 50–70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42 C in a solution consisting of 5×SSPE (43.8 g/l NaCl, 6.9 g/l NaH$_2$PO$_4$ H$_2$O and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0× SSPE, 1.0% SDS at 42 C when a probe of about 500 nucleotides in length is employed.

"Medium stringency conditions" when used in reference to nucleic acid hybridization comprise conditions equivalent to binding or hybridization at 42 C in a solution consisting of 5×SSPE (43.8 g/l NaCl, 6.9 g/l NaH$_2$PO$_4$ H$_2$O and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0× SSPE, 1.0% SDS at 42 C when a probe of about 500 nucleotides in length is employed.

"Low stringency conditions" comprise conditions equivalent to binding or hybridization at 42 C in a solution consisting of 5×SSPE (43.8 g/l NaCl, 6.9 g/l NaH$_2$PO$_4$ H$_2$O and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42 C when a probe of about 500 nucleotides in length is employed. The present invention is not limited to the hybridization of probes of about 500 nucleotides in length. The present invention contemplates the use of probes between approximately 10 nucleotides up to several thousand (e.g., at least 5000) nucleotides in length.

One skilled in the relevant understands that stringency conditions may be altered for probes of other sizes (See e.g., Anderson and Young, Quantitative Filter Hybridization, in *Nucleic Acid Hybridization* [1985] and Sambrook et al., Molecular Cloning: A Laboratory Manual, Cold Spring Harbor Press, NY [1989]).

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman [Smith and Waterman, *Adv. Appl. Math.* 2: 482 (1981)] by the homology alignment algorithm of Needleman and Wunsch [Needleman and Wunsch, *J. Mol. Biol.* 48:443 (1970)], by the search for similarity method of Pearson and Lipman [Pearson and Lipman, *Proc. Natl. Acad. Sci.* (*U.S.A.*) 85:2444 (1988)], by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention (e.g., calreticulin).

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine; leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions (claimed in the present invention) with its various ligands and/or substrates.

The term "polymorphic locus" is a locus present in a population that shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

As used herein, the term "genetic variation information" or "genetic variant information" refers to the presence or absence of one or more variant nucleic acid sequences (e.g., polymorphism or mutations) in a given allele of a particular gene (e.g., the calreticulin gene).

As used herein, the term "detection assay" refers to an assay for detecting the presence of absence of variant nucleic acid sequences (e.g., polymorphism or mutations) in a given allele of a particular gene (e.g., the calreticulin gene).

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (D. L. Kacian et al., *Proc. Natl. Acad. Sci. USA* 69:3038 [1972]). Other nucleic acids will not be replicated by this amplification enzyme. Similarly, in the case of T7 RNA polymerase, this amplification enzyme has a stringent specificity for its own promoters.(Chamberlin et al., *Nature* 228:227 [1970]). In the case of T4 DNA ligase, the enzyme will not ligate the two oligonucleotides or polynucleotides, where there is a mismatch between the oligonucleotide or polynucleotide substrate and the template at the ligation junction (D. Y. Wu and R. B. Wallace, *Genomics* 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," refers to a nucleic acid sequence or structure to be detected or characterized. Thus, the "target" is sought to be sorted out from other nucleic acid sequences. A "segment" is defined as a region of nucleic acid within the target sequence.

As used herein, the term "polyrnerase chain reaction" ("PCR") refers to the method of K. B. Mullis U.S. Pat. Nos. 4,683,195, 4,683,202, and 4,965,188, hereby incorporated by reference, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule that is comprised of segments of DNA joined together by means of molecular biological techniques.

As used herein, the term "antisense" is used in reference to RNA sequences that are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter that permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding calreticulin includes, by way of example, such nucleic acid in cells ordinarily expressing calreticulin where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein, a "portion of a chromosome" refers to a discrete section of the chromosome. Chromosomes are divided into sites or sections by cytogeneticists as follows: the short (relative to the centromere) arm of a chromosome is termed the "p" arm; the long arm is termed the "q" arm. Each arm is then divided into 2 regions termed region 1 and region 2 (region 1 is closest to the centromere). Each region is further divided into bands. The bands may be further divided into sub-bands. For example, the 11p15.5 portion of human chromosome 11 is the portion located on chromosome 11 (11) on the short arm (p) in the first region (1) in the 5th band (5) in sub-band 5 (0.5). A portion of a chromosome may be "altered;" for instance the entire portion may be absent due to a deletion or may be rearranged (e.g., inversions, translocations, expanded or contracted due to changes in repeat regions). In the case of a deletion, an attempt to hybridize (i.e., specifically bind) a probe homologous to a particular portion of a chromosome could result in a negative result (i.e., the probe could not bind to the sample containing genetic material suspected of containing the missing portion of the chromosome). Thus, hybridization of a probe homologous to a particular portion of a chromosome may be used to detect alterations in a portion of a chromosome.

The term "sequences associated with a chromosome" means preparations of chromosomes (e.g., spreads of metaphase chromosomes), nucleic acid extracted from a sample containing chromosomal DNA (e.g., preparations of genomic DNA); the RNA that is produced by transcription of genes located on a chromosome (e.g., hnRNA and mRNA), and cDNA copies of the RNA transcribed from the DNA located on a chromosome. Sequences associated with a chromosome may be detected by numerous techniques including probing of Southern and Northern blots and in situ hybridization to RNA, DNA, or metaphase chromosomes with probes containing sequences homologous to the nucleic acids in the above listed preparations.

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein the term "coding region" when used in reference to structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets, which specify stop codons (i.e., TAA, TAG, TGA).

As used herein, the term "purified" or "to purify" refers to the removal of contaminants from a sample. For example, calreticulin antibodies are purified by removal of contaminating non-immunoglobulin proteins; they are also purified by the removal of immunoglobulin that does not bind calreticulin. The removal of non-immunoglobulin proteins and/or the removal of immunoglobulins that do not bind calreticulin results in an increase in the percent of calreticulin-reactive immunoglobulins in the sample. In another example, recombinant calreticulin polypeptides are expressed in bacterial host cells and the polypeptides are purified by the removal of host cell proteins; the percent of recombinant calreticulin polypeptides is thereby increased in the sample.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four consecutive amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., *Molecular Cloning: A Laboratory Manual*, Cold Spring Harbor Press, NY, pp 9.31–9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39–7.52 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "transgene" as used herein refers to a foreign, heterologous, or autologous gene that is placed into an organism by introducing the gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene. The term "autologous gene" is intended to encompass variants (e.g., polymorphisms or mutants) of the naturally occurring gene. The term transgene thus encompasses the replacement of the naturally occurring gene with a variant form of the gene.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "host cell" refers to any eukaryotic or prokaryotic cell (e.g., bacterial cells such as $E.$ $coli$, yeast cells, mammalian cells, avian cells, amphibian cells, plant cells, fish cells, and insect cells), whether located in vitro or in vivo. For example, host cells may be located in a transgenic animal.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis (See, Example 10, for a protocol for performing Northern blot analysis). Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the RAD50 mRNA-specific signal observed on Northern blots). The amount of mRNA present in the band corresponding in size to the correctly spliced calreticulin transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, $Virol.$, 52:456 [1973]), has been modified by several groups to optimize conditions for particular types of cells. The art is well aware of these numerous modifications.

A "composition comprising a given polynucleotide sequence" as used herein refers broadly to any composition containing the given polynucleotide sequence. The composition may comprise an aqueous solution. Compositions comprising polynucleotide sequences encoding calreticulin or fragments thereof may be employed as hybridization probes. In this case, the calreticulin encoding polynucleotide sequences are typically employed in an aqueous solution containing salts (e.g., NaCl), detergents (e.g., SDS), and other components (e.g., Denhardt's solution, dry milk, salmon sperm DNA, etc.).

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the term "response," when used in reference to an assay, refers to the generation of a detectable signal (e.g., accumulation of reporter protein, increase in ion concentration, accumulation of a detectable chemical product).

As used herein, the term "reporter gene" refers to a gene encoding a protein that may be assayed. Examples of reporter genes include, but are not limited to, luciferase (See, e.g., deWet et al., *Mol. Cell. Biol.* 7:725 [1987] and U.S. Pat. Nos., 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

DESCRIPTION OF THE INVENTION

A. Signaling Pathways

Over the past decade it has become increasingly apparent that intercellular and intracellular signal transduction aberrations may underlie the pathogenesis of many diseases. Consequently, attempts to target such signaling abnormalities have become a common theme in the design of new therapeutic strategies [Reviewed in Levitzki A. *Curr Opin Cell Biol* 8:239–244 (1996)]). The methods and compositions of the present invention allow for modulation of the balance between two antagonistic signaling pathways, mediated, respectively, by cyclic adenosine 3',5' monophosphate (cAMP) and nitric oxide (NO).

The cAMP-mediated pathway [reviewed in Antoni F A. *Front Neuroendocrinol* 21:103–132 (2000)] is involved in a myriad of important physiologic functions in the immune, cardiovascular, endocrine and nervous systems, to mention only a few. Diminished or excessive activation of this pathway may result in various pathologies, as exemplified by the list of disorders shown in Table 1. For instance, over-activity of the cAMP-PKA pathway has been implicated in the pathogenesis of polycystic kidney disease, idiopathic nephrotic syndrome, HIV-induced T cell anergy, non-autoimmune hyperthyroidism, prostate cancer, pre-malignant breast pathology, dopamine-induced motor disorder, obesity, arrhythmia and Alzheimer's disease (AD, see below). Conversely, blunted cAMP responses have been observed in a number of inflammatory or autoimmune conditions, such as systemic lupus erythematosus, psoriasis, asthma, glomerulonephritis, atopic dermatitis and rheumatoid arthritis (RA, see below).

NO is a ubiquitous second messenger with a wide range of effects in many tissues, in particular, the cardiovascular, endothelial, immune and the central nervous systems. Many pathological states have been attributed to aberrations in the NO system (Table 2). For example, elevated NO levels are found in inflammatory and autoimmune diseases, such as inflammatory bowel disease, infectious diseases and various experimental models of autoimmunity. Elevated NO levels have been also implicated in the pathogenesis of osteoarthritis, septic shock, and uremia. On the other hand, inadequate levels of NO have been implicated in the pathogenesis of atherosclerosis, AD (see below), pulmonary hypertension, re-stenosis, insulin resistance syndrome, ischemia-reperfusion injury, congestive heart failure, non-steroidal (NSAID)-associated gastrointestinal (GI) toxicity and, possibly, acute respiratory distress syndrome.

It is noteworthy that the NO and cAMP signaling pathways interact at different levels. For example, cAMP can either inhibit or stimulate inducible NO synthase (NOS2), depending on the cell type. While in hepatocytes, astrocytes and glial cells, cAMP-elevating agents almost invariably suppress NOS2 expression, the opposite outcome has been observed in aortic smooth muscle cells, cardiac myocytes, mesangial cells adipocytes and endothelial cells [Galena E and Feinstein DL. *FASEB J* 13:2125–2137 (1999)]. Conversely, NO can inhibit cAMP signaling either by suppressing adenylate cyclase, or by activation of soluble guanylate cyclase [Denninger J W and Marletta M A. *Biochim Biophys Acta* 1411:334–350 (1999)], with resultant increase in cyclic guanosine monophosphate (cGMP) levels, which in turn can facilitate cAMP degradation by activating phosphodiesterases.

TABLE 1

Examples of Disease-Associated Signal Transduction Abnormalities in the cAMP-PKA Pathway

| SIGNALING ABERRATION | DISEASE |
|---|---|
| Over Activity: | Alzheimer's disease |
|  | arrhythmia |
|  | dopamine-induced motor disorder |
|  | HIV-induced T cell anergy |
|  | idiopathic nephrotic syndrome |
|  | non-autoimmune hyperthyroidism |
|  | obesity |
|  | polycystic kidney disease |
|  | pre-malignant breast pathology |
|  | prostate cancer |
| Reduced Activity: | asthma |
|  | atopic dermatitis |
|  | glomerulonephritis |
|  | psoriasis |
|  | rheumatoid arthritis |
|  | systemic lupus erythematosus |

TABLE 2

Examples of Disease-Associated Signal Transduction Abnormalities in the NO-cGMP Pathway

| SIGNALING ABERRATION | DISEASE |
|---|---|
| Over Activity: | experimental models of autoimmunity |
|  | infectious diseases |
|  | inflammatory bowel disease |
|  | osteoarthritis |
|  | septic shock |
|  | uremia |
| Reduced Activity: | acute respiratory distress syndrome |
|  | Alzheimer's Disease |
|  | atherosclerosis |
|  | congestive heart failure |
|  | insulin resistance syndrome |
|  | ischemia-reperfusion injury |
|  | NSAID GI toxicity |
|  | pulmonary hypertension |
|  | re-stenosis |

B. Subjects to be Treated

The utility of the present invention relates to many disease states caused by signaling aberrations, as exemplified in Tables 1 and 2. For the purposes of illustration, and not to be construed as limiting, the potential utility of the invention will be discussed in the context of Alzheimer's disease (AD) and rheumatoid arthritis (RA).

1. Alzheimer's Disease

AD is a common neurodegenerative disease, accounting for 50–70% of all cases of dementia. Clinically, the disease is characterized by insidious loss of memory and other cognitive functions, as well as affective, behavioral and psychiatric abnormalities, which gradually evolve into dementia. According to some estimates, the current prevalence of AD in the United States is over 4,000,000. Because the major risk factor for AD is age, its prevalence is projected to double within the next two decades due to aging of the 'Baby Boomer' generation and improved life expectancy.

The disease poses a major economic burden. The total annual cost per case in the US was estimated as $47,000 in 1990 [Rice D P et al. *Health Aff* 12:165–176 (1993), which translated into a national cost of $100 billion, or ~2% of the GDP in that year. These staggering statistics and the projected aging of the US population, make AD an enormous public health problem. Finding a cure for AD, or identifying measures to even modestly delay its onset would have a major public health impact.

The main obstacle for designing effective treatments for AD is the fact that the pathogenesis of the disease is not well understood. Histologically, brain tissue of AD patients shows extracellular senile plaques consisted mostly of β-amyloid (A-β) that is derived from APP (amyloid precursor protein), and intracellular neurofibrillary tangles containing pathologically hyperphosphorylated tau protein. The mechanisms leading to those changes are not well understood.

The etiology of AD has a strong genetic basis. Mutations in the APP or presenilin 1 (PS1) and PS2 genes, have been shown to underlie the early onset familial AD, whereas the risk for late-onset AD correlates with particular alleles of apolipoprotein (Apo) E [St. George-Hyslop PH. *Biol Psychiatry* 47:183–199 (2000)]. Interestingly, AD has long been noticed to be conspicuously rare among patients with RA [McGeer et al. *Lancet* 335:1037 (1990); Jenkinson et al. *Br J Rheumatol* 28:86–88 (1989); McGeer et al. *Neurology* 47:425–432 (1996)].

APP is a member of a family of transmembrane glycoproteins, which also include amyloid precursor-like protein-1 (APLP1) and APLP2. The physiologic function of these proteins is believed to involve cell-cell and cell-extracellular matrix interactions. In the familial forms of AD, due to mutations in either the APP gene or in PSN1 or PSN2, which affect APP processing, there is an increased cleavage of APP at the beta and gamma cleavage sites with resultant accelerated accumulation of Aβ.

Unlike the ubiquitously expressed APP and APLP2, APLP1 is expressed exclusively in the central nervous system, primarily in cerebral cortex postsynaptic densities [Kim T W et al. *Brain Res Mol Brain Res* 32:36–44 (1995)]. In addition to the putative functions of adhesion, neurite development and neuroprotection, shared by all members of the APP gene family, APLP1 may play a unique role in neurogenesis [Lorent K et al. *Neuroscience* 65:1009–1025 (1995)].

Genetic linkage studies indicate a susceptibility locus for AD on chromosome 19q12-q13 [Pericak-Vance MA et al. *Am J Hum Genet* 48:1034–1050 (1991)], a region which contains the APOE gene. The three major human ApoE alleles differ in two codons. The most common allele, ApoE3, is present in 75% of Caucasians and encodes a cysteine at position 112 and arginine at position 158. Allele ApoE2 (10% of Caucasians) encodes two cysteines, while ApoE4 (15% of Caucasians) has two arginines in those two positions. Analysis of the frequency of ApoE alleles in AD patients and controls show that there is increased frequency (40%) of the ApoE4 allele [Saunders A M et al. *Neurology* 43:1467–1472 (1993)] and decreased frequency (2%) of the ApoE2 allele [Corder E H et al. Nat Genet 7:180–184 (1994)] in patients with AD. Moreover, there is an inverse relationship between the number of ApoE4 copies and the age of onset of AD, with ApoE4/ApoE4 homozygous subjects showing the earliest age of onset [Corder E H et al. *Science* 261:921–923 (1993)].

Although the mechanism by which different ApoE alleles affect AD disease susceptibility is unclear, (and an understanding of this mechanism is not necessary to the successful practice of the invention) there is a substantial body of evidence to suggest that the ApoE polymorphism might directly influence the intracellular fate of tau and the processing of Aβ peptides [reviewed in Stirttmatter W J and Roses A D. *Proc Natl Acad Sci USA* 92:4725–4727 (1995); St. George-Hyslop PH. *Biol Psychiatry* 47:183–199 (2000)]. Studies with ApoE-deficient mice reveal memory deficits and hyperphosphorylation of tau. Taken together, human studies and ApoE knock out mice data support the hypothesis that ApoE may have a protective role, which allele ApoE4 may be uniquely devoid of.

Laminin has been shown to play a role in neuronal physiology [reviewed in Luckenbill-Edds L. *Brain Res Rev* 23:1–27 (1997)] and to modulate the neurodegenerative process in AD. For example, in vitro studies have shown that laminin inhibits formation of Aβ40 [Monji A et al. *Neurosci Lett* 251:65–68 (1998)] and Aβ42 [Monji A et al. *Brain Res* 788:187–190 (1998)] fibrils and attenuates amyloid peptide neurotoxicity in rat cortical neurons [Drouet B et al. *J Neurochem* 73:742–749 (1999)]. Interestingly, interaction of laminin with ApoE has been shown to enhance laminin's effect [Huang D Y et al. *Exp Neurol* 136:251–257 (1995)] and ApoE4-induced Aβ fibril formation can be reversed by laminin [Monji A et al. *Brain Res* 796:171–175 (1998)]. Thus, it is conceivable that laminin and ApoE encoded by either the ApoE2 or ApoE3 alleles operate synergistically, while the ApoE4 allele product has an opposite effect (but again, the invention is in no manner limited to such a mechanism). It is noteworthy that ApoE and laminin have been shown to co-localize anatomically in vivo.

AD begins slowly. At first, the only symptoms may be mild forgetfulness. People with AD may have trouble remembering recent events, activities, or the names of familiar people or things. Simple math problems may become hard for these people to solve. As the disease progresses, symptoms are more easily noticed and become serious enough to cause people with AD or their family members to seek medical help. For example, people with AD may forget how to do simple tasks, like brushing their teeth or combing their hair. They can no longer think clearly; and they begin to have problems speaking, understanding, reading, or writing. Later on, people with AD may become anxious or aggressive, or wander away from home. Eventually, patients may need total care. In general, the disease may be thought of in terms of three stages: mild, moderate and severe. Although the divisions are approximate and overlap, and progression of symptoms vary from one individual to the next, the symptoms and stages are still helpful in defining the disease state. Mild symptoms include confusion and memory loss, disorientation (getting lost in familiar surroundings), problems with routine tasks and changes in personality and judgement. Moderate symptoms include difficulty with activities of daily living (such as feeding and bathing), anxiety, suspiciousness, agitation, sleep disturbances, wandering, pacing and difficulty recognizing family and friends. Severe symptoms include loss of speech, loss of appetite and weight, loss of bladder and bowel control and total dependence on the caregiver.

Doctors at specialized centers can diagnose AD correctly 80 to 90 percent of the time. The presence of characteristic plaques and tangles in the brain can only be determined by looking at a piece of brain tissue under a microscope. It can be painful and risky to remove brain tissue while a person is alive, so doctors cannot look at the tissue until a post-mortem autopsy. Instead, doctors may say that a person has "probable" AD by finding out more about the patient's symptoms. For example, neuropsychological tests of memory, problem solving, attention, counting and language are carried out to pinpoint the specific problems the person has. The doctor may also carry out brain scans, such as computerized tomography, magnetic resonance imaging scans or positron emission tomography scans. These scans help the doctor rule out other causes of the person's symptoms, such as brain tumors or blood vessel disease.

Unfortunately, there is no specific treatment for AD. Cholinesterase inhibitors have been shown to have some effect in mild to moderate AD. Other treatments include free radical inhibitors, estrogen and anti-inflammatory drugs. None of these treatments has been found to effectively arrest disease progression. Consequently, AD management efforts are directed mostly at preventing complications, treating co-morbidities providing symptomatic relief, as well as offering educational and emotional support to patients and families.

2. Rheumatoid Arthritis

RA is the most common form of inflammatory arthritis, causing chronic inflammation of the joints, crippling deformities and early death [reviewed in Harris E D. *N Engl J Med* 322:1277–1289 (1990)]. Genetic predisposition to RA is strongly associated with the HLA-DRB1 locus of the major histocompatibility complex [Nepom G T et al. *Arthritis Rheum* 32:15–21 (1989)]. The vast majority of RA patients express HLA-DRB1 alleles encoding a "shared epitope" (SE), which contain the amino acid motif of QKRAA [Gln Lys Arg Ala Ala] [SEQ ID NO: 1] or QRRAA [Gln Arg Arg Ala Ala] [SEQ ID NO: 2] in residues 70–74 of the DRβ chain [Gregersen P K et al. *Arthritis Rheum* 30:1205–1213 (1987)]. Alleles encoding aspartic acid instead of glutamine in position 70 are negatively associated with RA.

The mechanism by which the shared epitope affects disease susceptibility is unknown. Several mechanisms have been put forward as explanations, including presentation of arthritogenic self-peptides, molecular mimicry with foreign antigens, T cell repertoire selection or linkage disequilibrium with other genes. While those mutually non-exclusive hypotheses are all plausible, none of them provide an explanation for the seemingly random occurrence of RA among genetically susceptible individuals, as illustrated in monozygotic (MZ) twins. Recent studies estimate the concordance rate of RA in MZ twins at 12–15% only. It has been therefore suggested that in addition to the strong influence of genetic factors, stochastic events, such as somatic mutations, might be involved. Indeed, higher mutation rates, increased sensitivity to genotoxic agents, and reduced DNA repair capacity have all been previously detected in RA.

While an understanding of this or any other mechanism is not necessary to the successful practice of the present invention, the inventors have shown that shared epitope-positive HLA-DRB1 allele products increase oxidative stress via activation of a calreticulin-mediated signaling cascade possibly by mimicking an as yet unknown physiologic calreticulin ligand, whereas RA-protective HLA-DRB1 allele products antagonize that effect. Consequently, individuals expressing RA-protective HLA-DRB1 alleles are less likely to experience the same extent of genotoxic challenge compared to individuals with shared epitope-positive HLA-DRB1 alleles. The shared epitope antagonist-containing peptide DKCLA, its permutations, and structurally analogous non-peptidic compounds are effective therapy for RA and other conditions involving oxidative stress. Such conditions include, but are not limited to: shared epitope- MHC-associated diseases (for example, polymyalgia rheumatica, giant cell arteritis, insulin-dependent diabetes mellitus, chronic lymphocytic leukemia, solid organ and formed element transplant rejection, and viral hepatitis); diseases with autoantibodies to calreticulin (for example, systemic lupus erythematosus (SLE), RA, Sjogren's syndrome, Crohns disease, insulin dependent diabetes mellitus (IDDM), multiple sclerosis (MS), parasitic infections, and halothane hepatitis); disorders associated with decreased production of cAMP (for example, asthma, atopic dermatitis, glomerulonephritis, psoriasis); and disorders associated with increased production of NO (for example, infectious disease, inflammatory bowel disease, osteoarthritis, septic shock, uremia). Thus, the association with a wide spectrum of antigenically and pathogenetically diverse diseases suggests that the RA shared epitope may exert antigen-nonspecific influence [Auger I et al. *Nature Med* 2:306–310 (1996)].

Free radicals and other reactive oxygen species (ROS) have long been implicated in the pathogenesis of RA [Brown K A. *Br J Rheumatol* 27: 150–155, (1988)]. Multiple lines of evidence indicate that aberrant regulation of oxidative stress exists in this disease [Maurice M M et al. *J Immunol* 158: 1458–1465, (1997), Cemerski S et al. *J Biol Chem* 277: 19585–19593, (2002), Cemerski S et al. *Eur J Immunol* 33: 2178–2185, (2003), Jikimoto T et al. *Mol Immunol* 38: 765–772, (2001), Rall L C et al. *J Nutr Biochem* 11: 581–584, (2000), Ueki Y et al. *J Rheumatol* 23: 230–236, (1996), Grant D D et al. *Environ Mol Mutagen* 38: 261–267, (2001), Migita K et al. *Immunology* 103: 362–367, (2001), Yamanishi Y et al. *Proc Natl Acad Sci (USA)* 99: 10025–10030, (2002)]. For example, RA synovial T cells demonstrate decreased intracellular GSH levels [Maurice M M et al. *J Immunol* 158: 1458–1465, (1997)], and increased production of thioredoxin in synovial tissues of RA patients has been shown to be a biomarker of oxidative stress [Jikimoto T et al. *Mol Immunol* 38: 765–772, (2001)]. Urinary excretion of 8-hydroxy-2'-deoxyguanosine has been found to be higher in RA patients, compared to healthy subjects [Rall L C et al. *J Nutr Biochem* 11: 581–584, (2000)], and increased NO levels have been demonstrated in the synovial fluid of RA patients [Ueki Y et al. *J Rheumatol* 23: 230–236, (1996)]. Thus, the rheumatoid synovial milieu contains oxidative substances that perpetuate the inflammatory state and create a genotoxic challenge. Increased levels of ROS and NO in RA have been blamed for T cell hyporesponsiveness [Cemerski S et al. *J Biol Chem* 277: 19585–19593, (2002), Cemerski S et al. *Eur J Immunol* 33: 2178–2185, (2003)], resistance to Fas-induced apoptosis [Migita K et al. *Immunology* 103: 362–367, (2001)], increased frequency of T cell mutations [Grant D D et al. *Environ Mol Mutagen* 38: 261–267, (2001)], and p53 mutations in synovial lining cells [Yamanishi Y et al. *Proc Natl Acad Sci (USA)* 99: 10025–10030, (2002)]. Shared epitope triggers pro-oxidative signaling, which increases oxidative stress. While an understanding of this or any other mechanism is not necessary to the successful practice of the present invention, it is apparent that shared epitope-positive individuals are more prone to mutations and immune dysregulation, placing them at a higher risk of disease initiation and perpetuation of the inflammatory process. Accordingly, antagonists of the shared epitope pro-oxidative effect possess prophylactic and therapeutic utility in RA.

In addition to its well-documented role in disease susceptibility, evidence suggests that the RA shared epitope contributes to disease severity as well [Weyand C M et al. *Ann Intern Med* 117:10 801–806 (1992); Gonzalez-Escribano M F et al. *Hum Immunol* 60:1259–1265 (1999); Valenzuela A et al. *Hum Immunol* 60:250–254 (1999); Salvarani C et al. *Br J Rheumatol* 37:165–169 (1998)]. Genetic analyses indicate that the shared epitope 'dose' has a measurable effect on disease outcome in many populations studied. Patients with a single shared epitope-expressing allele tend to have a milder disease, less destructive joint changes and infrequent extra articular involvement, as compared to patients with two such alleles. Thus, the shared epitope may have a dual role in RA: determination of disease susceptibility on the one hand, and affecting disease. severity on the other. The experimental results reported below indicate that the shared epitope has a direct impact on intracellular signaling events.

Rheumatoid arthritis is an inflammatory disease of the synovium, or lining of the joint that results in pain, stiffness, swelling, deformity, and loss of function in the joints. Inflammation most often affects joints of the hands and feet and tends to be symmetrical (occurring equally on both sides of the body). This symmetry helps distinguish rheumatoid arthritis from other types of arthritis. Pain and stiffness occur and last for more than 30 minutes in the morning or after a long rest.

Diagnosis of rheumatoid arthritis is often carried out by a rheumatologist. The doctor will review the patient's medical history, conduct a physical examination, and obtain laboratory tests and X-rays or other imaging tests. The doctor will examine all of the patient's joints for signs of redness, warmth, deformity, ease of movement, and tenderness. Some of the laboratory tests may include arthrocentesis (joint aspiration to obtain a sample of synovial fluid), a blood test to detect rheumatoid factor (an antibody found in the blood of most (but not all) people who have rheumatoid arthritis), or an erythrocyte sedimentation rate test (which can be indicative of inflammation present in the body). Early diagnosis is important, as destruction of cartilage and bone within the joint may begin as early as the first year or two that a person has the disease.

Treatment goals in RA are to relieve pain, reduce inflammation, slow down or stop joint damage and improve the person's sense of wellbeing and ability to function. Treatments for RA include rest and relaxation, exercise, proper diet and medication. Other treatments include the use of pain relief methods and assistive devices, such as splints or braces. In severe cases, surgery may be necessary. Medications include non-steroidal antiflammatories and other analgesics to reduce the pain and inflammation associated with RA. Other medications include gold, penicillamine, antimalarials (such as hydroxychloroquine), sulfasazine, methotrexate, azathioprine, cyclophosphamide and corticosteroids (such as prednisone and methylprednisolone).

However, current treatment methods for RA are costly, associated with severe side effects, and are often ineffective. Established treatments, as well as experimental therapeutic modalities, are designed to inhibit either final common pathways of inflammation, or immunological mediators. Both approaches are non-specific and, therefore, are associated with deleterious side effects. For example, nonsteroidal anti-inflammatory drugs currently in use are designed to nonspecifically inhibit prostaglandin synthesis and therefore are associated with gastrointestinal and renal toxicity. Corticosteroids have multiple effects on the immune system and other tissues. Their use is complicated by very high incidence of musculoskeletal, metabolic, neurologic and connective tissue side effects, as well as immunosuppression, which may lead to life-threatening infections. Cytotoxic and anti-metabolic drugs, such as methotrexate, azathioprine and cyclophosphamide non-specifically affect all rapidly dividing cells, and therefore are associated with bone marrow and gastrointestinal toxicity as well as an increased incidence of malignancy. Gold compounds and penicillamine are associated with high incidence of bone marrow, renal and mucocutaneous toxicity that over the years have led to almost complete abandonment of their use in RA. Anti malarials are effective in mild cases of RA. The main side effects are retinal and neuromuscular toxicity. Anti-TNF.alpha, therapy shows some promise. However, due to the ubiquitous role of TNF.alpha. in many cellular functions, anti-TNF therapy may not be a safe therapeutic strategy. There is increasing evidence of serious infections, exacerbation of multiple sclerosis, and development of lupus-like disease with this treatment. The effectiveness of antibodies against T cell surface antigens, induction of oral tolerance with collagen, or the use of oral antibiotics have not been conclusively established.

Due to its chronically progressive and debilitating nature, RA is a significant public health problem. Synthesis of shared epitope antagonist-containing peptides and other compounds is inexpensive. Hence, treatments disclosed herein are effective both for prophylaxis and therapeutic purposes. Additionally, due to its specificity, the therapeutic approach of the present invention is better tolerated and more effective than current treatments for RA and other MHC-associated diseases.

3. Negative Association between AD and RA

AD is conspicuously rare in RA patients. Both case-control and population-based studies have revealed a strong negative association between the two diseases [McGeer et al. *Lancet* 335:1037 (1990); Jenkinson et al. *Br J Rheumatol* 28:86–88 (1989); McGeer et al. *Neurology* 47:425–432 (1996)]. Statistical meta-analysis of the literature estimated the odd ratio for AD in RA as 0.194 ($p<0.0001$). The negative association between the two diseases has been previously attributed to extensive use of presumably AD-protective NSAID by RA patients. However, more recent evidence indicates that the negative association of AD with RA could be directly attributed to the RA-associated HLA-DRB1, rather than to drug use history, since DR4 itself has been found to associate with decreased risk for AD [Curran M et al. *NeuroReport* 8:1467–1469 (1997)]. Quantification of glial fibrillary acidic protein in hippocampal tissues from AD patients suggest that HLA-DR4 may exert a protective influence on AD [Aisen P S et al. *J Neurol Sci* 161:66–69 (1998)].

C. Compositions

While not wishing to be limited to any particular mechanism, it is believed that shared epitope- and shared epitope motif-containing peptides, derivatives, analogues, mimetics and antagonists can be used to counteract or reverse signal transduction aberrations underlying a number of diseases, including AD and RA. As demonstrated in the Experimental section below, shared epitope- and shared epitope motif-containing peptides inhibit cAMP-mediated DNA repair induction in cultured cells, as do genetically engineered shared epitope-containing proteins. Additionally, shared epitope-containing peptides confer neuroprotective effects in cultured cells.

As noted above, the vast majority of RA patients express HLA-DRB1 alleles encoding a "shared epitope" (SE), which contain the amino acid motif of QKRAA [Gln Lys Arg Ala Ala] [SEQ ID NO: 1] or QRRAA [Gln Arg Arg Ala Ala] [SEQ ID NO: 2] in residues 70–74 of the DRβ chain [Gregersen P K et al. *Arthritis Rheum* 30:1205–1213 (1987)].

As illustrated in the examples below, the cAMP-inhibiting domain of RA-associated shared epitope maps to the third allelic hypervariable region of the DRβ protein. Inhibition of cAMP signaling was obtained by incubating cells with particular synthetic peptides, corresponding to amino acids 65–79 or 65–78 of particular alleles of the third allelic hypervariable domain of DRβ Inhibition was associated with the peptides corresponding to the third allelic hypervariable region of the RA-shared epitope-expressing DRB1 alleles *0401 and *0404, but not with peptides corresponding to that region in the control alleles *0402 or *0403. The sequences of the third allelic hypervariable region peptides used are shown in Table 3 below.

TABLE 3

Third Allelic Hypervariable Region Peptides Used in the Study. (Synthetic Peptides)

| Peptide | Amino Acid Sequence | SEQ ID NO. |
| --- | --- | --- |
| 65–79*0401 | KDLLEQKRAAVDTYC | [SEQ ID NO: 5] |
| | Lys Asp Leu Leu Glu | |
| | Gln Lys Arg Ala Ala | |
| | Val Asp Thr Tyr Cys | |
| 65–78*0401 | KDLLEQKRAAVDTY | [SEQ ID NO: 6] |
| | Lys Asp Leu Leu Glu | |
| | Gln Lys Arg Ala Ala | |
| | Val Asp Thr Tyr | |
| 65–79*0402 | KDILEDERAAVDTYC | [SEQ ID NO: 7] |
| | Lys Asp Ile Leu Glu | |
| | Asp Glu Arg Ala Ala | |
| | Val Asp Thr Tyr Cys | |
| 65–78*0402 | KDILEDERAAVDTY | [SEQ ID NO: 8] |
| | Lys Asp Ile Leu Glu | |
| | Asp Glu Arg Ala Ala | |
| | Val Asp Thr Tyr | |
| 65–79*0403 | KDLLEQRRAEVDTYC | [SEQ ID NO: 9] |
| | Lys Asp Leu Leu Glu | |
| | Gln Arg Arg Ala Glu | |
| | Val Asp Thr Tyr Cys | |

TABLE 3-continued

Third Allelic Hypervariable Region Peptides Used in the Study. (Synthetic Peptides)

| Peptide | Amino Acid Sequence | SEQ ID NO. |
| --- | --- | --- |
| 65–79*0404 | KDLLEQRRAAVDTYC | [SEQ ID NO: 10] |
| | Lys Asp Leu Leu Glu | |
| | Gln Arg Arg Ala Ala | |
| | Val Asp Thr Tyr Cys | |
| 65–78*0404 | KDLLEQRRAAVDTY | [SEQ ID NO: 28] |
| | Lys Asp Leu Leu Glu | |
| | Gln Arg Arg Ala Ala | |
| | Val Asp Thr Tyr | |

Further investigation identified the QRRAA [Gln Arg Arg Ala Ala] [SEQ ID NO: 2] shared epitope sequence in three human nervous system proteins: APLP1, laminin β2 and ankyrin B. A homologous sequence was also found around the variable position 158 of ApoE. Use of pentapeptides based on these sequences (see example below) showed that the cAMP signal-inhibiting sequences possess the Q-(K/R)-X-X-A [Gln (Lys/Arg) Xaa Xaa Ala (wherein Xaa represents any amino acid)] [SEQ ID NO: 3] motif. This motif exists in RA shared epitope, as well as in APLP1, laminin β2 and ApoE. Thus, the motif from the shared epitope which appears to be associated with signal transduction (i.e. the shared epitope motif) is Q-(K/R)-X-X-A [Gln (Lys/Arg) Xaa Xaa Ala (wherein Xaa represents any amino acid)] [SEQ ID NO: 3].

The length of shared epitope-, shared epitope antatonist-containing peptides (SEAPs), or shared epitope motif-containing peptides can vary. In some embodiments, shared epitope-, shared epitope antatonist-containing peptides, or shared epitope motif-containing peptides range in length from five to hundreds of amino acids. In other embodiments, shared epitope-, shared epitope antatonist-containing peptides, or shared epitope motif-containing peptides are between five amino acids and 75 amino acids in length. In other embodiments, shared epitope- or shared epitope motif-containing peptides are between five amino acids and 25 amino acids in length, and in yet other embodiments, shared epitope-, shared epitope antatonist-containing peptides, or shared epitope motif-containing peptides are between five amino acids and fifteen amino acids in length.

In some embodiments, said shared epitope-, shared epitope antatonist-containing peptides, or shared epitope motif-containing peptides comprise genetically engineered proteins. For example, said shared epitope-, shared epitope antatonist-containing peptides, or shared epitope motif-containing sequences may be inserted into the sequence of another protein, including, but not limited to, the hepatitis B core (HBc) protein. In one embodiment, residues 65–79 of the shared epitope-containing DRβ*0401 chain are engineered to be expressed at the tips of the HBc spikes. Recombinant viral particles thus comprise an shared epitope-containing peptide on the spikes of the viral shell. In other embodiments, shared epitope motif-containing peptides similarly expressed in an engineered HBc protein are contemplated. In still further embodiments, shared epitope antatonist-containing peptides similarly expressed in an engineered HBc protein are contemplated.

As noted above, sequences which vary from the QRRAA [Gln Arg Arg Ala Ala] [SEQ ID NO: 2] and the QKRAA [Gln Lys Arg Ala Ala] [SEQ ID NO: 1 ] shared epitope still retain biological activity, as assayed in a cAMP signaling assay (to measure induction of DNA repair; see experimental section below). For example, QKRLA [Gln Lys Arg Leu Ala] [SEQ ID NO: 11] and QKCLA [Gln Lys Cys Leu Ala] [SEQ ID NO: 12] pentapeptides inhibited cAMP signaling. Both of these pentapeptides conform to the Q(K/R)XXA [Gln (Lys/Arg) Xaa Xaa Ala (wherein Xaa represents any amino acid)] [SEQ ID NO: 3] motif. Other peptides containing variations of the Q(K/R)XXA [Gln (Lys/Arg) Xaa Xaa Ala (wherein Xaa represents any amino acid)] [SEQ ID NO: 3] motif are also expected to have cAMP signal inhibition activity. Any such peptides are contemplated for use in the present invention. Such shared epitope motif-containing peptides may have a range of lengths, from approximately five amino acids to peptides containing up to several hundred amino acids. Most preferably, shared epitope motif-containing peptides will range from approximately 5 amino acids to approximately 20 amino acids in length, even more preferably from approximately 5 to approximately 15 amino acids in length.

It is also believed that other alterations can be made to shared epitope-containing or shared epitope motif-containing peptides to produce variant peptides (i.e. derivatives and analogues) that retain biological activity. An alteration is defined as a substitution, deletion or insertion of one or more amino acids in the peptides of interest. For example, peptides comprising the sequence QHXXA [Gln His Xaa Xaa Ala (wherein Xaa represents any amino acid)] [SEQ ID NO: 4] are expected to have cAMP signal inhibition activity. Preferably, the alterations are conservative amino acid changes.

For example, it is contemplated that an isolated replacement of a leucine with an isoleucine or valine, an alanine with a glycine, a threonine with a serine or a similar replacement of an amino acid with a structurally related amino acid (i.e. conservative substitutions) will not have a major effect on the biological activity of the resulting molecule. Conservative substitutions are those that take place within a family of amino acids that are related by their side chains. Amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In an alternative, yet similar fashion, the amino acid repertoire can be grouped as: (1) acidic (aspartate, glutamate); (2) basic (lysine, arginine, histidine); (3) aliphatic (glycine, alanine, valine, leucine, isoleucine, serine, threonine), with serine and threonine optionally grouped separately as aliphatic-hydroxyl; (4) aromatic (phenylalanine, tyrosine, tryptophan); (5) amide (asparagine, glutamine); and (6) sulfur-containing (cysteine and methionine) (See e.g. Stryer ed., Biochemistry, 2E, WH Freeman and Co. (1981) pp. 13–16).

Thus, in certain embodiments, modifications of the shared epitope- or shared epitope motif-containing peptides selected from the group consisting of SEQ ID NOs: 1, 2, 3, 5, 6, 10, 11, 12 and 17 are contemplated by the present invention. Guidance in determining which and how many amino acid residues may be substituted, inserted, or deleted without abolishing biological activity may be found by using computer programs well known in the art, for example, DNAStar software or GCG (Univ. of Wisconsin).

Whether a change in the amino acid sequence of an shared epitope- or shared epitope motif-containing peptide defined by an amino acid sequence selected from the group consisting of SEQ ID NOs: 1, 2, 3, 5, 6, 10, 11, 12 and 17 results in a peptide useful for counteracting or reversing disease-causing signaling defects in diseases with underlying signal transduction defects, including but not limited to AD, can be readily determined by an in vitro assay for cAMP-mediated signaling as described in the examples below. Briefly, one such assay involves the assessment of the repair of $H_2O_2$-induced DNA damage. Cells can be preincubated in the presence or absence of various shared epitope-containing peptides, analogues or derivatives prior to induction of DNA damage.

As noted, in several embodiments, the derivatives of the present invention are peptides having sequence homology to the above-described shared epitope, and shared epitope antagonist-containing peptide sequences and motif. One common methodology for evaluating sequence homology, and more importantly statistically significant similarities, is to use a Monte Carlo analysis using an algorithm written by Lipman and Pearson to obtain a Z value. According to this analysis, a Z value greater than 6 indicates probable significance, and a Z value greater than 10 is considered to be statistically significant. (W R Pearson and D J Lipman. Proc. Natl. Acad. Sci. (USA) 85:2444–2448 (1988); D J Lipman and W R Pearson. Science 227:1435–1441 (1985)). In the present invention, synthetic polypeptides useful in counteracting and reversing disease-causing signaling defects in diseases with underlying signal transduction aberrations, including but not limited to AD, are those peptides with statistically significant sequence homology and similarity (Z value of Lipman and Pearson algorithm in Monte Carlo analysis exceeding 6).

In yet other embodiments, shared epitope- or shared epitope motif-containing peptide analogues or derivatives comprise genetically engineered proteins, including, but not limited to, the hepatitis B core (HBc) protein. In these embodiments, the shared epitope- or shared epitope motif derivatives or analogues are engineered to be expressed at the tips of the HBc spikes. Recombinant viral particles thus comprise an shared epitope- or shared epitope motif-derivative or analogue on the spikes of the viral shell.

As is known in the art, peptides can be synthesized by linking an amino group to a carboxyl group that has been activated by reaction with a coupling agent, such as dicyclohexylcarbodiimide (DCC). The attack of a free amino group on the activated carboxyl leads to formation of peptide bond and the release of dicyclohexylurea. It can be necessary to protect potentially reactive groups other than the amino and carboxyl groups intended to react. For example, the .alpha.-amino group of the component containing the activated carboxyl group can be blocked with a tertbutyloxycarbonyl group. This protecting group can be subsequently removed by exposing the peptide to dilute acid, which leaves peptide bonds intact. With this method, peptides can be readily synthesized by a solid phase method by adding amino acids stepwise to a growing peptide chain that is linked to an insoluble matrix, such as polystyrene beads. The carboxyl-terminal amino acid (with an amino protecting group) of the desired peptide sequence is first anchored to the polystyrene beads. The protecting group of the amino acid is then removed. The next amino acid (with the protecting group) is added with the coupling agent. This is followed by a washing cycle. The cycle is repeated as necessary.

As noted above, the present invention contemplates peptides that are protease resistant. In one embodiment, such protease-resistant peptides are peptides comprising protecting groups. In a preferred embodiment, the present invention contemplates a peptide comprising the shared epitope, shared epitope antatonist-containing peptides, or shared epitope motif that is protected from protease degradation by N-terminal acetylation ("Ac") and C-terminal amidation. The acetylated and amidated shared epitope- or shared epitope motif-containing peptide is useful for in vivo administration because of its resistance to proteolysis.

In another embodiment, the present invention also contemplates peptides their corresponding D-isomers. It is not intended that the present invention be limited to particular amino acids and particular D-isomers. This embodiment is feasible for all amino acids, except glycine; that is to say, it is feasible for all amino acids that have two stereoisomeric forms. By convention, these mirror-image structures are called the D and L forms of the amino acid. These forms cannot be interconverted without breaking a chemical bond. With rare exceptions, only the L forms of amino acids are found in naturally occurring proteins. In one embodiment, the present invention contemplates Q(dK)RAA-[Gln (dLys) Arg Ala Ala] [SEQ ID NO: 13] containing peptides.

In other embodiments, peptides protected from protease degradation by both the use of protecting groups and substitution of L-amino acids with their corresponding D-isomers are contemplated. For example, a peptide comprising at least one D-amino acid can be acetylated and amidated as described above.

1. Calreticulin

Calreticulin is a ubiquitous, multifunctional, calcium-binding protein that the present inventors have found, for the first time, binds shared epitope-containing peptides. Although originally characterized as an endoplasmic reticulum (ER) molecular chaperone, more recently it has been shown to attach to low density lipoprotein receptor-related protein (LRP/CD91/alpha-2 macroglobulin receptor) on the cell surface. (See, Basu S, Binder R J, Ramalingam T and Seivastava P. CD91 is a common receptor for heat shock proteins gp96, hsp70, and calreticulin. *Immunity* 14: 303–313, 2001.) Calreticulin has also been implicated in signal transduction events associated with cell adhesion, angiogenesis and apoptosis. Because calreticulin lacks transmembrance domain, LRP may serve as a partner receptor, which transduces calreticulin-triggered signaling. Both LRP and calreticulin signaling have been shown to involve intracellular NO production. Peptide-mediated calreticulin effects require binding to the cell surface, and involves rapid transmembranal activation of NO synthase (NOS), with a resultant increase in NO and cGMP levels, followed by activation of PKG.

Calreticulin modulates neuronal physiology. Increased cell surface expression of this protein is associated with neurite formation and neuronal survival. (See Johnson R J, Xiao G, Shanmugaratnam J and Fine R E. Increased calreticulin stability in differentiated NG-108–15 cells correlates with resistance to apoptosis induced by antisense treatment. *Mol. Biol. Aging* 53:104–11, 1998.) Additionally, calreticulin has been shown to bind neuromodulatory proteins, such as APP (intracellularly) and laminin (extracellularly). A recent study has shown that cell surface calreticulin specifically binds neuronal survival-promoting peptide Y-P30 and mediates its neuroprotective effect. Calreticulin binding and other biological activities of survival peptide Y-P30 including effects of systemic treatment of rats. (*Exp Neurol* 163: 457–468, 2000.) While it is not intended that the present invention be limited to any specific mechanism, calreticulin shows decreased expression in AD neurons. Moreover, in sum, these observations implicate calreticulin dysfunction in the pathogenesis of AD.

While its role in AD may be protective, in rheumatoid arthritis (RA) calreticulin is pathological. (See, Sontheimer R D, Lieu T S and Cpara J D. Calreticulin: the diverse functional repertoire of a new human autoantigen. *Immunologisti* 1:155, 1993.) In contrast to AD neurons, the expression level of calreticulin in RA patients is increased. Moreover, calreticulin-derived peptides (residues 295–309) bind specifically to RA-associated HLA-DRβ molecule.

a. Anti-Calreticulin Antibodies

In one embodiment of the present invention, calreticulin antagonist compounds are specifically contemplated. In some embodiments, said calreticulin antagonist compoundis one or more antibodies. In a preferred embodiment, said antibody is an anti-calreticulin antibody.

The present invention provides isolated antibodies or antibody fragments (e.g., FAB fragments). Antibodies can be generated to allow for the antagonism of calreticulin protein. The antibodies may be prepared using various immunogens. In one embodiment, the immunogen is a human calreticulin peptide to generate antibodies that recognize human calreticulin. Such antibodies include, but are not limited to polyclonal, monoclonal, chimeric, single chain, Fab fragments, Fab expression libraries, or recombinant (e.g., chimeric, humanized, etc.) antibodies, as long as it can recognize the protein. Antibodies can be produced by using a protein of the present invention as the antigen according to a conventional antibody or antiserum preparation process.

Various procedures known in the art may be used for the production of polyclonal antibodies directed against calreticulin. For the production of antibody, various host animals can be immunized by injection with the peptide corresponding to the calreticulin epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward calreticulin, it is contemplated that any technique that provides for the production of antibody molecules by continuous cell lines in culture will find use with the present invention (See e.g., Harlow and Lane, *Antibodies: A Laboratory Manual,* Cold Spring Harbor Laboratory Press, Cold Spring Harbor, N.Y.). These include but are not limited to the hybridoma technique originally developed by Köhler and Milstein (Köhler and Milstein, Nature 256:495–497 [1975]), as well as the trioma technique, the human B-cell hybridoma technique (See e.g., Kozbor et al., Immunol. Tod., 4:72 [1983]), and the EBV-hybridoma technique to produce human monoclonal antibodies (Cole et al., in *Monoclonal Antibodies and Cancer Therapy*, Alan R. Liss, Inc., pp. 77–96 [1985]).

In an additional embodiment of the invention, monoclonal antibodies are produced in germ-free animals utilizing technology such as that described in PCT/US90/02545). Furthermore, it is contemplated that human antibodies will be generated by human hybridomas (Cote et al., Proc. Natl. Acad. Sci. USA 80:2026–2030 [1983]) or by transforming human B cells with EBV virus in vitro (Cole et al., in *Monoclonal Antibodies and Cancer Therapy*, Alan R. Liss, pp. 77–96 [1985]).

In addition, it is contemplated that techniques described for the production of single chain antibodies (U.S. Pat. No. 4,946,778; herein incorporated by reference) will find use in producing calreticulin specific single chain antibodies. An additional embodiment of the invention utilizes the techniques described for the construction of Fab expression libraries (Huse et al., Science 246:1275–1281 [1989]) to allow rapid and easy identification of monoclonal Fab fragments with the desired specificity for calreticulin.

In other embodiments, the present invention contemplated recombinant antibodies or fragments thereof to the proteins of the present invention. Recombinant antibodies include, but are not limited to, humanized and chimeric antibodies. Methods for generating recombinant antibodies are known in the art (See e.g., U.S. Pat. Nos. 6,180,370 and 6,277,969 and "Monoclonal Antibodies" H. Zola, BIOS Scientific Publishers Limited 2000. Springer-Verlay New York, Inc., New York; each of which is herein incorporated by reference).

It is contemplated that any technique suitable for producing antibody fragments will find use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody will be accomplished by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.)

Another method uses antibodies as agents to alter signal transduction. Specific antibodies that bind to the binding domains of calreticulin or other proteins involved in intracellular signaling can be used to inhibit the interaction between the various proteins and their interaction with other ligands. Antibodies that bind to the complex can also be used therapeutically to inhibit interactions of the protein complex in the signal transduction pathways leading to the various physiological and cellular effects of calreticulin. Such antibodies can also be used diagnostically to measure abnormal expression of calreticulin, or the aberrant formation of protein complexes, which may be indicative of a disease state.

b. Calreticulin (Crt) Antisense Oligonucleotides

In another embodiment of the present invention, said calreticulin antagonist compound is an antisense oligonucleotide configured to inhibit expression of calreticulin. For example, in some embodiments, the present invention employs compositions comprising oligomeric antisense compounds, particularly oligonucleotides (e.g., those identified in the drug screening methods described above), for use in modulating the function of nucleic acid molecules encoding calreticulin, ultimately modulating the amount of calreticulin expressed. This is accomplished by providing antisense compounds that specifically hybridize with one or more nucleic acids encoding calreticulin. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of calreticulin. In the context of the present invention, "modulation" means either an increase (stimulation) or a decrease (inhibition) in the expression of a gene. For example, expression may be inhibited to potentially improve the signs or symptoms of rheumatoid arthritis.

It is preferred to target specific nucleic acids for antisense. "Targeting" an antisense compound to a particular nucleic acid, in the context of the present invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding calreticulin. The targeting process also includes determination of a site or sites within this gene for the antisense interaction to occur such that the desired effect, e.g., detection or modulation of expression of calreticulin, will result. Within the context of the present invention, a preferred intragenic site is the region encompassing the translation initiation or termination codon of the open reading frame (ORF) of the gene. Since the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the present invention, "start codon" and "translation initiation codon" refer to the codon or codons that are used in vivo to initiate translation of an mRNA molecule transcribed from a gene encoding calreticulin, regardless of the sequence(s) of such codons.

Translation termination codon (or "stop codon") of a gene may have one of three sequences (i.e., 5'-UAA, 5'-UAG and 5'-UGA; the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which refers to the region between the translation initiation codon and the translation termination codon, is also a region that may be targeted effectively. Other target regions include the 5' untranslated region (5' UTR), referring to the portion of an mRNA in the 5' direction from the translation initiation codon, and thus including nucleotides between the 5' cap site and the translation initiation codon of an mRNA or corresponding nucleotides on the gene, and the 3' untranslated region (3' UTR), referring to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The cap region may also be a preferred target region.

Although some eukaryotic mRNA transcripts are directly translated, many contain one or more regions, known as "introns," that are excised from a transcript before it is translated. The remaining (and therefore translated) regions are known as "exons" and are spliced together to form a continuous mRNA sequence. mRNA splice sites (i.e., intron-exon junctions) may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

In some embodiments, target sites for antisense inhibition are identified using commercially available software programs (e.g., Biognostik, Gottingen, Germany; SysArris Software, Bangalore, India; Antisense Research Group, University of Liverpool, Liverpool, England; GeneTrove, Carlsbad, Calif.). In other embodiments, target sites for antisense inhibition are identified using the accessible site method described in U.S. Patent WO0198537A2, herein incorporated by reference.

Once one or more target sites have been identified, oligonucleotides are chosen that are sufficiently complementary to the target (i.e., hybridize sufficiently well and with sufficient specificity) to give the desired effect. For example, in preferred embodiments of the present invention, antisense oligonucleotides are targeted to or near the start codon.

In the context of this invention, "hybridization," with respect to antisense compositions and methods, means hydrogen bonding, which may be Watson-Crick, Hoogsteen or reversed Hoogsteen hydrogen bonding, between complementary nucleoside or nucleotide bases. For example, adenine and thymine are complementary nucleobases that pair through the formation of hydrogen bonds. It is understood that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired (i.e., under physiological conditions in the case of in vivo assays or therapeutic treatment, and in the case of in vitro assays, under conditions in which the assays are performed).

Antisense compounds are commonly used as research reagents and diagnostics. For example, antisense oligonucleotides, which are able to inhibit gene expression with specificity, can be used to elucidate the function of particular genes. Antisense compounds are also used, for example, to distinguish between functions of various members of a biological pathway.

The specificity and sensitivity of antisense is also applied for therapeutic uses. For example, antisense oligonucleotides have been employed as therapeutic moieties in the treatment of disease states in animals and humans. Antisense oligonucleotides have been safely and effectively administered to humans and numerous clinical trials are presently underway. It is thus established that oligonucleotides are useful therapeutic modalities that can be configured to be useful in treatment regimes for treatment of cells, tissues, and animals, especially humans.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases (i.e., from about 8 to about 30 linked bases), although both longer and shorter sequences may find use with the present invention. Particularly preferred antisense compounds are antisense oligonucleotides, even more preferably those comprising from about 12 to about 25 nucleobases.

Specific examples of preferred antisense compounds useful with the present invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'–5' linkages, 2'–5' linked analogs of these, and those having inverted polarity wherein the adjacent pairs of nucleoside units are linked 3'–5' to 5'–3' or 2'–5' to 5'–2'. Various salts, mixed salts and free acid forms are also included.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other preferred oligonucleotide mimetics, both the sugar and the internucleoside linkage (i.e., the backbone) of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos.: 5,539,082; 5,714,331; and 5,719,262, each of which is herein incorporated by reference. Further teaching of PNA compounds can be found in Nielsen et al., Science 254:1497 (1991).

Most preferred embodiments of the invention are oligonucleotides with phosphorothioate backbones and oligonucleosides with heteroatom backbones, and in particular —$CH_2$—, —NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$—, and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, C2, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., Helv. Chim. Acta 78:486 [1995]) i.e., an alkoxyalkoxy group. A further preferred modification includes 2'-dimethylaminooxyethoxy (i.e., a $O(CH_2)_2ON(CH_3)_2$ group), also known as 2'-DMAOE, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$.

Other preferred modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'–5' linked oligonucleotides and the 5' position of 5' terminal nucleotide. Oligonucleotides may also have sugar mimetics such as cyclobutyl moieties in place of the pentofuranosyl sugar.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2. degree ° C. and are presently preferred base substitutions, even more particularly when combined with 2'-O-methoxyethyl sugar modifications.

Another modification of the oligonucleotides of the present invention involves chemically linking to the oligonucleotide one or more moieties or conjugates that enhance the activity, cellular distribution or cellular uptake of the oligonucleotide. Such moieties include but are not limited to lipid moieties such as a cholesterol moiety, cholic acid, a thioether, (e.g., hexyl-S-tritylthiol), a thiocholesterol, an aliphatic chain, (e.g., dodecandiol or undecyl residues), a phospholipid, (e.g., di-hexadecyl-rac-glycerol or triethylammonium 1,2-di-O-hexadecyl-rac-glycero-3-H-phosphonate), a polyamine or a polyethylene glycol chain or adamantane acetic acid, a palmityl moiety, or an octadecylamine or hexylamino-carbonyl-oxycholesterol moiety.

One skilled in the relevant art knows well how to generate oligonucleotides containing the above-described modifications. The present invention is not limited to the antisensce oligonucleotides described above. Any suitable modification or substitution may be utilized.

It is not necessary for all positions in a given compound to be uniformly modified, and in fact more than one of the aforementioned modifications may be incorporated in a single compound or even at a single nucleoside within an oligonucleotide. The present invention also includes antisense compounds that are chimeric compounds. "Chimeric" antisense compounds or "chimeras," in the context of the present invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNaseH is a cellular endonuclease that cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the present invention may be formed as composite structures of two or more oligonucleotides, modified oligonucleotides, oligonucleosides and/or oligonucleotide mimetics as described above.

The present invention also includes pharmaceutical compositions and formulations that include the antisense compounds of the present invention as described below.

c. Calreticulin siRNA

In a still further embodiment of the present invention, said calreticulin antagonist compound is a small interfering RNA duplex, or vectors encoding said small interfering RNA duplex, configured to inhibit expression of calreticulin.

1. RNA Interference (RNAi)

The present invention provides RNAi for inhibiting the expression of the calreticulin protein in cells. Preferably, inhibition of the level of calreticulin expression in cells prevents or reduces the capacity for pro-oxidative damage. RNAi represents an evolutionary conserved cellular defense for controlling the expression of foreign genes in most eukaryotes. RNAi is triggered by double-stranded RNA (dsRNA) and causes sequence-specific mRNA degradation of single-stranded target RNAs homologous in response to dsRNA. The mediators of mRNA degradation are small interfering RNA duplexes (RNAi), which are normally produced from long dsRNA by enzymatic cleavage in the cell. RNAi are generally approximately twenty-one nucleotides in length (e.g. 21–23 nucleotides in length), and have a base-paired structure characterized by two nucleotide 3'-overhangs. Following the introduction of a small RNA, or RNAi, into the cell, it is believed the sequence is delivered to an enzyme complex called RISC (RNA-induced silencing complex). RISC recognizes the target and cleaves it with an endonuclease. It is noted that if larger RNA sequences are delivered to a cell, RNase III enzyme (Dicer) converts longer dsRNA into 21–23 nt dsRNA fragments.

Chemically synthesized dsRNAs have become powerful reagents for genome-wide analysis of gene function in cultured somatic cells. The transfection of dsRNAs into host cells results in the potent, long-lasting post-transcriptional silencing of specific genes (Caplen et al, *Proc Natl Acad Sci U.S.A.* 98: 9742–7 (2001), Elbashir et al., *Nature* 2001 411:494–8 (2001), Elbashir et al., Genes Dev 15: 188–200 (2001), and Elbashir et al., *EMBO J.* 20: 6877–88 (2001)). Methods and compositions for performing RNAi with dsRNAs are described, for example, in U.S. Pat. No. 6,506,559. RNAi is extraordinarily effective at lowering the amounts of targeted RNA, and by extension proteins, frequently to undetectable levels. The silencing effect can last several months, and is extraordinarily specific, because one nucleotide mismatch between the target RNA and the central region of the dsRNA is frequently sufficient to prevent silencing (Brummelkamp et al, *Science* 296:550–3 (2002), and Holen et al, *Nucleic Acids Res.* 30:1757–66 (2002).

2. Designing and Testing RNAi for Calreticulin

In order to design dsRNAs for calreticulin (e.g. that target calreticulin mRNA) software design tools are available in the art (e.g. on the Internet). For example, Oligoengine's web page has one such design tool that finds RNAi candidates based on Elbashir's (Elbashir, 2002) criteria. Other design tools may also be used, such as the Cenix Bioscience design tool offered by Ambion. In addition, there is also the Si2 silencing duplex offered by Oligoengine.

There are also RNA folding software programs available that allow one to determine if the mRNA has a tendency to fold on its own and form a "hair-pin" (which in the case of dsRNAi is not as desirable since one goal is to have the RNAi attach to the mRNA and not itself). One preferred configuration is an open configuration with three or less bonds. Generally, a positive delta G is desirable to show that it would not tend to fold on itself spontaneously. RNAi candidate molecules that are generated can be, for example, screened in an animal model of osmotic resistance in vivo using similar techniques as described above.

3. Expression Cassettes

Calreticulin specific RNAi of the present invention may be synthesized chemically. Chemical synthesis can be achieved by any method known or discovered in the art. Alternatively, calreticulin specific RNAi of the present invention may be synthesized by methods which comprise synthesis by transcription. In some embodiments, transcription is in vitro, as from a DNA template and bacteriophage RNA polymerase promoter, in other embodiments, synthesis is in vivo, as from a gene and a promoter. Separate-stranded duplex RNAi, where the two strands are synthesized separately and annealed, can also be synthesized chemically by any method known or discovered in the art. Alternatively, dsRNAs are synthesized by methods that comprise synthesis by transcription. In some embodiments, the two strands of the double-stranded region of an RNAi is expressed separately by two different expression cassettes, either in vitro (e.g., in a transcription system) or in vivo in a host cell, and then brought together to form a duplex.

Thus, in another aspect, the present invention provides a composition comprising an expression cassette comprising a promoter and a gene that encodes a RNAi specific for calreticulin. In some embodiments, the transcribed dsRNA forms a single strand of a separate-stranded duplex (or double-stranded, or ds) RNA of about 18 to 25 base pairs long; thus, formation of dsRNA requires transcription of each of the two different strands of a dsRNA. The term "gene" in the expression cassette refers to a nucleic acid sequence that comprises coding sequences necessary for the production of a dsRNA. Thus, a gene includes but is not limited to coding sequences for a strand of a dsRNA.

Generally, a DNA expression cassette comprises a chemically synthesized or recombinant DNA molecule containing at least one gene, or desired coding sequence for a single strand of a dsRNA, and appropriate nucleic acid sequences necessary for the expression of the operably linked coding sequence, either in vitro or in vivo. Expression in vitro may include expression in transcription systems and in transcription/translation systems. Expression in vivo may include expression in a particular host cell and/or organism. Nucleic acid sequences necessary for expression in a prokaryotic cell or in a prokaryotic in vitro expression system are well known and usually include a promoter, an operator, and a ribosome binding site, often along with other sequences. Eukaryotic in vitro transcription systems and cells are known to utilize promoters, enhancers, and termination and polyadenylation signals. Nucleic acid sequences necessary for expression via bacterial RNA polymerases (such as T3, T7, and SP6), referred to as a transcription template in the art, include a template DNA strand which has a polymerase promoter region followed by the complement of the RNA sequence desired (or the coding sequence or gene for the siRNA). In order to create a transcription template, a complementary strand is annealed to the promoter portion of the template strand.

In any of the expression cassettes described above, the gene may encode a transcript that contains at least one cleavage site, such that when cleaved results in at least two cleavage products. Such products can include the two opposite strands of a ds siRNA. In an expression system for expression in a eukaryotic cell, the promoter may be constitutive or inducible; the promoter may also be tissue or organ specific (e.g. specific to the eye), or specific to a developmental phase. Preferably, the promoter is positioned 5' to the transcribed region. Other promoters are also contemplated; such promoters include other polymerase III promoters and microRNA promoters.

Preferably, a eukaryotic expression cassette further comprises a transcription termination signal suitable for use with the promoter; for example, when the promoter is recognized by RNA polymerase III, the termination signal is an RNA polymerase III termination signal. The cassette may also include sites for stable integration into a host cell genome.

4. Vectors

In other aspects of the present invention, the compositions comprise a vector comprising a gene encoding an RNAi specific for calreticulin or preferably at least one expression cassette comprising a promoter and a gene which encodes a sequence necessary for the production of a RNAi specific for calreticulin (an RNAi gene). The vectors may further comprise marker genes, reporter genes, selection genes, or genes of interest, such as experimental genes. Vectors of the present invention include cloning vectors and expression vectors. Expression vectors may be used in in vitro transcription/translation systems, as well as in in vivo in a host cell. Expression vectors used in vivo in a host cell may be transfected into a host cell, either transiently, or stably. Thus, a vector may also include sites for stable integration into a host cell genome.

In some embodiments, it is useful to clone an RNAi gene downstream of a bacteriophage RNA polymerase promoter into a multicopy plasmid. A variety of transcription vectors containing bacteriophage RNA polymerase promoters (such as T7 promoters) are available. Alternatively, DNA synthesis can be used to add a bacteriophage RNA polymerase promoter upstream of an RNAi coding sequence. The cloned plasmid DNA, linearized with a restriction enzyme, can then be used as a transcription template (See for example Milligan and Uhlenbeck. *Methods in Enzymology* 180: 51–64 (1989)).

In other embodiments of the present invention, vectors include, but are not limited to, chromosomal, nonchromosomal and synthetic DNA sequences (e.g., derivatives of viral DNA such as vaccinia, adenovirus, fowl pox virus, and pseudorabies). It is contemplated that any vector may be used as long as it is expressed in the appropriate system (either in vitro or in vivo) and viable in the host when used in vivo; these two criteria are sufficient for transient transfection. For stable transfection, the vector is also replicable in the host.

Large numbers of suitable vectors are known to those of skill in the art, and are commercially available. In some embodiments of the present invention, expression vectors comprise an origin of replication, suitable promoters and enhancers, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, a gene sequence in an expression vector which is not part of an expression cassette comprising an RNAi gene (specific for calreticulin) is operatively linked to an appropriate expression control sequence(s) (promoter) to direct mRNA synthesis. In some embodiments, the gene sequence is a marker gene or a selection gene. In other embodiments of the present invention, recombinant expression vectors include origins of replication and selectable markers permitting transformation of the host cell (e.g., dihydrofolate reductase or neomycin resistance for eukaryotic cell culture). In some embodiments of the present invention, transcription of DNA encoding a gene is increased by inserting an enhancer sequence into the vector. Enhancers are cis-acting elements of DNA, usually about from 10 to 300 bp that act on a promoter to increase its transcription. Preferably the design of a vector is configured to deliver the RNAi for more permanent inhibition.

5. Transfecting Cells

In yet other aspects, the present invention provides compositions comprising cells transfected by an expression cassette of the present invention as described above, or by a vector of the present invention, where the vector comprises an expression cassette (or simply the RNAi gene) of the present invention, as described above. In some embodiments of the present invention, the host cell is a synovial cell. A transfected cell may be a cultured cell or a tissue, organ, or organismal cell.

The cells may be transfected transiently or stably (e.g. DNA expressing the dsRNA is stably integrated and expressed by the host cell's genome). The cells may also be transfected with an expression cassette of the present invention, or they are transfected with an expression vector of the present invention. In some embodiments, transfected cells are are tissue, organ, or organismal cells.

In the present invention, cells to be transfected in vitro are typically cultured prior to transfection according to methods that are well known in the art, as for example by the preferred methods as defined by the American Tissue Culture Collection. In certain embodiments of the present invention, cells are transfected with dsRNAs that are synthesized exogenously (or in vitro, as by chemical methods or in vitro transcription methods), or they are transfected with expression cassettes or vectors, which express dsRNAs within the transfected cell.

In some embodiments, cells are transfected with dsDNAs by any method known or discovered in the art which allows a cell to take up exogenous RNA and remain viable. Non-limiting examples include electroporation, microinjection, transduction, cell fusion, DEAE dextran, calcium phosphate precipitation, use of a gene gun, osmotic shock, temperature shock, and electroporation, consumption and pressure treatment. In alternative, embodiments, the RNAi are introduced in vivo by lipofection.

In other embodiments expression cassettes or vectors comprising at least one expression cassette are introduced into the desired host cells by methods known in the art, including but not limited to transfection, electroporation, microinjection, transduction, cell fusion, DEAE dextran, calcium phosphate precipitation, use of a gene gun, or use of a DNA vector transporter. In some embodiments, various methods are used to enhance transfection of the cells. These methods include but are not limited to osmotic shock, temperature shock, and electroporation, and pressure treatment.

Alternatively, the vector can be introduced in vivo by lipofection. For the past decade, there has been increasing use of liposdmes for encapsulation and transfection of nucleic acids in vitro. Synthetic cationic lipids designed to limit the difficulties and dangers encountered with liposome-mediated transfection can be used to prepare liposomes for in vivo transfection of a gene encoding a marker. The use of cationic lipids may promote encapsulation of negatively charged nucleic acids, and also promote fusion with negatively charged cell membranes. Particularly useful lipid compounds and compositions for transfer of nucleic acids are described in WO95/18863 and WO96/17823, and in U.S. Pat. No. 5,459,127. Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931). It is also possible to introduce a sequence encoding a dsRNA in vivo as a naked DNA, either as an expression cassette or as a vector.

Stable transfection typically requires the presence of a selectable marker in the vector used for transfection. Transfected cells are then subjected to a selection procedure. Generally, selection involves growing the cells in a toxic substance, such as G418 or Hygromycin B, such that only those cells expressing a transfected marker gene conferring resistance to the toxic substance upon the transfected cell survive and grow. Such selection techniques are well known in the art. Typical selectable markers are well known, and include genes encoding resistance to G418 or hygromycin B.

In certain embodiments, certain chemical modifications of the dsRNAis such as changing the lipophilicity of the molecule may be employed (e.g., attachment of lipophilic residues at the 3' termini of the dsRNA). Delivery of dsRNAs into organisms may also be achieved with methods previously developed for the application of antisense oligonucleotides such as injection of liposomes-encapsulated molecules.

6. Kits

The present invention also provides kits comprising at least one expression cassette comprising a RNAi gene specific for calreticulin. In some aspects, a transcript from the expression cassette forms a double stranded RNAi of about 18 to 25 base pairs long. In other embodiments, the expression cassette is contained within a vector, as described above, where the vector can be used in in vitro transcription or transcription/translation systems, or used in vivo to transfect cells, either transiently or stably.

In other aspects, the kit comprises at least two expression cassettes, each of which comprises a RNAi gene, such that at least one gene encodes one strand of a RNAi that combines with a strand encoded by a second cassette to form a dsRNA; the dsRNA so produced is any of the embodiments described above. These cassettes may comprise a promoter and a sequence encoding one strand of a dsRNA. In some further embodiments, the two expression cassettes are present in a single vector; in other embodiments, the two expression cassettes are present in two different vectors. A vector with at least one expression cassette, or two different vectors, each comprising a single expression cassette, can be used in in vitro transcription or transcription/translation systems, or used in vivo to transfect cells, either transiently or stably.

In yet other aspects, the kit comprises at least one expression cassettes which comprises a gene which encodes two separate strands of a dsRNA and a processing site between the sequences encoding each strand such that, when the gene is transcribed, the transcript is processed, such as by cleavage, to result in two separate strands which can combine to form a dsRNA, as described above.

In some embodiments, the present invention provides kits comprising; a) a composition comprising small interfering RNA duplexes (RNAi) configured to inhibit expression of calreticulin protein, and b) printed material with instructions for employing the composition for treating a target cell expressing calreticulin protein via expression of calreticulin mRNA under conditions such that the calreticulin mRNA is cleaved or otherwise disabled.

7. Generating Calreticulin Specific siRNA

The present invention also provides methods of synthesizing dsRNAs specific for calreticulin. The dsRNAs may be synthesized in vitro or in vivo. In vitro synthesis includes chemical synthesis and synthesis by in vitro transcription. In vitro transcription is achieved in a transcription system, as from a bacteriophage RNA polymerase, or in a transcription/translation system, as from a eukaryotic RNA polymerase. In vivo synthesis occurs in a transfected host cell.

The dsRNAs synthesized in vitro, either chemically or by transcription, are used to transfect cells. Therefore, the present invention also provides methods of transfecting host cells with dsRNAs synthesized in vitro; in particular embodiments, the dsRNA are synthesized by in vitro transcription. The present invention further provides methods of silencing the calreticulin gene in vivo by transfecting cells with dsRNAs synthesized in vitro. In other methods, the dsRNA is expressed in vitro in a transcription/translation system from an expression cassette or expression vector, along with an expression vector encoding and expressing a reporter gene.

The present invention also provides methods of expressing dsRNA in vivo by transfecting cells with expression cassettes or vectors which direct synthesis of dsRNA in vivo. The present invention also provides methods of silencing genes in vivo by transfecting cells with expression cassettes or vectors that direct synthesis of dsRNA in vivo.

2. Mimetics

Compounds mimicking the necessary conformation for biological activity of the peptides of the present invention are contemplated as within the scope of this invention. For example, mimetics of DKCLA [SEQ ID NO; 16] containing peptides are contemplated. A variety of designs for such mimetics are possible. For example, cyclic DKCLA containing peptides, in which the necessary conformation for biological activity is stabilized by nonpeptides, are specifically contemplated. U.S. Pat. No. 5,192,746 to Lobl et al., U.S. Pat. No. 5,169,862 to Burke, Jr. et al., U.S. Pat. No. 5,539,085 to Bischoff et al., U.S. Pat. No. 5,576,423 to Aversa et al., U.S. Pat. No. 5,051,448 to Shashoua, and U.S. Pat. No. 5,559,103 to Gaeta et al., all herein incorporated by reference, describe multiple methods for creating such compounds.

Synthesis of non-peptide compounds that mimic peptide sequences is also known in the art. Eldred et al. (*J. Med. Chem.* 37:3882 (1994)) describe non-peptide antagonists that mimic an Arg-Gly-Asp sequence. Likewise, Ku et al. (*J. Med. Chem.* 38:9 (1995)) give further elucidation of a series of such compounds. Such non-peptide compounds that mimic DKCLA [SEQ ID NO: 16]—containing peptides are specifically contemplated by the invention.

The present invention also contemplates synthetic mimicking compounds that are multimeric compounds that repeat the relevant peptide sequences. In one embodiment of the present invention, it is contemplated that the relevant peptide sequence is DKCLA [SEQ ID NO: 16].

In some embodiments, the invention contemplates the use of antagonists of shared epitope- or shared epitope motif-containing peptides. Such antagonists are inhibitory, and produce an opposite signaling effect, or block the signaling effect of an agonist while producing reduced or absent signaling effects of their own. Without wishing to be limited to any particular mechanism, such antagonists may bind a (presently unknown) receptor without activating it. Such antagonists are contemplated to be used to suppress NO signaling and/or to increase cAMP activation where indicated. For example, a disease such as RA is contemplated for treatment by local application of such antagonists. Antagonists may be peptides or peptidomimetic compounds. The activity of a potential antagonist may be assayed in a variety of assays, including measurement of intracellular cAMP levels, measurement of protein kinase A activation, and measurement of signaling through a cAMP mediated signaling pathway, such as the induced DNA repair assay described in the examples below.

The present invention contemplates the design of peptide and nonpeptide mimetics based upon structural modeling of the DKCLA and related peptides, high resolution experimental three dimensional imaging of DKCLA, conformational and binding site analysis of shared epitope- and calreticulin-inhibitory peptides, rational design of shared epitope- and calreticulin-inhibitory compounds, screening of combinatorial peptide libraries for shared epitope- and calreticulin-inhibitory constituents, and design of bio-stable shared epitope- and calreticulin-inhibitory peptide and non-peptide mimetics. Certain of the compounds suitable for use in the present invention may exist as stereoisomers including optical isomers. The invention includes all stereoisomers and both the racemic mixtures of such stereoisomers as well as the individual enantiomers that may be separated according to methods that are well known to those of skill in the art. In certain embodiments, the compounds of the present invention do not comprise more than three naturally occurring amino acids, preferably no more than two naturally occurring amino acids, even more preferably no more than one naturally occurring amino acid.

Conjugates comprising the shared epitope-, shared epitope antagonist-containing peptide or shared epitope motif-containing peptides, analogues, derivatives, or mimetics linked to at least one additional moiety are also contemplated. The additional moiety may be a carrier molecule, to facilitate delivery of the conjugate to the appropriate target organ or tissue. In some embodiments, the conjugates are contemplated for delivery to the brain, for example, across the blood brain barrier. In other embodiments, the conjugates are contemplated for enhanced permeability for topical administration (for example, topical administration over a joint affected by rheumatoid arthritis).

A variety of carrier molecules are contemplated, and may vary, depending on the desired delivery or administration format. Among the carrier molecules contemplated are lipophilic or hydrophobic moieties, antibodies (and fragments thereof) and polyamines, although additional carrier molecules are also considered.

Conjugates of the shared epitope-, or shared epitope motif-containing peptides, analogues, derivatives, mimetics or antagonsits comprising the compounds of interest coupled to a lipophilic moiety are contemplated in some embodiments. U.S. Pat. No. 5,972,883 to Gozes et al., herein incorporated by reference, describes a lipophilic moiety conjugated to vasoactive intestinal peptide (or analogues and derivatives), as shown in Formula I of Gozes et al. [supra]. The present invention contemplates adapting Formula I of Gozes et al. [supra] for conjugation of at least one lipophilic moiety to an shared epitope-containing peptide, shared epitope motif-containing peptide, analogue, derivative, mimetic or antagonsits as shown below.

$R^1$—$Y^1$-[shared epitope- or shared epitope motif-containing peptide, derivative, analogue, mimetic, antagonist]-$Y^2$—$R^2$  (Formula (I))

$R^1$ and $R^2$ may be the same or different and each is hydrogen, a saturated or unsaturated lipophilic group or a $C_1$–$C_4$ hydrocarbyl or carboxylic acyl, with the proviso that at least one of $R^1$ and $R^2$ is a lipophilic group;

$Y^1$ and $Y^2$ may be the same or different, and each is —$CH_2$— or a bond in case the associated $R^1$ or $R^2$ is hydrogen and y1 may further be —CO—.

The lipophilic moiety which is coupled to the shared epitope- or shared epitope motif-containing peptides, analogues, derivatives, mimetics and antagonists is preferably a saturated or unsaturated radical such as hydrocarbyl or carboxylic acyl having at least 5 carbon atoms. The lipophilic moiety can be attached at either or both of the N-terminus and C-terminus of the peptide molecule.

In one preferred embodiment, the shared epitope- or shared epitope motif-containing peptides, analogues, derivatives, mimetics and antagonists are peptides of the Formula (I) above, in which $Y^1$ is —CO— and $R^1$ is a $C_5$–$C_{17}$ alkyl, with $Y^1R^1$ being, for example, stearoyl, lauroyl or caproyl, $Y^2$ is a bond and $R^2$ is hydrogen. Gozes et al. (supra) found stearoyl conjugates of vasoactive intestinal peptide derivatives to reach the brain following nasal administration.

In other embodiments, said conjugates comprise a long chain aliphatic carboxylic acid, as described in U.S. Pat. No. 5,147,855 to Gozes et al., herein incorporated by reference. Said long chain aliphatic carboxylic acid conjugate may have the long chain aliphatic carboxylic acid conjugated to the N terminus or to the C terminus. The long chain aliphatic carboxylic acid is a hydrophobic moiety having the formula —$CH_3(CH_2)_nCO$, wherein n is an integer from 6–16. In one embodiment, the long chain aliphatic carboxylic acid is a stearyl group conjugated to the shared epitope- or shared epitope motif-containing peptides, analogues, derivatives, mimetics and antagonists.

In other embodiments, the shared epitope- or shared epitope motif-containing peptides, analogues, derivatives, mimetics and antagonists may be conjugated with other molecules. In some embodiments, the other molecules may be carrier molecules, such as peptides or antibodies. For example, U.S. Pat. No. 4,902,505 to Pardridge et al., herein incorporated by reference, describes chimeric peptides suitable for neuropeptide delivery through the blood brain barrier. Briefly, such peptides include a peptide which by itself is capable of crossing the blood brain barrier by transcytosis at a relatively high rate, which is conjugated to a peptide which is only transportable at a very low rate into the brain across the blood brain barrier. Such chimeric peptides are useful in delivery of peptides (such as shared epitope- or shared epitope motif-containing peptides, derivatives, analogues) to the brain. Suitable blood brain barrier transportable peptides for use in such conjugates include histone, insulin, transferrin, insulin-like growth factor I, insulin-like growth factor II, basic albumin (or cationized albumin) and prolactin. The chimeric peptide conjugates are made by conjugating a transportable peptide with the shared epitope- or shared epitope motif-containing peptides, derivatives and analogues. The conjugation may be carried out using bifunctional reagents which are capable of reacting with each of the peptides and forming a bridge between the two. A preferred method of conjugation involves peptide thiolation, wherein the two peptides are treated with a reagent such as N-succinimidyl 3-(2-pyridylthio) propionate to form a disulfide bridge between the two peptides to form the chimeric conjugate. Other known conjugation agents may be used, so long as they provide the linkage of the two peptides together without denaturing them. Preferably, the linkage can be easily broken once the chimeric peptide conjugate has entered the brain. Suitable examples of conjugation reagents include glutaraldehyde and cystamine and EDAC. The conjugates comprising an shared epitope- or shared epitope motif-containing peptide, analogue, derivative, mimetic or antagonist may comprise a formulation further comprising pharmaceutically acceptable carriers and vehicles.

In other embodiments, the carrier molecule conjugated to the shared epitope- or shared epitope motif-containing peptides, analogues, derivatives, mimetics and antagonists is an antibody. In some embodiments, the antibody is a cationized antibody. U.S. Pat. Nos. 5,004,697 and 5,130,129, both by Pardridge and herein incorporated by reference, describe the cationization of antibodies to raise their isoelectric point in order to increase their rate of transport across the blood-brain barrier.

The use of an anti-transferrin receptor monoclonal antibody (OX26) as a carrier for a vasoactive intestinal peptide (VIP) analogue is described in Bickel et al. [*Proc. Natl. Acad. Sci. USA* 90:2618–2622 (1993)]. The OX26 antibody was conjugated to avidin, and this conjugate was then conjugated to a biotinylated VIP analogue. Bickel et al. [supra] note that the high concentration of transferrin receptors on brain capillary endothelia results in antibody targeting to the brain by receptor mediated transcytosis through the blood brain barrier. Bickel et al. [supra] noted an in vivo central nervous system effect (increased cerebral blood flow) following systemic infusion of the carrier-conjugate in rats, but no effect following systemic infusion of the biotinylated VIP analogue without the carrier antibody. As noted by Bickel et al. [supra], such a targeting system could be adapted for delivery of other drugs to the brain. Thus, transport of shared epitope- or shared epitope motif-containing peptides, analogues, derivatives, antagonists and mimetics to the brain or joint is contemplated. For example, biotinylation of a shared epitope- or shared epitope motif-containing peptide, derivative, analogue or mimetic would permit conjugation to an avidin-conjugated anti-transferrin receptor antibody, either monoclonal or polyclonal. Thus, in some embodiments, a biotinylated shared epitope- or shared epitope motif-containing peptide, analogue, derivative, mimetic or antagonist is contemplated. In other embodiments, said biotinylated peptides, analogues, mimetics or antagonists are further conjugated to an antibody. Said antibody may be specific for the transferrin receptor, and may be a monoclonal or polyclonal antibody preparation. The monolconal or polyclonal antibody to the transferrin receptor may recognize the human transferrin receptor, or it may recognize the transferrin receptor of another subject species (for example, rat, mouse or a non-human primate). In other embodiments, said conjugation to an antibody is accomplished by using a chemical crosslinker, rather than through a biotin-avidin linkage.

In yet other embodiments, the shared epitope- or shared epitope motif-containing peptides, analogues, derivatives, mimetics and antagonists are in the form of conjugates with a carrier molecule comprising a naturally occurring polyamine, such as putrescine, spermidine or spermine. Conjugates of neurologically active compounds with a polyamine carrier molecule are described in U.S. Pat. No. 5,670,477 to Poduslo et al., herein incorporated by reference. Suitable polyamines and linkages are described by Podsulo et al. [supra], and one of skill in the art may apply these to the shared epitope- or shared epitope motif-containing peptides, analogues, derivatives, mimetics and antagonists. In some embodiments, conjugates comprising a polyamine are in a formulation comprising pharmaceutically acceptable carriers and vehicles. While not limited to any particular formulation or any particular administration, in some embodiments, such formulations are suitable for parenteral delivery of the conjugates, while in other embodiments the formulation comprising the conjugates is suitable for intranasal administration of the conjugates.

D. Routes of Administration and Formulations

The present invention is not limited by the method of introduction of the therapeutic compound to the body. Among other methods, the present invention contemplates administering cutaneously, orally, or by standard injection (e.g. intravenous).

The present invention also contemplates administering shared epitope- or shared epitope motif-containing peptides, derivatives, mimetics, conjugates or antagonists to the patient intranasally or through respiratory inhalation. Formulations suitable for intranasal administration include ointments, creams, lotions, pastes, gels, sprays, aerosols, oils and other pharmaceutical carriers which accomplish direct contact between the compounds of the invention or a pharmaceutical composition comprising compounds of the invention and the nasal cavity. Examples of pharmaceutical compositions administered intranasally are described in U.S. Pat. Nos. 5,393,773 and 5,554,639 to Craig et al.; and U.S. Pat. No. 5,801,161 to Merkus, all herein incorporated by reference. Formulations suitable for respiratory inhalation include ointments, creams, lotions, pastes, gels, sprays, aerosols, oils and other pharmaceutical carriers which accomplish direct contact between compounds of the invention or a pharmaceutical composition comprising compounds of the invention and the respiratory tract. Examples of pharmaceutical compositions administered through respiratory inhalation are described in U.S. Pat. No. 4,552,891 to Hu et al.; U.S. Pat. No. 5,869,479 to Kreutner et al., and U.S. Pat. No. 5,864,037 to Chasis et al., all herein incorporated by reference.

In some embodiments, intranasal administration and respiratory inhalation are the preferred modes of administration due to the ease of administration and faster onset of therapeutic activity. It is contemplated that intranasal administration and respiratory inhalation are advantageous as they may allow a smaller effective dosage to be administered than would be possible with the oral route of administration. A preferred mode of administration comprises administration to the lung. Intrapulmonary delivery of pharmacologic agents to patients can be accomplished via aerosolization. Alternatively, the agent may be administered to the lung through a bronchoscope. Of course, the therapeutic agents may be investigated for their efficacy via other routes of administration, including parenteral administration.

While the present invention is not limited by the form of oral administration, aqueous and organic solutions of shared epitope- or shared epitope motif-containing peptides, derivatives, analogues, mimetics, conjugates or antagonists are contemplated. Likewise, compounds of the invention can be associated with a solid pharmaceutical carrier for solid oral administration (i.e., in pill form). One skilled in the art is able to readily prepare such solid formulations, and in one embodiment, the inactive ingredients include croscarmellose sodium, hydroxypropyl methylcellulose, lactose, magnesium stearate, methocel E5, microcrystalline cellulose, povidine, propylene glycol and titanium dioxide.

Compounds of the present invention (i.e. shared epitope- or shared epitope motif-containing peptides, derivatives, analogues, mimetics, conjugates or antagonists) may also be administered cutaneously in a carrier adapted for topical administration. Such carriers include creams, ointments, lotions, pastes, jellies, sprays, aerosols, bath oils, or other pharmaceutical carriers that accomplish direct contact between the compounds of the invention and the pore of the skin. In general pharmaceutical preparations may comprise from about 0.001% to about 10%, and preferably from about 0.01 to 5% by w/w of the active compound (e.g., shared epitope- or shared epitope motif-containing peptides, derivatives, analogues, mimetics, conjugates or antagonists) in a suitable carrier. In some cases it may be necessary to dissolve the active compound in an appropriate solvent such as ethanol or DMSO (dimethylsulfoxide), and the like, to facilitate incorporation into a pharmaceutical preparation.

While the present invention is not limited by a specific method of introducing compounds of the invention by injection, injection of the compounds of the invention can be carried out by any conventional injection means (e.g., employing an hypodermic syringe and needle or a similar device such as the NovolinPen. sold by Squibb-Novo, Inc., Princeton, N.J., USA). This injection may be by the subject injecting him or herself or by another person injecting the patient.

Compounds of the present invention (i.e. shared epitope- or shared epitope motif-containing peptides, derivatives, analogues, mimetics, conjugates or antagonists) can be introduced by injection in a physiologically acceptable composition. Such compositions are aqueous solutions that are physiologically acceptable for administration by injection. The physiologically acceptable carrier is selected such that it is not painful or irritating upon injection. The physiologically acceptable compositions will preferably be sterile at the time of administration by injection.

Among the physiologically acceptable compositions for use in the methods is physiological saline or phosphate buffered saline, in which compounds of the present invention are dissolved or suspended, such that the resulting composition is suitable for injection. Such a physiologically acceptable composition can also include a non-irritant preservative, such as, e.g., benzalkonium chloride at 0.05% (w/v) to 0./2% (w/v).

While the present invention is not limited to the method of injecting compounds of the present invention, in the preferred embodiment, it is injected with a standard syringe. One skilled in the art would be capable of injecting compounds of the present invention with a carrier as described above.

In some embodiments (e.g. in a method of treating a subject with one or more symptoms of AD), it is desirable that the compositions of the invention reach the brain, as this is the primary target organ for the neuroprotective therapy. While substances pass easily from the bloodstream to cells in other parts of the body, the brain has a complex set of defenses that protect it from possible poisons. Known as the blood-brain barrier (BBB), these defenses include physical barriers, such as tightly opposed cells in the walls of the blood vessels. Another defense is chemical-enzymes that act as gatekeepers, escorting only certain substances into the inner compartments.

In some embodiments, targeting of the shared epitope- or shared epitope motif-containing peptide, derivative, analogue, antagonist or mimetic to the brain is desired. In such cases, delivery across the blood-brain barrier is necessary. As described above, conjugates comprising an shared epitope- or shared epitope motif-containing peptide, derivative, analogue, antagonist or mimetic and a carrier molecule are useful in such embodiments. As described above, the carrier molecule of the conjugate may be lipophilic moiety, a transportable peptide (including, but not limited to a histone, insulin, transferrin or basic albumin), an antibody (including, but not limited to an anti-transferrin receptor antibody) or a polyamine.

Such conjugates may be administered by any route for delivery across the blood-brain barrier. In some embodiments oral administration is contemplated. In other embodiments, parenteral administration is contemplated, including, but not limited to, intravenous injection. In yet other embodiments, intranasal administration, as an aerosol, is contemplated. Intranasal administration permits penetration of the aerosol composition to the CNS through the olfactory nerve. As described above, any pharmaceutical carrier that can be used as a vehicle for the administration of the conjugates comprising an shared epitope- or shared epitope motif-containing peptide, analogue, derivative, mimetic or antagonist and a carrier for delivery across the blood-brain barrier is contemplated for the pharmaceutical compositions.

In other embodiments, delivery to the brain across the blood-brain barrier is accomplished by direct delivery to the brain. In some embodiments, delivery to the brain is accomplished by using a subcutaneously implantable infusion reservoir and pump system, as described in U.S. Pat. No. 4,588,394 to Schulte et al., herein incorporated by reference. The implantable infusion reservoir and pump system of Schulte et al. [supra] includes a variable capacity reservoir for receiving and storing fluids containing medications for delivery to a catheter which directs the medications to a specific infusion location in the body. A pump and valving arrangement is interposed between the reservoir and the catheter to facilitate and control the transfer of the medications from the reservoir to the catheter in a safe and efficient manner. Schulte et al. [supra] describes placement of the catheter in the body for the delivery of morphine or other pain killing medications directly into the lateral ventricle of the brain in the treatment of terminally ill patients. One of skill in the art would be able to use and adapt the implantable infusion reservoir and pump system of Schulte et al. [supra] for the direct administration of shared epitope- or shared epitope motif-containing peptides, analogues, derivatives, mimetics, conjugates and antagonists directly to the brain of a subject. In some embodiments, such administration is contemplated for the treatment of Alzheimer's disease.

Another pump system which may be used in delivering shared epitope- or shared epitope -motif containing peptides, analogues, derivatives, conjugates, mimetics and antagonists directly to the brain is described in U.S. Pat. No. 6,042,579 to Elsberry et al., herein incorporated by reference. Elsberry et al. [supra] describe a method of treatment of a neurodegenerative disorder by means of an implantable pump and a catheter having a proximal end coupled to the pump and having a discharge portion for infusing into the brain therapeutic dosages of one or more nerve growth factors. The catheter is implanted in the brain so that the discharge portion lies adjacent to a predetermined infusion site of the brain, such as the neuropil, the intraventricular space, or the subarachnoidal space. One skilled in the art would be able to use and adapt the system and method described by Elsberry et al. [supra] for the administration of shared epitope- or shared epitope motif-containing peptides, analogues, derivatives, mimetics, conjugates or antagonists directly to specific regions of the brain of a subject.

Another implantable system is described in U.S. Pat. No. 5,643,207 to Rise, herein incorporated by reference. Rise [supra] describes an implantable system for infusing an agent into an organ containing an endogenous fluid, including an implantable reservoir for the agent and implantable first and second catheters implanted into the organ. An implantable pump transmits the endogenous fluid to the organ through one catheter and returns it through the other catheter. A predetermined quantity of the agent is added from the reservoir to the endogenous fluid to facilitate buffering and dilution of the agent before administration to the organ. One of skill in the art would be able to use and adapt the system described by Rise [supra] for administration of shared epitope- or shared epitope motif-containing peptides, analogues, derivatives, conjugates, mimetics and antagonists directly to the brain of a subject.

As an alternative to implantable pump systems, an implantable therapy system is contemplated in some embodiments. U.S. Pat. No. 6,179,826 B1 to Aebischer et al., herein incorporated by reference, describes an implantable, retrievable therapy device useful for the sustained and controlled delivery of a biologically active factor to a subject, and more particularly, a device which can deliver a biologically active factor to a localized region in the central nervous system of a subject. A biocompatible vehicle containing a biologically active factor is inserted and positioned at the treatment site. Biocompatible vehicles and systems for the positioning and implantation of the biocompatible vehicles containing a biologically active factor are described by Aebischer et al. [supra] and may be used and adapted by one of skill in the art for the administration of shared epitope- or shared epitope motif-containing peptides, analogues, derivatives, conjugates, mimetics or antagonists to the brain of a subject.

In other embodiments, a polymeric delivery system for the delivery of shared epitope- or shared epitope motif-containing peptides, analogues, derivatives, mimetics, conjugates and antagonists is contemplated. Such a system is described in U.S. Pat. No. 5,601,835 to Sabel et al., herein incorporated by reference. The delivery system is preferably implanted in the central nervous system for delivery directly to the central nervous system for the treatment of disorders. Continuous delivery directly into the brain for an extended time period can be achieved with these systems. The delivery device is a two-phase system that is manufactured using standard techniques such as blending, mixing or the equivalent thereof, following selection of the material to be delivered and an appropriate polymer for formation of the matrix. The active substance is dispersed within the devices to create channels and pores to the surface for release of the active substance at the desired rate. One of skill in the art would be able to use and adapt the polymeric drug delivery systems of Sabel et al. [supra] for the delivery of shared epitope- or shared epitope motif-containing peptides, analogues, mimetics, conjugates and antagonists directly to the brain of a subject.

In addition to the methods for delivering shared epitope- or shared epitope motif-containing peptides, derivatives, analogues, conjugates, mimetics and antagonists across the blood brain barrier described above, one of skill in the art will recognize that there are numerous other delivery systems suitable for delivery across the blood brain barrier, and that any suitable method may be employed in the methods of treatment described herein. For example, drug (or active substance) nanoparticles may be employed, as described in U.S. Pat. No. 6,117,454 to Kreuter et al., herein incorporated by reference.

Alternatively, a redox chemical delivery system, as described in U.S. Pat. Nos. 5,624,894; 5,525,727 and 5,618,803 to Bodor, herein incorporated by reference, may also be used. For example, a redox targetor (such as, for example, a dihydropyridine/pyridinium salt redox carrier) is linked to the substance of interest (such as, for example, an shared epitope- or shared epitope motif-containing peptide, derivative, analogue, mimetic or antagonist), and in its reduced form, can transport the substance of interest across the blood brain barrier. Once across the blood brain barrier, oxidation of the redox targetor effectively traps the substance of interest in the brain. Enzymatic processes in the brain result in sustained release of the substance of interest within the brain.

Similarly, liposomes may be employed for passage across the blood brain barrier, as described in U.S. Pat. No. 6,132,764 to Li et al., herein incorporated by reference. The liposomes may be polymerized, or may have targeting molecules at their surface to promote delivery to particular organs. Block copolymers, which form micelles, can also be employed, as described in U.S. Pat. No. 6,153,193 to Kabanov et al., herein incorporated by reference. Thus, one of skill in the art can take advantage of a plurality of delivery systems appropriate for directing shared epitope- or shared epitope motif-containing peptides, derivatives, analogues, mimetics, conjugates or antagonists across the blood brain barrier to the brain.

In other embodiments (e.g. in a method of treating a subject with symptoms of RA), it is desirable that the compositions of the invention reach the affected joints. In some embodiments, this may be accomplished by cutaneous or transdermal application of pharmaceutical compositions comprising the compounds of the invention (e.g. antagonists of shared epitope- or shared epitope motif-containing peptides) directly to the skin over the affected joint. In other embodiments, delivery of the compounds to the affected joints may be by direct injection into the joint. The present invention specifically contemplates intra-articular injections in RA patients.

To perform an arthrocentesis, the specific area of the joint to be injected is palpated and is then marked, e.g., with firm pressure by a ballpoint pen that has the inked portion retracted. This will leave an impression that will last 10 to 30 minutes. (The ballpoint pen technique can also be used with soft tissue injection.) The area to be aspirated and/or injected should be carefully cleansed with a good antiseptic, such as one of the iodinated compounds. Then the needle can be inserted through the ballpoint pen impression.

Helpful equipment includes the following items: alcohol sponges; iodinated solution and surgical soap; gauze dressings (2×2); sterile disposable 3-, 10- and 20-ml syringes; 18- and 20-gauge, 1½-inch needles; 20-gauge spinal needles; 25-gauge, ⅝-inch needles; plain test tubes; heparinized tubes; clean microscope slides and coverslips; heparin to add to heparinized tubes if a large amount of inflammatory fluid is to be placed in the tube; fingernail polish to seal wet preparation; chocolate agar plates or Thayer-Martin medium; tryptic soy broth for most bacteria; anaerobic transport medium (replace periodically to keep culture media from becoming outdated); tubes with fluoride for glucose; plastic adhesive bandages; ethyl chloride; hemostat; tourniquet for drawing of simultaneous blood samples; and 1 percent lidocaine.

Knee. The knee is the easiest joint to inject. The patient should be in a supine position with the knee fully extended. The puncture mark is made just posterior to the medial portion of the patella, and an 18- to 20-gauge, 1½-inch needle directed slightly posteriorly and slightly inferiorly. The joint space should be entered readily. On occasion thickened synovium or villous projections may occlude the opening of the needle, and it may be necessary to rotate the needle to facilitate aspiration of the knee when using the medial approach. An infrapatellar plica, a vestigal structure that is also called the ligamentum mucosum, may prevent adequate aspiration of the knee when the medial approach is used. However, the plica should not adversely affect injections or aspirations from the lateral aspect.

Shoulder. Injections in the shoulder are most easily accomplished with the patient sitting and the shoulder externally rotated. A mark is made just medial to the head of the humerus and slightly inferiorly and laterally to the coracoid process. A 20- to 22-gauge, 1½-inch needle is directed posteriorly and slightly superiorly and laterally. One should be able to feel the needle enter the joint space. If bone is hit, the operator should pull back and redirect the needle at a slightly different angle.

The acromioclavicular joint may be palpated as a groove at the lateral end of the clavicle just medial to the shoulder. A mark is made, and a 22- to 25-gauge, ⅝- to 1-inch needle is carefully directed inferiorly. Rarely is synovial fluid obtained.

The sternoclavicular joint is most easily entered from a point directly anterior to the joint. Caution is necessary to avoid a pneumotharax. The space is fibrocartilaginous, and rarely can fluid be aspirated.

Ankle Joint. For injections of the compounds of the present invention in the ankle joints, the patient should be supine and the leg-foot angle at 90 degrees. A mark is made just medical to the tibialis anterior tendon and lateral to the medial malleolus. A 20- to 22-gauge, 1½-inch needle is directed posteriorly and should enter the joint space easily without striking bone.

Subtalar Ankle Joint. Again, the patient is supine and the leg-foot angle at 90 degrees. A mark is made just inferior to the tip of the lateral mallcolus. A 20- to 22-gauge, 1½-inch needle is directed perpendicular to the mark. With this joint the needle may not enter the first time, and another attempt or two may be necessary. Because of this and the associated pain, local anesthesia maybe helpful.

Wrist. This is a complex joint, but fortunately most of the intercarpal spaces communicate. A mark is made just distal to the radius and just ulnar to the so-called anatomic snuff box. Usually a 24- to 26-gauge, ⅝ to 1-inch needle is adequate, and the injection is made perpendicular to the mark. If bone is hit, the needle should be pulled back and slightly redirected toward the thumb.

First Carpometacarpal Joint. Degenerative arthritis often involves this joint. Frequently the joint space is quite narrowed, and injections may be difficult and painful. A few simple maneuvers may make the injection fairly easy, however. The thumb is flexed across the palm toward the tip of the fifth finger. A mark is made at the base of the first metacarpal bone away from the border of the snuff box. A 22- to 26-gauge, ⅝ to 1-inch needle is inserted at the mark and directed toward the proximal end of the fourth metacarpal. This approach avoids hitting the radial artery.

Metacarpophalalangeal Joints and Finger Interphalangral Joints. Synovitis in these joints usually causes the synovium to bulge dorsally, and a 24- to 26-gauge, ½ to ⅝-inch needle can be inserted on the either side just under the extensor tendon mechanism. It is not necessary for the needle to be interposed between the articular surfaces. Some prefer having the fingers slightly flexed when injecting the metacarpophalangeal joints. It is unusual to obtain synovial fluid. When injecting, a mix of the compounds of the present invention with a small amount of local anesthetic is also contemplated.

Metatarsophalangeal Joints and Toe Interphalangeal Joints. The techniques are quite similar to those of the metacarpophalangeal and finger interphalangeal joints, but many prefer to inject more dorsally and laterally to the extensor tendons. Marking the area(s) to be injected is helpful as is gentle traction on the toe of each joint that is injected.

Elbow. A technique preferred by many is to have the elbow flexed at 90 degrees. The joint capsule will bulge if there is inflammation. A mark is made just below the lateral epicondyle of the humerus. A 22-gauge, 1 to 1½-inch is inserted at the mark and directed parallel to the shaft of the radius or directed perpendicular to the skin.

Hip. This is a very difficult joint to inject even when using a fluoroscope as a guide. Rarely is the physician quite sure that the joint has been entered; synovial fluid is rarely obtained. Two approaches can be used, anterior or lateral. A 20-gauge, 3½-inch spinal needle should be used for both approaches.

For the anterior approach, the patient is supine and the extremity fully extended and externally rotated. A mark should be made about 2 to 3 cm below the anterior superior iliac spine and 2 to 3 cm lateral to the femoral pulse. The needle is inserted at a 60 degree angle to the skin and directed posteriorly and medially until bone is hit. The needle is withdrawn slightly, and possibly a drop or two of synovial fluid can be obtained, indicating entry into the joint space.

Many prefer the lateral approach because the needle can "follow" the femoral neck into the joint. The patient is supine, and the hips should be internally rotated—the knees apart and toes touching. A mark is made just anterior to the greater trochanter, and the needle is inserted and directed medially and sightly cephalad toward a point slightly below the middle of the inguinal ligament. One may feel the tip of the needle slide into the joint.

Temporomandibular Joint. For injections, the temporomandibular joint is palpated as a depression just below the zygomatic arch and 1 to 2 cm anterior to the tragus. The depression is more easily palpated by having the patient open and close the mouth. A mark is made and, with the patient's mouth open, a 22-gauge, ½ to 1-inch needle is inserted perpendicular to the skin and directed slightly posteriorly and superiorly.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); µM (micromolar); N (Normal); mol (moles); mmol (millimoles); µmol (micromoles); nmol (nanomoles); gm (grams); mg (milligrams); µg (micrograms); L (liters); ml (milliliters); µl (microliters); cm (centimeters); mm (millimeters); µm (micrometers); nm (nanometers); C (degrees Centigrade); FSK (forskolin); SEM (standard error of the mean); Ci (Curies)

EXAMPLE 1

In this example, various assays used to detect intercellular and intracellular signaling events are presented.

Protein Kinase a Activity Assay

Protein kinase A (PKA) was measured using the Life Technologies™ Protein Kinase A (cAMP-dependent Protein Kinase) Assay System (Cat. No. 13128-012). The basis of the assay system is the use of a heptapeptide substrate and a 17-amino acid inhibitor peptide (which is valuable for proving PKA-specific protein kinase activity). Four assay conditions per experimental condition are recommended by the manufacturer (+/− inhibitor and +/− cAMP) to determine total PKA-specific kinase activity and proportion of PKA activated in the cells or tissue of interest. Briefly, the four parallel assay conditions are set up for each of the four assay conditions for a given cell or tissue sample, according to the manufacturer's instructions. Substrate and [$\gamma$-$^{32}$P]ATP (3000–6000 Ci/mmol stock solution) are then added to each tube, and incubated according to the manufacturer's instructions. Following the incubation period, a sample from each tube is spotted onto a nitrocellulose disc, which is the acid washed prior to scintillation counting (all according to the manufacturer's instructions). Activity can then be determined as described by the manufacturer of the kit.

cAMP Assay cAMP was determined by using an Amersham Pharmacia Biotech cAMP enzymeimmunoassay (EIA) system (code RPN 225). The reagents are prepared as described by the manufacturer (lysis reagents 1 and 2, the standard for the non-acetylation assay, the anti-cAMP antiserum, the cAMP peroxidase conjugate and wash buffer). Briefly, a microtiter plate is prepared as suggested by the manufacturer. Samples are added, followed by the antiserum solution. Following the recommended incubation, cAMP-peroxidase conjugate is added and incubated according to the recommended protocol. Each well is then aspirated and washed, and enzyme substrate is added and incubated. The results can then be read at 630 nm or at 450 nm (depending on the time of incubation and method of stopping the reaction), again according to the manufacturer's protocol.

cGMP Assay cGMP was determined using an Amersham Pharmacia Biotech cGMP enzymeimmunoassay (EIA) system (Code RPN 226). The reagents (lysis reagents, standards, antibody, cGMP conjugate and wash buffer) are all prepared according to the manufacturer's instructions. Briefly, samples are acetylated with acetylation reagent (acetic anhydride in triethylamine) and then incubated with the antibody reagent and lysis buffer according to the manufacturer's instructions. The cGMP conjugate is then added and the microtiter plate is incubated according to the manufacturer's instructions. The wells are aspirated and washed, enzyme substrate is added and incubated, and the plate can be read at 630 nm or 450 nm (depending on the length of incubation and how the reaction was terminated). Controls are carried out as recommended by the manufacturer, and the results are calculated according to the manufacturer.

Nitrate/Nitrite Assay

Nitrate/Nitrite are assayed using the Cayman Chemical Company Nitrate/Nitrite Colorimetric Assay Kit (LDH Method) (Catalog No. 760871). Briefly, the assay uses an excess of NADPH, an essential cofactor for the nitric oxide synthase enzyme (NOS), and then uses lactate dehydrogenase (LDH) to destroy the excess NADPH. NOS activity, as well as nitrate and nitrite in urine, plasma, serum and tissue culture medium can all be assayed with this kit. Nitrite and nitrate measurement are carried out as described by the manufacturer, which includes a nitrate standard curve. S amples are added to assay buffer in microtiter wells, followed by NADPH and nitrate reductase mixture. The samples are then incubated for 40 or 60 minutes at room temperature (depending on the sample). Cofactor solution and LDH solution are then added and incubated for 20 minutes at room temperature. Greiss reagents are then successively added, and the absorbance at 540 or 550 nm is read following a 10 minute incubation at room temperature. All steps are carried out according to the manufacturer's protocol. Calculations of nitrate and nitrite are then carried out as described by the manufacturer.

Comet Assay

In related studies, the inventors have found that DNA repair proteins (See Wu et al., *Mutation Research* 546: 93–102, 2004) and activity can be induced through extracellular signaling. To further determine the signaling pathways involved in DNA repair induction, the inventors used the Trevigen CometAssay™ kit (Cat. No. 4250-50-K). The CometAssay is a single-cell gel electrophoresis method that can measure a variety of types of DNA damage, and repair of damage, in individual cells. The assay is based on the alkaline lysis of labile DNA at sites of damage. The unwound, relaxed DNA is able to migrate out of the cell during electrophoresis and can be visualized by SYBR Green staining. Cells that have accumulated DNA damage appear as fluorescent comets with tails of DNA fragmentation or unwinding, whereas normal undamaged DNA does not migrate far from the origin.

After cells have been preincubated with various compounds of interest, cells are collected, washed, and subjected to DNA damage with 100 µM $H_2O_2$ at 4° C. for 20 min. To quantify DNA damage, cells were collected and three parallel samples were processed (a negative control, a DNA damage control ($H_2O_2$) and a sample subjected to $H_2O_2$ following exposure to various modulators of the cAMP signaling pathway). Cells are then washed in PBS. The washed cells are combined with molten low-melting agarose (Trevigen Cat. No. 4250-50-02) and transferred to a CometSlide™ (Trevigen Cat. No. 4250-100-03). The slides are immersed in lysis buffer for 30 min, on ice, in the dark. The slides are then treated with alkali buffer for 20 to 60 min at room temperature in the dark. The slides are then electrophoresed in buffer for 10 min at 20 volts, then fixed in methanol and ethanol. The slides are then stained with SYBR green (Trevigen Cat. No. 4250-50-05) solution and fluorescently imaged with a Diagnostic Instruments digitized camera, mounted on a Nikon Eclipse E400 microscope. Scion Image software is used to quantitate the comet tail intensity. Each data point is derived from tail fluorescent intensity determination in 50–100 individual cells. Data is presented as % DNA repair (the percent decrement in tail fluorescence intensity in agonist or antagonist-treated cells, relative to the intensity recorded in cells treated with $H_2O_2$ only)±SEM. (R.U.s)

The Comet Assay is an Accurate and Reproducible Readout System to Determine Signaling through the cAMP-PKA Pathway.

Figure 2:
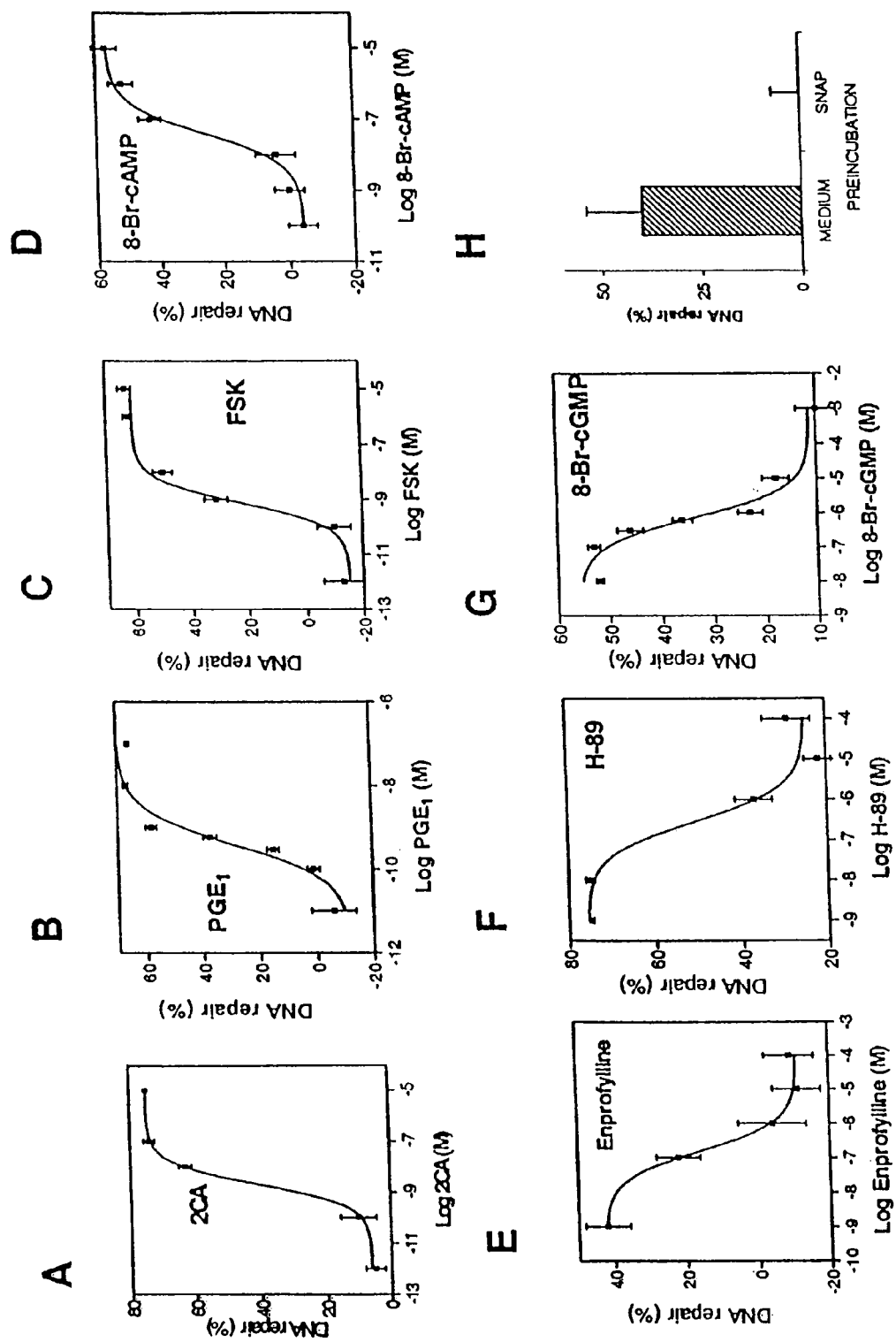
FIG. 2 depicts the experimental results confirming that inducible DNA repair signaling is transduced through a cAMP-dependent pathway.

Using this system, the inventors established that induction of DNA repair activity in normal cells is mediated by a Gs protein-coupled receptor-dependent pathway. As shown in FIG. 2, stimulation of the human fibroblastoid line M1 cells for 20 min with various concentrations of either prostaglandin E1 ($PGE_1$) (FIG. 2B), 2-chloro adenosine (2CA) (FIG. 2A), FSK (FIG. 2C) or 8-Br-cAMP (FIG. 2D) triggered in all cases DNA repair. M1 cells express the $A_{2b}$, but not the $A_{2a}$ subset of Gs protein-coupled adenosine receptors (data not shown). Indeed, as shown in FIG. 2, DNA repair activity, triggered by 10 µM 2CA, could be blocked by co-incubation with various concentrations of the adenosine receptor $A_{2b}$ antagonist, enprofylline (FIG. 2E) and by the non-selective adenosine receptor antagonist XAC, but not by the $A_{2a}$-selective antagonist, CSC (data not shown). 10 µM 2CA-triggered DNA repair could also be blocked by co-incubation with various concentrations of the specific PKA inhibitor, H-89, (FIG. 2F). Additionally, S-Nitroso-N-Acetylpenicillamine (SNAP), a NO donor, and a membrane-permeable cGMP analog, 8-Br-cGMP, completely blocked 10 µM 2CA-induced DNA repair (FIG. 2H and FIG. 2G, respectively).

Figure 3:
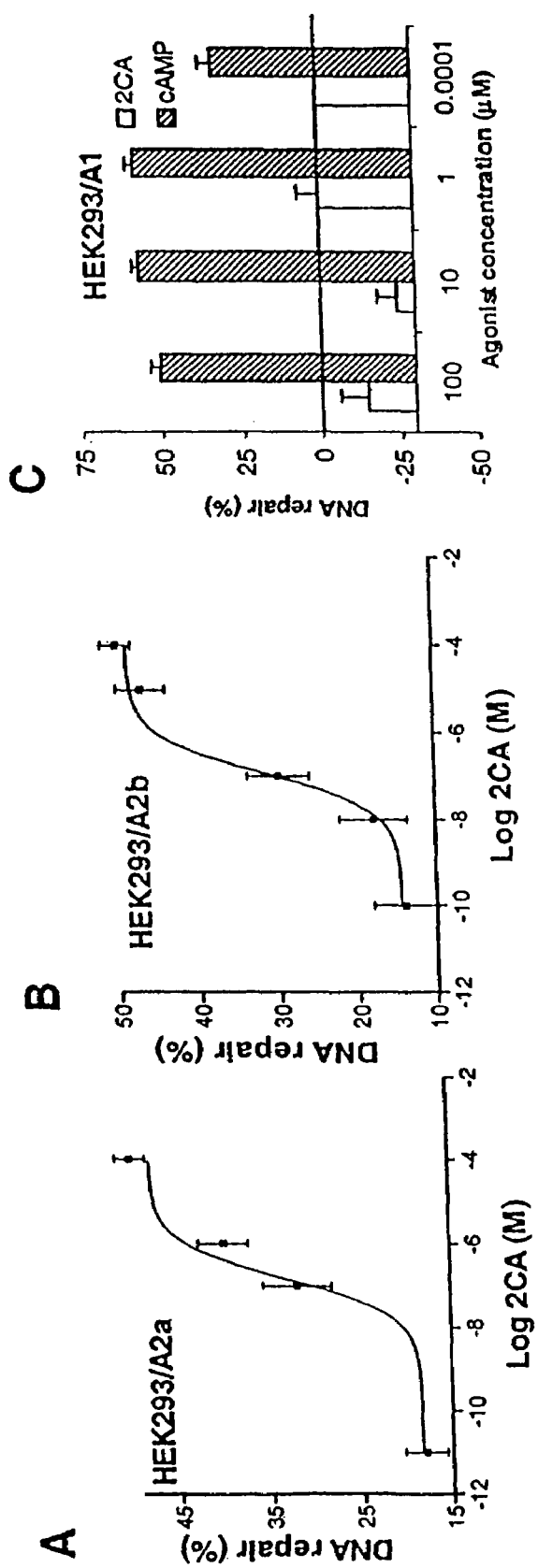
FIG. 3 depicts the experimental results assessing the role of Gs protein-coupled receptors in the inducible DNA repair signaling.

The extracellular signaling is transduced by Gs-protein coupled receptors, as evidenced by using adenosine receptor type-selective agonists and antagonists (not shown), and more conclusively, by using HEK293 cell transfectants (FIG. 3).

Human embryonic kidney 293 cells (HEK 293) transfected with adenosine receptors were provided by Joel Linden. The preparation of the HEK 293 transfectants is described in Linden et al. [Molecular Pharmacology 56:705–713 (1999)]. Briefly, the procedure carried out, as described in Linden et al. [supra] involved subcloning the cDNA for human $A_1$ adenosine receptor, human $A_{2B}$ adenosine receptor or human $A_{2A}$ adenosine receptor into the expression plasmid CLDN10B. The plasmids were amplified in competent JM109 cells and plasmid DNA isolated by using Wizard Megaprep columns (Promega Corporation, Madison, Wis.). Recombinant vectors were introduced into HEK 293 cells by lipofectin. Colonies were selected by growth of cells in 0.6 mg/ml G418. Stably transfected cells were maintained in Dulbecco's modified Eagle's medium/Ham's F12 medium with 10% fetal calf serum, 100 U/ml penicillin, 100 µg/ml streptomycin and 0.3 mg/ml G418.

Cells were pretreated for 20 min with various doses of 2CA before exposure to 100 µM $H_2O_2$ as above. As can be seen, HEK293 cell transfectants expressing the Gs-coupled adenosine receptors, $A_{2a}$ (FIG. 3A) or $A_{2b}$ (FIG. 3B), but not the Gi protein-coupled adenosine receptor A1 (FIG. 3C), transduced the signal. HEK293 cells transfected with $A_1$ adenosine receptors were not inherently resistant to cAMP signaling, as pretreatment with various doses of a membrane-permeable cAMP analog, 8-Br-cAMP triggered comparable responses in those cells (FIG. 3C).

Thus, it is concluded that under physiological conditions, DNA repair activity can be induced either by extracellular agonists capable of signaling through Gs-coupled receptors, or by agents capable of intracellular activation of the cAMP-PKA pathway. This system allows highly reproducible detection of intracellular cAMP concentration shifts at a sub-nanomolar range, and is highly sensitive to both cAMP and NO changes and as such is suitable for accurate determination of cAMP and NO signaling events.

It is noteworthy that recent studies have demonstrated increased expression and enzymatic activity of DNA excision repair proteins in brain tissues of AD patients. It has been suggested that the pathology seen in AD may represent an excessive effort to repair aging-related DNA damage (discussed in Schmitz C et al. [*Acta Neuropathol* 97:71–81 (1999)]). Relevant to this notion, ERCC1 and 2 (excision repair proteins), APLP1 and ApoE are all located on chromosome 19q13 in an intriguingly close proximity. It is of interest that RA, which has been found to associate with reduced DNA repair activity [McCurdy D et al. *Radiat Res* 147:48–54 (1997); Colaco CB et al. *Clin Exp Immunol* 72:15–19 (1988)], has also been shown to protect against AD. Thus, it is conceivable that the comet assay system described above is not only an accurate and convenient readout system for intracellular cAMP-dependent signaling events, but may also be directly relevant to the pathogenesis of AD.

EXAMPLE 2

In this example, results of experiments carried out are presented to demonstrate that shared epitope-expressing cells have impaired cAMP signaling.

Given the negative association between RA and AD and the postulated role of the cAMP-PKA pathway in the latter disease, it was of interest to determine the efficiency of signaling through that pathway in RA. As can be seen in FIG. 1A, lymphoblastoid B cell lines from 23 patients with RA displayed markedly lower PKA activation following stimulation with forskolin (FSK), compared to the control group of 16 healthy controls. PKA activation was determined 14 minutes following stimulation with 25 μM FSK. Results are shown as percent of maximal activity, relative to the response with the manufacturer's control (cAMP) provided with the kit. Similarly, PKA activation by $PGE_1$ in lymphoblastoid lines from 8 RA patients was significantly lower than the activation in 5 normal lines (p<0.001, data not shown). Equally diminished responses could be found in freshly isolated peripheral blood T cells of RA patients, compared to healthy controls (data not shown).

To assess the role of the RA shared epitope, homozygous tissue-typing lines expressing either the DRB1*0401 or DRB1*0404 alleles were tested. As shown in FIG. 1A, shared epitope-expressing lines displayed resistance to PKA activation, similar to the RA group. Control lines, homozygous for other DRB1 alleles showed normal FSK-induced PKA activation (data not shown). PKA activation was determined 14 minutes following stimulation with 25 μM FSK. Results are shown as % of maximum activity, relative to the response with the manufacturer's positive control (cAMP) provided with the kit. Taken together, these results demonstrate an association between the RA shared epitope and the cAMP-PKA signaling pathway defect.

To more directly assess the role of the shared epitope in cAMP signaling, L cell transfectants expressing different DRβ*04 chains were used. The L cell transfectants were donated by Robert Karr, and are described in Drover et al. [*Human Immunology* 40:51–60 (1994)]. The transfectants, as described in Karr et al. [supra], are cells of the DAP.3 sublcone of the class-II-negative murine L-cell fibroblasts that had been transfected with DRB cDNA constructs as described in Klohe et al. [*J Immunology* 141:2158–2164 (1988)]. Briefly, Klohe et al. [supra] describe maintaining cells of the DAP.3 subclone of class II-negative murine L cell fibroblasts in Eagles MEM with 10% fetal calf serum and 2 mM glutamine. The cells were transfected using the calcium phosphate co-precipitation method, using 20 μg each of the plasmids containing the class II chain DNA and 1 μg of the pSV2-neo plasmid, which contains the neomycin resistance gene. The DNA precipitates were incubated with the cells for 18 hours before removal of the medium and replacement with fresh, complete medium. At 48 hours after addition of the DNA to the cells, the medium was removed and complete medium containing 1 mg/ml of the neomycin analog G418 was added. After 48 hours, the medium was removed and complete medium containing G418, 250 μg/ml, was added and was subsequently changed twice weekly. After the appearance of G418-resistant colonies of transfectants (2 to 3 weeks), the cells were detached from the tissue culture plastic with a trypsin-EDTA solution, and an aliquot of cells from each transfection was cultured overnight in selection media in a bacteriologic petri dish, and class II-expressing transfectants were identified by immunofluorescence.

As shown in FIG. 1B, transfectants L565 (expressing DRβ*0401; squares) and L300 (DRβ*0404; rhombus) showed markedly reduced FSK-induced PKA activation compared to L514 (DRβ*0402; not shown) and L259 (DRβ*0403; triangles). Cells were stimulated with FSK as above and PKA activity was determined at different time points. Thus, L cell transfectants expressing shared epitope-positive DRβ chains are unable to generate the antioxidative response. Data points represent the mean±SEM of 3–5 experiments.

Amino acids Q70 [Gln70], K/R71 [Lys/Arg71] and A74 [Ala74] have been previously identified as key residues in the shared epitope-related RA susceptibility. To examine the contribution of each of those residues to the observed signaling defect, L-cell transfectants with single point mutations in positions 70, 71 or 74 were used (FIG. 1C). Alleles *0404 and *0403 differ by a single amino acid in position 74, alanine versus glutamic acid, respectively. As can be seen, substitution of alanine 74 in DRβ*0404 to glutamic acid (thereby converting it to a DRβ*0403-like sequence; A74E [Ala74Glu]) restored PKA activation, while substitution of glutamic acid 74 with alanine in DRβ*0403 (converting it to DRβ*0404-like sequence; E74A [Glu74Ala]) caused inhibition of that kinase activity. Interestingly, substitution of glutamine to aspartic acid in position 70 (Q70D [Gln70Asp]) restored PKA activation in DRβ*0404 transfectants, while the same substitution in DRβ*0403 produced an opposite effect. Other substitutions examined are: R71K [Arg71Lys], substitution of arginine to lysine in position 71; R71E [Arg71Glu], substitution of arginine to glutamic acid in position 71. Data points represent the mean±SEM of 3–5 experiments of FSK-induced PKA activation in L-cells expressing either the wild type (WT) DRβ*0403 (closed bars), DRβ*0404 (open bars), or mutants thereof with single amino acid substitutions on the DRβ chain. Thus, the impact of residue 70 may be determined in the context of residue 74. The data presented here directly implicate for the first time the shared epitope in a signaling aberration.

Figure 4:
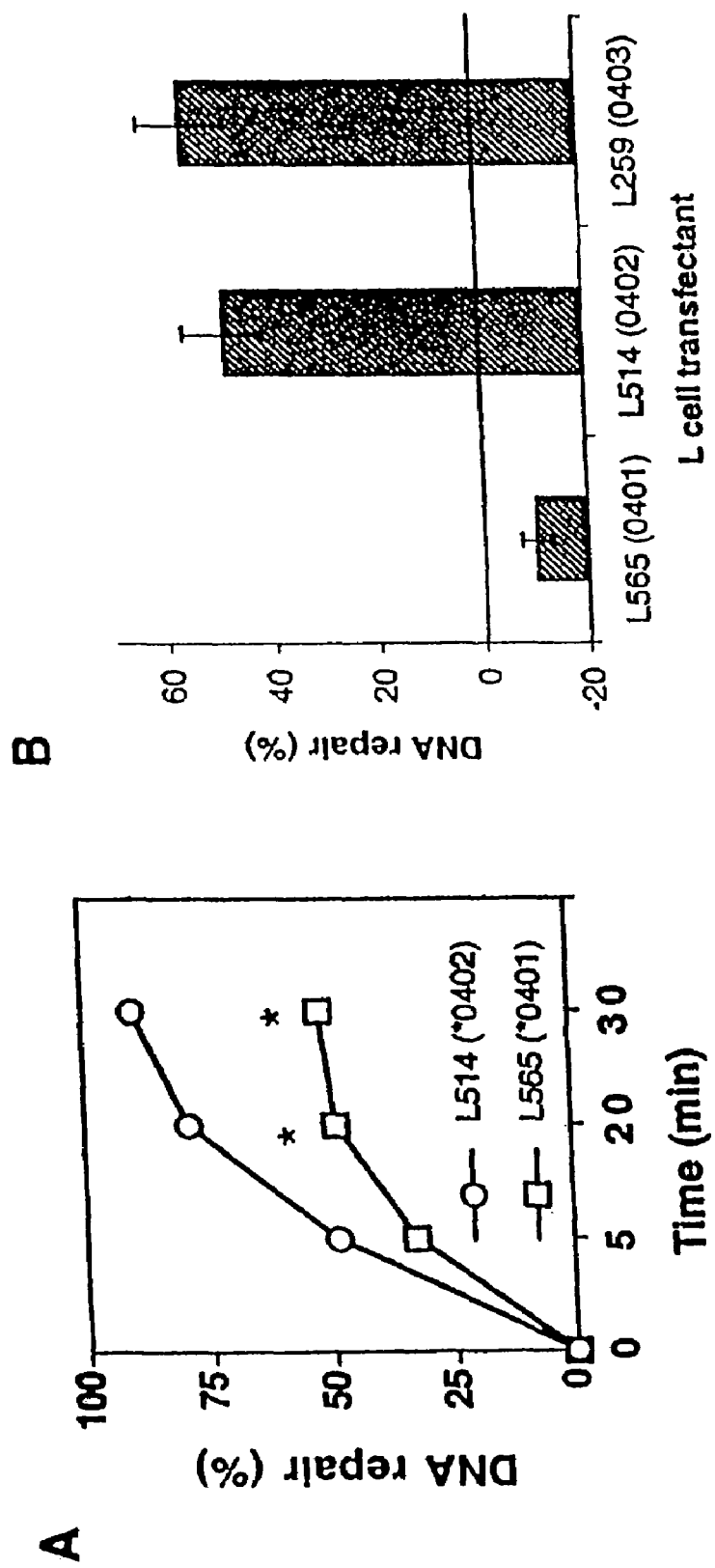
FIG. 4 depicts the experimental results demonstrating that shared epitope-expressing DRB1 alleles have a direct inhibitory effect on cAMP-dependent signaling.

As could be predicted from their diminished cAMP-mediated signaling, shared epitope-expressing cells displayed diminished DNA repair activity. FIG. 4A shows a time-course determination of spontaneous DNA repair activity following genotoxic damage by $H_2O_2$ in murine L cell transfectants expressing the DRβ*0401 (L565, squares), or DRβ*0402 (L514, circles) chains. Cells were treated with $H_2O_2$ and spontaneous DNA repair was determined as above at different time points. There was no significant difference in the extent of DNA damage at time zero between cell lines. However, as can be seen, L565 cells (DRB1*0401 transfectants) showed markedly reduced spontaneous repair ability over time compared to L514 (DRB1*0402) (FIG. 4A) and L259 (DRB1*0403) transfectants (FIG. 4B). In FIG. 4B, the L cell transfectants were pre-treated for 30 minutes with 10 μg/ml of cholera toxin before the induction of DNA damage with a 20 minute exposure to hydrogen peroxide and determining DNA repair as above. Similar patterns were observed in the human fibroblastoid line M1 expressing the DRβ*0401 chain (not shown). Additionally, protein extracts of lymphoblastoid B cell lines from RA patients and DRB1*0401 or *0404 homozygous tissue typing lines demonstrated much less efficient in-vitro repair of UV-damaged plasmids, compared to extracts from control lines (data not shown). Thus, it is concluded that cells expressing the RA-shared epitope display diminished spontaneous DNA repair activity.

EXAMPLE 3

In this example, results of experiments carried out to address the effects of shared epitope-containing peptides on cAMP-mediated DNA repair induction following application of such peptides to cells are presented.

Figure 1:
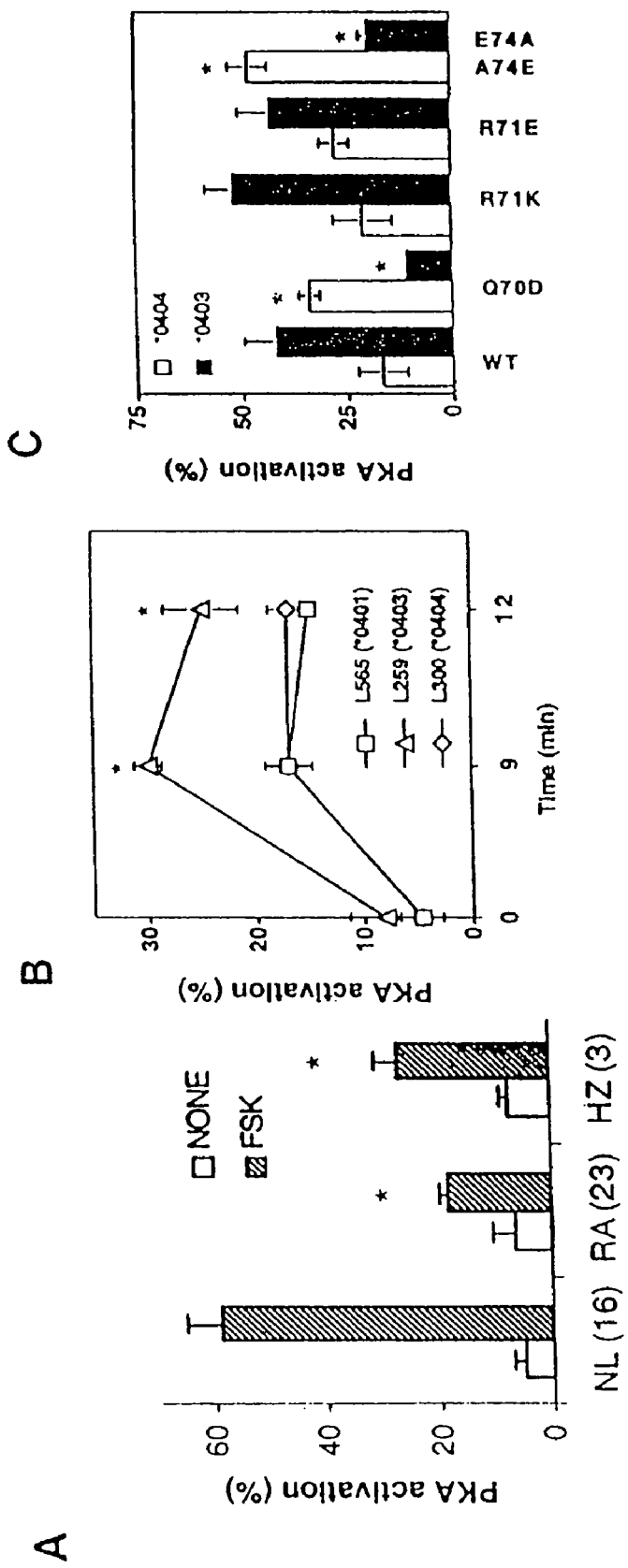
FIG. 1 depicts the impaired cAMP signaling exhibited in shared epitope-expressing cells.
Figure 5:
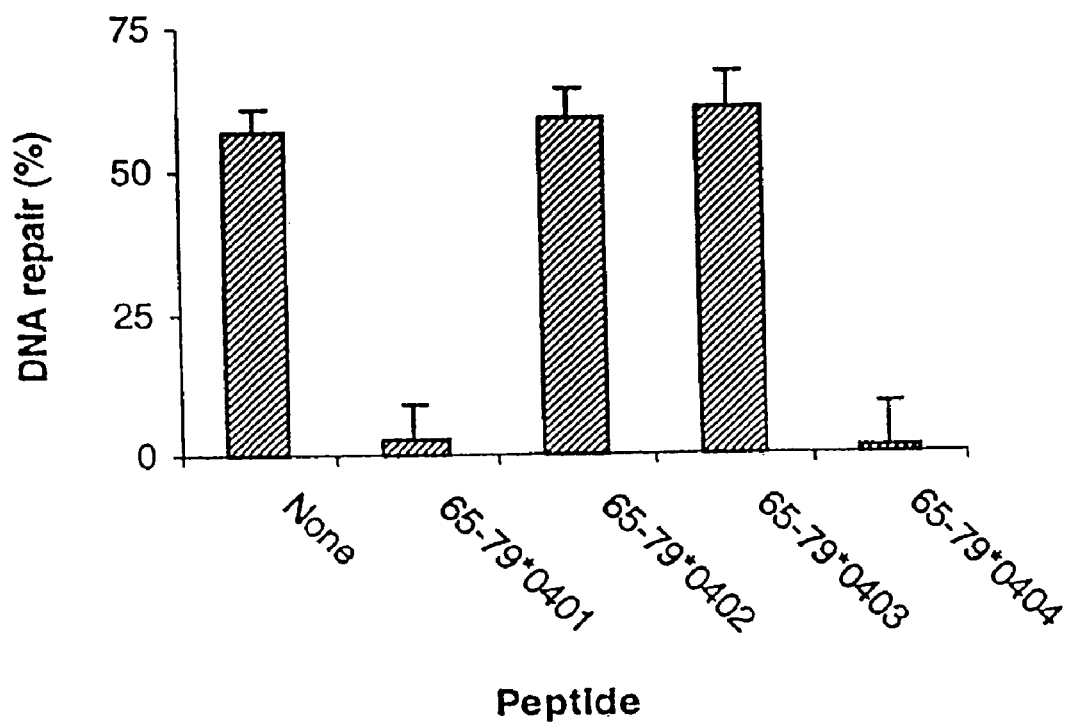
FIG. 5 is a bar graph that depicts the experimental results demonstrating that shared epitope-containing peptides inhibit cAMP-mediated DNA repair.

As suggested by the data shown in FIG. 1, the cAMP-inhibiting domain of the RA-shared epitope maps to the third allelic hypervariable region of the DRβ protein. To directly examine that possibility, cells were incubated overnight with synthetic peptides corresponding to the region contained within amino acids 65–79 and their ability to mount DNA repair activity in response to cAMP-elevating agents was determined. M1 cells were preincubated overnight with 50 μg/ml of synthetic peptides corresponding to the region surrounding the third allelic hypervariable region (aa 65–79) of each of the following DRβ chains: *0401 (65–79*0401) [SEQ ID NO: 5], *0402 (65–79*0402) [SEQ ID NO: 7], *0403 (65–79*0403) [SEQ ID NO: 9] or *0404(65–79*0404) [SEQ ID NO: 10]. At the end of the preincubation, cells were collected, washed and 2CA-induced DNA repair was determined as above. Table 3 (above) lists the different third allelic hypervariable region peptides used in the entire study disclosed here. As shown in FIG. 5, peptides corresponding to the third allelic hypervariable region of the RA-shared epitope-expressing DRB1 alleles *0401 [SEQ ID NO: 5] and *0404 [SEQ ID NO: 10], but not peptides corresponding to that region in the control alleles *0402 [SEQ ID NO: 7] or *0403 [SEQ ID NO: 9], inhibited cAMP-mediated DNA repair induction in both human (FIG. 5) and mouse cells (data not shown). The half-maximal inhibitory concentration ($IC_{50}$) of the 65–78*0401 [SEQ ID NO: 6] peptide was ~250 nM.

To determine whether the inhibitory activity by the RA shared epitope-derived peptides is due to an extracellular or intracellular effect, peptides conjugated to Sepharose beads were tested. Sepharose beads were chemically conjugated to 14-mer peptides corresponding to residues 65–78 of DRβ*0401 chain [SEQ ID NO: 6] (Beads*0401) or DRβ*0402 chain [SEQ ID NO: 8] (Beads*0402).

A modified method as described previously by Auger et al. [Nature Med 2:306–310 1996] was used. Briefly, cyanogen bromide activated Speharose 4B (1.5 ml) was washed with 1 mM HCl and incubated with peptides in 0.1 M $NaHCO_3$ and 0.5 M NaCl (pH 8) buffer overnight at 4° C. For each peptide, 5 mg was used per milliliter of Sepharose. Free Sepharose groups were blocked with 0.2 M glycine (pH 8) for 2 hours at room temperature. Columns were washed at 4° C. with the following buffers: 0.1 M $NaHCO_3$, 0.5 M NaCl (pH 8) buffer, then 0.5 M $CH_3COONa$ (pH 4) buffer and finally PBS at pH 7.5. M1 cells were plated at a density of $0.5 \times 10^6$ cells per well (6 well plate) in 10% FBS DMEM medium until 70–80% confluence. Prior to incubation with peptides, cultures were changed to serum-free DMEM medium, then evenly overlaid with 50 μg bead conjugated peptides, and incubated for the indicated period. Soluble peptides were added overnight to M1 cells at a concentration of 50 μg/ml.

M1 cells were preincubated for various times with bare Sepharose beads (Beads) or peptide-conjugated beads before 2CA-induced DNA repair assays were performed. As shown in FIG. 6, the conjugated peptide corresponding to residues 65–78 of the DRβ*0401 [SEQ ID NO: 6] protein, but not a peptide corresponding to the equivalent region on DRβ*0402 [SEQ ID NO: 8], blocked cAMP-mediated DNA repair. Complete inhibition could be seen as early as 10 minutes following incubation of human fibroblastoid cells with peptide-coated beads.

EXAMPLE 4

This example demonstrates that the shared epitope is found in AD-modulating proteins, and that the shared epitope in these proteins can inhibit cAMP-mediated DNA repair.

The amino acid sequence of the shared epitope, QRRAA [Gln Arg Arg Ala Ala] [SEQ ID NO: 2], was subjected to a BLAST search against the SwissProt database (84,485 sequences). Only four non-MHC human proteins were found to contain that sequence. Strikingly, three of the four were nervous system proteins (APLP 1, lamininβ2 and ankyrin B). A homologous sequence was found around the variable position 158 of ApoE (FIG. 7). As shown in FIG. 7, amino acids 70–74 of HLA-DRβ*0401 and HLA-DRβ*0404 correspond to the shared epitope. Amino acids 70–74 of HLA-DRβ*0402 and HLA-DRβ*0403 encode sequences which do not correspond to the shared epitope or shared epitope motif. Amino acids 118–122 of human lamininβ2 also correspond to the shared epitope sequence, as do amino acids 387–391 of APLP1. Amino acids 121–125 of murine lamininβ2 are consistent with the shared epitope motif. Similarly, amino acids 156–160 of ApoEε4, ε3 and ε2 are consistent with the shared epitope motif (FIG. 7).

The QRRAA [Gln Arg Arg Ala Ala] [SEQ ID NO: 2] sequence in human laminin appears to be functional, as exposure of M1 cells to purified human and mouse laminin inhibited their inducible DNA repair activity. 2CA-induced DNA repair was determined in M1 cells preincubated overnight in tissue culture plates coated with either human laminin (H. Laminin), mouse laminin (M. Laminin), or human fibronectin (H. Fibronectin). Fibronectin, on the other hand, did not cause any inhibition (FIG. 8).

To directly examine the biological activity of the shared epitope, a QRRAA [Gln Arg Arg Ala Ala] pentapeptide [SEQ ID NO: 2] was synthesized and used in DNA repair assays. 2CA-induced DNA repair was determined in M1 cells preincubated overnight with 50 μg/ml of synthetic pentapeptides representing the shared epitope, or its single- or multiple-amino acid substitutions. As can be seen in FIG. 9, pre-incubation of M1 cells with the short peptide inhibited completely cAMP-dependent DNA repair induction. The homologous pentapeptide QKRAA [Gln Lys Arg Ala Ala] [SEQ ID NO: 1] had a similar effect.

To further determine the critical amino acids involved, a series of synthetic pentapeptides carrying single or multiple amino acid substitutions were tested. The sequences of the pentapeptides are shown in Table 4.

TABLE 4

| Synthetic Pentapeptides | |
|---|---|
| Pentapeptide Sequence | SEQ ID NO |
| QKRAA | SEQ ID NO: 1 |
| Gln Lys Arg Ala Ala | |
| QRRAA | SEQ ID NO: 2 |
| Gln Arg Arg Ala Ala | |
| QKRLA | SEQ ID NO: 11 |
| Gln Lys Arg Leu Ala | |
| QKRAE | SEQ ID NO: 14 |
| Gln Lys Arg Ala Glu | |
| QKCLA | SEQ ID NO: 12 |
| Gln Lys Cys Leu Ala | |
| QECLA | SEQ ID NO: 15 |
| Gln Glu Cys Leu Ala | |
| DKCLA | SEQ ID NO: 16 |
| Asp Lys Cys Leu Ala | |

As can be seen in FIG. 9, substitution of either glutamine 70 with aspartic acid, arginine/lysine 71 with glutamic acid, or alanine 74 with glutamic acid, abolished in all cases the inhibitory effect on cAMP-dependent signaling. On the other hand, substitution of arginine 72 to cysteine, or alanine 73 to leucine had no effect on the inhibitory effect of the peptide. It is therefore concluded that, consistent with the data shown in FIG. 1, residues Q70 [Gln70], R/K71 [Arg/Lys71] and A74 [Ala74] are critical amino acids, while R72 [Arg72] and A73 [Ala73] are not. These findings indicate that cAMP signal-inhibiting sequences possess the Q-(K/R)-X-X-A [Gln (Lys/Arg) Xaa Xaa Ala (wherein Xaa represents any amino acid)] [SEQ ID NO: 3] motif. That motif exists in RA shared epitope, as well as in APLP1, lamininβ2 and ApoE.

It is noteworthy that the ApoE2-derived peptide, QKCLA [Gln Lys Cys Leu Ala] [SEQ ID NO: 12], and the ApoE3/ApoE4-derived peptide, QKRLA [Gln Lys Arg Leu Ala] [SEQ ID NO: 11], were equally effective in suppressing cAMP signaling. However, only ApoE2 and ApoE3, but not ApoE4 are believed to have a neuroprotective effect in-vivo. It is hypothesized that the failure of the ApoE4 protein to trigger neuroprotective signaling in-vivo may be due to the C112R [Cys112Arg] substitution [the single substitution which truly distinguishes between the AD-enhancing (ApoE4 with R112) and AD-protecting (ApoE2 and ApoE3 with C112) alleles]. The 156–160 domain of ApoE4 may be inaccessible to interaction with its receptor due to conformational constraints imposed by the arginine residue at position 112. A positively charged residue at this position has been previously shown to affect the secondary structure and binding properties of ApoE [Weisgraber K H. *J Lipid Res* 31:1503–1511 (1990); LaDue M J et al. *J Neurosci Res* 49:1 9–18 (1997)].

EXAMPLE 5

In this example, results of experiments carried out to address the potential pathway by which the shared epitope motif may inhibit cAMP signaling are presented. The shared epitope motif may inhibit cAMP signaling through the NO pathway, although the precise mechanism underlying the invention is not essential to the practice of the invention, and any hypothesized mechanism is not intended to be in any way limiting.

As mentioned above, DNA repair signaling is mediated by the cAMP/PKA pathway and is inhibited by NO. Because NO has neuroprotective effects, and elevating NO levels has been identified as a desirable therapeutic objective in AD, the inventors studied the signaling events caused by shared epitope peptides.

A.) cAMP levels were assayed in M1 cells that were preincubated for 10 minutes with peptide-conjugated beads [Bead*0401, SEQ ID NO:6; Bead*0402, SEQ ID NO: 8], and intracellular cAMP level changes in response to stimulation with either 10 μM (FIG. 10A, top) or 100 μM (FIG. 10A, bottom) of 2CA were determined at different time points. cAMP levels were measured using a commercial enzyme immunoassay kit from Pharmacia. Results are expressed as fold increase of cAMP above baseline levels.

B.) PKA activity was determined in M1 cells preincubated with peptide-conjugated beads [Bead*0401, SEQ ID NO: 6; Bead*0402, SEQ ID NO: 8], at different time points following treatment with 10 μM 2CA as above.

C.) NO levels were determined as described above using a commercial kit (from Cayman) in M1 cells at different time points following exposure to peptide-conjugated Sepharose beads [Bead*0401, SEQ ID NO: 6; Bead*0402, SEQ ID NO: 8].

D.) cGMP levels in M1 cells were determined as described above using an enzyme immunoassay kit (Pharmacia) at different time points following exposure to 50 μg/ml of soluble 65–78*0401 [SEQ ID NO: 6] or 65–78*0402 [SEQ ID NO: 8] peptides.

As shown in FIG. 10, M1 cells incubated with peptides [SEQ ID NO: 6] which contain QKRAA [Gln Lys Arg Ala Ala] [SEQ ID NO:1] failed to increase cAMP levels or activate PKA following stimulation with 2CA, while cells incubated with a control peptide [SEQ ID NO: 8] mounted substantial response to the agonist (FIGS. 10A and B).

E.) M1 cells were preincubated overnight with 5 mM of the nitric oxide synthase (NOS) inhibitor, NG-methyl-L-arginine (L-NMA). At the end of incubation, cells were collected, washed and preincubated for 10 min with peptide-conjugated beads [Bead*0401, SEQ ID NO: 6; Bead*0402, SEQ ID NO: 8], before determining 2CA-inducible DNA repair activity.

F.) M1 cells were preincubated for 10 min with 1 μM of the protein kinase G (PKG) inhibitor, KT5823. At the end of incubation, cells were collected, washed and preincubated with either medium or 65–78*0401 [SEQ ID NO:6] peptide-conjugated beads. Cells were then collected, washed and subjected to 2CA-induced DNA repair assay.

As shown in FIG. 10(E), the inhibitory effect of the peptide [SEQ ID NO: 6] which contains QKRAA [Gln Lys Arg Ala Ala] [SEQ ID NO: 1] could be blocked by prior incubation of cells with a NOS inhibitor, $N^G$-methyl-L-arginine (L-NMA). Additionally, incubation of M1 cells with the shared epitope-containing peptide triggered increased cGMP levels in those cells (FIG. 10D). The inhibitory effect of shared epitope-containing peptides could be blocked by prior incubation of M1 cells with the PKG inhibitor, KT5823 (FIG. 10F).

Taken together, these data suggest that the mechanism by which shared epitope-containing peptides modulate cAMP-dependent signaling involve receptor-mediated activation of NOS with resultant increased levels of NO, which, in turn cause increased cGMP, culminating in PKG activation (FIG. 10).

EXAMPLE 6

In this example, results of experiments carried out to address the cAMP signaling effects of genetically engineered shared epitope-containing proteins are presented.

To further assess the ability of shared epitope-containing compounds to reverse cAMP signaling, and to assess the potential utility of delivery systems for such epitopes, a genetic approach was used. To that end, the shared epitope was inserted into a recombinant hepatitis B core (HBc) protein, which assembles a multimer of 180–240 subunit shell of approximately 30–34 nm in diameter with 90–120 spikes. That system has been previously shown to be an efficient, non-replicative and non-infective carrier of foreign epitopes [Reviewed in Pumpens P and Grens E. *FEBS Lett* 442:1–6 (1999)]. Accordingly, oligonucleotides corresponding to the region surrounding the third allelic hypervariable region (residue 65–79 of the DRβchain) of either the shared epitope-containing, DRB1*0401, or the shared epitope-negative, DRB1*0402, alleles were expressed at the tips of the HBc spikes (HBc*0401 (SEQ ID NO: 17) and HBc*0402 (SEQ ID NO: 18), respectively, FIG. 11A).

The appropriate coding sequence was inserted as a synthetic oligonucleotide between two unique restriction sites between amino acid residues 78 and 79 of the HBc molecule, as described in Borisova et al. [*Biol Chem* 380:

315–324 (1999)]. Due to the necessity of introducing neighboring restriction sites, the oligonucleotides coded for additional amino acid residues located amino- and carboxy-terminally to the shared epitope (His, and Val and Asp, respectively). The nucleotide sequence for amino acids 65–79 derived from DRB1*0401 along with the amino-terminal flanking His and the carboxy-terminal flanking Val and Asp is:

cac aag gac ctc ctg gag cag aag    [SEQ ID NO: 19]

cgg gcc gcg gtg gac acc tac tgc gta gat and the nucleotide sequence for amino acids 65–79 derived from DRB1*0402 along with the amino-terminal flanking His and carboxy-terminal flanking Val and Asp is:

cac aag gac atc ctg gaa gac gag    [SEQ ID NO: 20]

cgg gcc gcg gtg gac acc tac tgc gta gat.

M1 cells were preincubated overnight with 50 μg/ml of HBc*0401 or HBc*0402. At the end of incubation, cells were collected, washed and subjected to 2CA-induced DNA repair assay as above. As shown in FIG. 11B, shared epitope-expressing core particles, but not those expressing a non-shared epitope-containing sequence, effectively suppressed cAMP signaling. Thus, the shared epitope, when engineered into carrier proteins can specifically transduce a cAMP-inhibitory signal, similar to shared epitope-containing native proteins, or short synthetic peptides. This finding suggests that a gene transfer for targeted delivery of the shared epitope might prove useful in therapies.

EXAMPLE 7

This example presents the results of experiments carried out to address the neuroprotective effects of shared epitope-containing peptides.

In order to assess whether shared epitope-containing peptides exert a neuroprotective effect, preliminary experiments were carried out with the hybrid neuroblastoma-glioma NG108–15 cell line. Cells ($10^5$/ml) were first cultured overnight at near-confluence in 24-well plates in DMEM medium supplemented with 1% fetal calf serum (FCS). Under these conditions, NG108–15 cells show a flat, multipolar morphology and neurite formation. After 20 hours, cells were stressed acutely in serum-free medium (by aspiration of the medium and replacement with serum-free DMEM) with 50 μg/ml of peptides and evaluated morphologically at different time points thereafter. In cultures treated with the control peptide 65–78*0402 [SEQ ID NO: 8], adjacent cells showed a rounding effect and collapsed into aggregates (FIG. 12A). In cultures treated with the shared epitope-containing peptide 65–78*0401 [SEQ ID NO: 6], there was greater preservation of the multipolar flat cell morphology with neurites (FIG. 12B). Morphological differences between cultures treated with different peptides could be observed as early as 5–6 hrs after treatment. The photographs shown were taken at the 24 hr time point. In another experiment (FIG. 12C), NG108–15 cells were cultured at low cell density ($2\times10^4$/ml) in 1% FCS-containing DMEM medium overnight. The next day cells were subjected to acute stress in serum-free and low glucose (RPMI1640) medium (after aspiration of the 1% FCS DMEM) in the presence of 50 μg/ml of either 65–78*0401 [SEQ ID NO: 6] or 65–78*0402 [SEQ ID NO: 8] peptides. After 72 hours, cells were fixed with 1% formaldehyde and inspected microscopically. Mean±SEM was determined by averaging cell counts in eight randomly-selected microscopic fields in 200× magnification. Neurite-positive cells were defined as cells with one or more projections extending at least twice as long as the cell diameter. Cells cultured in the presence of shared epitope-containing peptide 65–78*0401 [SEQ ID NO: 6] showed a significantly higher survival rate (p<0.0005) and a higher percentage of neurite-positive cells (p<0.001), compared to cells cultured in the presence of the control peptide, 65–78*0402 [SEQ ID NO: 8] (FIG. 12C). The calculated number of neurite-positive cells was over 6-fold higher in shared epitope-containing peptide-cultured cells. When cultured in the presence of lysophosphatidic acid or high concentrations of serum, neuronal cells undergo neurite retraction (130). Treating NG108–15 cells with the shared epitope-containing, 65–78*0401 [SEQ ID NO: 6] peptide, but not with the control 65–78*0402 [SEQ ID NO: 8] peptide, inhibited the neurite retraction effect of 10% FCS (data not shown). Thus, it is concluded that shared epitope-containing peptides may exert neuroprotective effects.

The data presented here indicate that the RA shared epitope represents a sequence motif found in proteins capable of transmembrane activation of the NO/cGMP/PKG pathway. It is proposed that the shared epitope motif is playing a role in the neuroprotective effects of ApoE, APLP1 and laminin and could account for the negative association between AD and RA. Of course, understanding the mechanism underlying the invention is not required for the successful practice of the invention, and the invention is in no way limited to any particular mechanism.

EXAMPLE 8

This example outlines various animal models and assays that may be used to evaluate the biological activity of the compounds of the present invention in vivo.

A. Transgenic Mice Models

Transgenic (Tg) mice over expressing wild type or mutant APP manifest age-dependent neuropathology reminiscent of AD, including amyloid plaques, hyperphosphorylated tau, cognitive deficits and behavioral abnormalities. There are several such Tg lines, which differ in the type of mutant APP, the promoter used for targeted expression, the background strain of mice and the level of APP overexpression achieved. The resemblance to the human disease is substantial, though incomplete, since no neurofibrillary tangles or neuronal loss can be seen.

Double Tg mice expressing APP and mutant presenilin have been described. Those mice demonstrate AD-like neuropathology at an earlier age compared to most single Tg mice.

Other Tg models involve the ApoE4 or tau genes. Those models are characterized by psychometric impairment with axonopathy in the brain and spinal cord. Although hyperphosphorylated tau is present, neurofibrillary tangles are absent. Double Tg mice expressing tau and mutant APP show earlier and more severe neuropathology.

ApoE-deficient mice manifest mild cognitive impairment and tau hyperphosphorylation. Tg mice over expressing ApoE4 in neurons manifest a severe neuropathologic phenotype, which included motor problems, muscle wasting, hyperphosphorylated tau and early death. The pathology is evident as early as three months after birth.

B. Induced Models of AD-Like Pathology in Rodents.

Cholinotoxicity in rats is considered an acceptable model for Alzheimer's-associated dementia. The underlying rationale for studying this model is that an intact cholinergic system is required for normal brain functions. That system is defective in AD. To induce cholinotoxicity, male Wistar rats are injected intracerebrally with the cholinotoxin, ethylcholin aziridium (AF64A), which is a blocker of choline uptake. Short-term memory is significantly impaired in those animals.

Another model of induced dementia in rats involves induction of bilateral electrocortical lesions of nucleus basalis manocellularis. Those lesions produce deficiency in several behavioral AD-related tests, such as active avoidance, neophobia, aggression and depression.

Amyloid plaque deposition can be induced in mammals by infusing into the brain parenchyma an amyloid peptide at a basic pH as described in U.S. Pat. No. 6,172,277 to Tate et al., herein incorporated by reference.

C Aged Animals

AD-like neuropathology has been reported in aged dogs and monkeys. Old canines develop extensive β amyloid deposition within neurons and synapses, with formation of senile plaques. Neurofibrillary tangles, however, are not seen. The age-associated histopathology in canine is accompanied by cognitive decline. Aged rhesus monkeys show β amyloid deposition in senile plaques. Microinjection of fibrillar β amyloid into the aged- but not young-rhesus monkey cerebral cortex results in profound neuronal loss, tau phosphorylation and microglial proliferation.

D. Biological Tests In Vivo.

Tg mice and aged dogs and monkeys are treated with one of the compounds of the invention (e.g. shared epitope- or shared epitope motif-containing peptides, derivatives, analogues, mimetics, conjugates or antagonists) by any convenient route of administration (e.g. intravenously, subcutaneously, intraperitoneally or intramuscularly). Alternatively, the compounds are administered intranasally or as an inhaled aerosol. At different time points thereafter, animals are subjected to behavioral studies, which in mice include open field testing, beam task, string task, Y-maze, water maze, circular platform task, as well as passive and active avoidance. Aged dogs are evaluated for cognitive function and exploratory behavior. Monkeys are tested for memory tasks.

Histological parameters of neurodegeneration are determined in sacrificed mice and rats at different time points after treatment. Brain tissue is tested for glial fibrillary acidic protein, activated microglia, dystrophic neurites, amyloid plaques and detergent-insoluble and water soluble amyloid β protein. Brain sections and tissue extracts from different anatomical areas are used to determine the extent of ApoE expression and tau phosphorylation by immunohistochemistry and Western blotting, using specific monoclonal antibodies.

For cholinotoxin-induced cognitive impairments, male Wistar rats are injected intracerbroventricularly (ICV) with AF64A as described by Fisher et al. [*Neurosci Lett* 102: 325–331 (1989)]. Animals are left to recover for a week. Learning and memory tests are conducted using the swim maze test. Subgroups of animals are injected ICV daily with any of the compounds of the present invention (e.g. shared epitope- or shared epitope motif-containing peptides, analogues, derivatives, mimetics or antagonists), or with saline as a control. Learning and memory tests are repeated 7 and 14 days later.

E. Biological Tests In Vitro.

Survival of neurons is determined in vitro by culturing neuronal cells as described by Forsythe and Westbrook [*J Physiol* (Lond) 396:515–533 (1988)]. Alternatively, neuroblastoma cell lines are used. After established growth is observed, the cultures are given a change of medium and treated with different concentrations of the compounds of the invention (e.g. shared epitope- or shared epitope motif-containing peptides, derivatives, analogues, mimetics and antagonists). Neuronal survival is determined by microscopic determination of viable cell number per field. The extent of neurite formation in neuroblastoma cell lines is determined by counting the number of cells with neurites extending to a length greater than twice the cell diameter.

F. Models of RA-Like Pathology in Rodents.

Collagen-induced arthritis in mice, either with [Taneja V et al. *Arthritis Res.* 2, 205–207, (2000)] or without DRB1*0401 transgene [Holmdahl R. et al. *Ageing Res Rev.* 1, 135–147, (2002)] is considered to be a model for RA-associated arthropathy. Adjuvant arthritis in rats [Holoshitz J et al. *Science* 219, 56–58, (1983)], spontaneous arthritis in transgenic KRN mice [Kyburz D and Corr M et al. *Springer Semin Immunopathol*, 25: 79–90, (2003)] and the Zap70-mutated mouse, which display many of the characteristics of the human disease [Sakaguchi N et al. *Nature.* 426: 454–460, (2003)] are other models of RA in rats with lesions that may be RA-related.

EXAMPLE 9

In this example, the preparation of a peptide conjugate is described. The synthetic peptide $NH_2$-Q(K/R/H)XXA [Gln (Lys/Arg/His Xaa Xaa Ala] [SEQ ID NO: 21]can be prepared commercially (e.g. Multiple Peptide Systems, San Diego, Calif.). In a preferred embodiment, a cysteine is added (e.g. QRACA [Gln Arg Ala Cys Ala] [SEQ ID NO: 22], QKRAAC [Gln Lys Arg Ala Ala Cys] [SEQ ID NO: 23] or CQKRAA [Cys Gln Lys Arg Ala Ala] [SEQ ID NO: 24]) to facilitate conjugation to other proteins.

In order to prepare the carrier protein for conjugation (e.g. BSA), it is dissolved in buffer (e.g., 0.01 M $NaPO_4$, pH 7.0) to a final concentration of approximately 20 mg/ml. At the same time n-maleimidobenzoyl-N-hydroxysuccinimide ester ("MBS" available from Pierce) is dissolved in N,N-dimethyl formamide to a concentration of 5 mg/ml. The MBS solution, 0.51 ml, is added to 3.25 ml of the protein solution and incubated for 30 minutes at room temperature with stirring every 5 minutes. The MBS-activated protein is then purified by chromatography on a Bio-Gel P-10 column (Bio-Rad; 40 ml bed volume) equilibrated with 50 mM $NaPO_4$, pH 7.0 buffer. Peak fractions are pooled (6.0 ml).

The above-described cysteine-modified peptide (20 mg) is added to the activated protein mixture, stirred until the peptide is dissolved and incubated 3 hours at room temperature. Within 20 minutes, the reaction mixture becomes cloudy and precipitates form. After 3 hours, the reaction mixture is centrifuged at 10,000×g for 10 min and the supernatant analyzed for protein content. The conjugate precipitate is washed three times with PBS and stored at 4° C.

EXAMPLE 10

In this example, several peptides based on the shared epitope motif are contemplated.

The shared epitope motif, Q(K/R)XXA [Gln (Lys/Arg) Xaa Xaa Ala] [SEQ ID NO: 3], has two variable amino acid positions (Xaa, wherein Xaa represents any amino acid). Thus, a variety of peptide sequences are possible, based on variation at the variable positions. As noted above, a derivative of the shared epitope motif, in which histidine is substituted for the lysine or arginine is also contemplated (i.e. QHXXA [Gln His Xaa Xaa Ala] [SEQ ID NO: 4]). Thus, possible shared epitope motif-containing peptides and derivatives can be expressed by the following sequences: $QRX_1X_2A$ [Gln Arg $Xaa_1$ $Xaa_2$ Ala] [SEQ ID NO: 25], $QKX_1X_2A$ [Gln Lys $Xaa_1$ $Xaa_2$ Ala] [SEQ ID NO: 26] and $QHX_1X_2A$ [Gln His $Xaa_1$ $Xaa_2$ Ala] [SEQ ID NO: 27] in which $X_1$ is selected from the group of amino acids consisting of alanine, valine, leucine, isoleucine, serine, threonine and asparagine; and $X_2$ is selected from the group of amino acids consisting of alanine, valine, isoleucine, serine, threonine and asparagine.

EXAMPLE 11

In this example calreticulin is identified as a receptor that binds shared epitope-containing peptides. The shared epitope-binding receptor has been identified as calreticulin, using affinity chromatography followed by microsequencing. The specificity and the kinetics of the binding between shared epitope-expressing peptides and recombinant calreticulin were determined in-vitro by surface plasmon resonance analysis. The functional role of calreticulin was confirmed by successful inhibition of peptide-induced pro-oxidative signaling by pre-incubating cells with anti-calreticulin antibodies or transfecting them with calreticulin antisense oligonucleotides, as well as by studying shared epitope signaling in murine embryonic fibroblasts from homozygous calreticulin-deficient mice.

Total cellular protein extracts were loaded onto columns of Sepharose beads, conjugated with either shared epitope-containing peptide 65–78*0404 [SEQ ID NO: 28] or the control peptide 65–78*0402 [SEQ ID NO: 8]. Bound proteins were eluted at low pH. See, Auger I, Escola J M, Gorvel J P and Roudier J. While no protein binding was detected on the 65–79*0402 [SEQ ID NO: 7]-conjugated control column, 65–78*0404 [SEQ ID NO: 28]-conjugated column eluates gave ~20 distinct bands corresponded to known proteins. 11 sequenced bands matched intracellular proteins, and only two sequences matched previously identified cell surface proteins: heat shock protein 60 (HSP60) and calreticulin. Both calreticulin and HSP60 are chaperones, with strong tendency to form hetero-complexes.

To determine whether 65–78*0404 [SEQ ID NO: 28]-conjugated peptides bind these proteins directly, purified recombinant products were used. As can be seen in FIG. 13A, 65–78*040-affinity columns specifically bound recombinant human calreticulin (the amino acid sequence of this recombinantly produced protein is set out in FIG. 14 [SEQ ID NO: 29]), but not HSP60. These data confirm that cell surface calreticulin is binding shared epitope-containing peptides. That conclusion was supported in surface plasmon resonance experiments shown in FIG. 13B. Shared epitope-containing peptides, 65–79*0401-[SEQ ID NO: 5] and 65–79*0404-[SEQ ID NO: 10], as well as a control peptide 65–79*0402-[SEQ ID NO: 7] were immobilized on different channels in a Biacore® sensor chip CM5 and purified recombinant calreticulin was applied in the flow phase. As can be seen in FIG. 13B, shared epitope-containing 65–79*0401-[SEQ ID NO: 5] and 65–79*0404-[SEQ ID NO: 10] showed markedly higher calreticulin binding, compared to the control peptide, 65–79*0402-[SEQ ID NO: 7].

Finally, in order to determine whether these neuroprotective peptides transduce their signaling through calreticulin, two complementing protocols were executed: i) Inhibition of peptide-calreticulin interaction using anti-calreticulin antibodies, or ii) blocking calreticulin expression with antisense oligonucleotides (as shown in FIG. 13C and FIG. 13D).

Antisense Oligonucleotide Transfection

Caireticulin sense and antisense oligonucleotides were synthesized by Operon. The sequences of oligonucleotide were as follows:

```
Antisense,    5'-GGATAGCAGCATGGCGGGCCG-3';
              (SEQ ID NO:37);

Sense,        5'-CGGCCCGCCATGCTGCTATCC-3'.
              (SEQ ID NO:38).
```

M1 cells were cultured in 6-well plate to 60–70% confluency. M1 cells were treated by 0.2 µM antisense oligonucleotide for 24 to 48 hr, using Lipofectin as a carrier. Calreticulin expression levels were determined by Western-blot and flow cytometry, using anti-calreticulin antibodies. Polyclonal rabbit anti-human calreticulin antibodies were obtained from ABR, Golden, CO. As can be seen in FIG. 13C, calreticulin antisense (but not sense) oligonucleotides inhibited cell surface expression and blocked peptide-triggered signaling as shown in FIG. 13D. Similarly, as shown in FIG. 13D, anti-calreticulin antibodies specifically blocked the peptide effect. Therefore the shared epitope inhibitory effect on genoprotection is prevented by DKCLA, anti-calreticulin antibodies and anti-calreticulin antisense oligonucleotides, but not by control antibodies or calreticulin sense oligonucleotides. These data are support the conclusion that calreticulin is the cell surface receptor which mediates shared epitope-peptide signaling. Hence, the functional role of calreticulin was confirmed by successful inhibition of peptide-induced pro-oxidant signaling by pre-incubating cells with anti-calreticulin antibodies or transfecting them with calreticulin anti-sense oligonucleotide.

EXAMPLE 12

In this example, it is demonstrated that although peptide DKCLA [SEQ ID NO: 16] is biologically inactive, it binds with high affinity to calreticulin.

1. Purification of Calreticulin

The *E. coli* strain expressing GST fusion Calreticulin was kindly provided by Dr. Michalak [Baksh S et al. *Protein Expr Purif.*, 3, 322–331, (1992)]. GST-Calreticulin was purified according to the manual of GST Gene Fusion System from Pharmacia. Factor Xa was used to liberate GST from calreticulin. In an additional step the column was treated with mono-Q to achieve >90% purity of calreticulin (MW=60 kD).

2. Surface Plasmon Resonance

Prior to use, biosensor chips CM5 were docked into a Biacore® 2000 and preconditioned in water at 100 µl/min by applying two consecutive 20-µl pulses of 50 mM NaOH, then 10 mM HCl, and finally 0.1% SDS. Calreticulin was immobilized on CM5 surface by standard primary amine coupling [Lofas S et al. *Biosensors & Bioelectronics*, 10:

813–822, (1995), Johnsson B et al. *J Mol Recognit.*, 8: 125–131, (1995), Karlsson R et al. *J. Immunol. Methods*, 200:121–133. (1997)]. Immobilizations were conducted at 25° C. in HBS-EP (10 mM HEPES, pH7.4, 150 mM NaCl, 1 mM EDTA, 0.005% Surfactant P-20), with a flow of 10 µl/min. The CM5 surface was activated by 7 min injection of 200 mM EDC/50 mM NHS to prepare a high-capacity surface, with manual injection of 100 µg/ml calreticulin until 5500 RU level was approached. Then 100 µl of 1M ethanolamine was used to block remaining activated group.

Calreticulin and peptide binding were performed at 25° C. in binding buffer (10 mM HEPES, pH8.0, 50 mM KCl, 0.5 mM $CaCl_2$, 1% Triton-X100), with a flow rate of 10 µl/min. Peptides in the analyte ranged in concentration from 25–180 µM. Binding assays were repeated at least 3 times. Kinetic analysis was performed using Kinetic separate $k_a/k_d$ fitting in BIA evaluation 3.0 software.

Analysis of pentapeptide signaling activity revealed that a consensus motif of Q-(K/R)-X-X-A is necessary and sufficient for shared epitope pro-oxidative activity. As shown in FIG. 9, pentapeptides expressing that motif (i. e., peptides # 1, 2, 3 and 5) efficiently inhibited the genoprotective pathway, while peptides with A74E (FIG. 15 peptide #4), R71E (FIG. 15 peptide #6) or Q70D (FIG. 15 peptide #7) substitutions failed to do so. Shared epitope-expressing peptides potently bind to, and trigger, signaling through calreticulin. Accordingly, the ability to activate the pro-oxidative pathway correlates with calreticulin binding. However, when calreticulin binding activities of the panel of pentapeptides were determined, one conspicuous exception was discovered, that is DKCLA FIG. 15 peptide #7 (Q70D). Although biologically inactive, DKCLA was found to bind very strongly to calreticulin (FIG. 15). In control experiments under identical conditions, the pentapeptide QKRAE did not bind to calreticulin, did not inhibit 65–79*0401 binding to calreticulin in a Biacore assay, and did not inhibit 65–79*0401-triggered NO production.

EXAMPLE 13

In this example the shared epitope antagonist-containing peptide DKCLA [SEQ ID NO: 16] is shown to compete with shared epitope-expressing peptides for the same binding site on calreticulin (Crt).

Figure 16A:
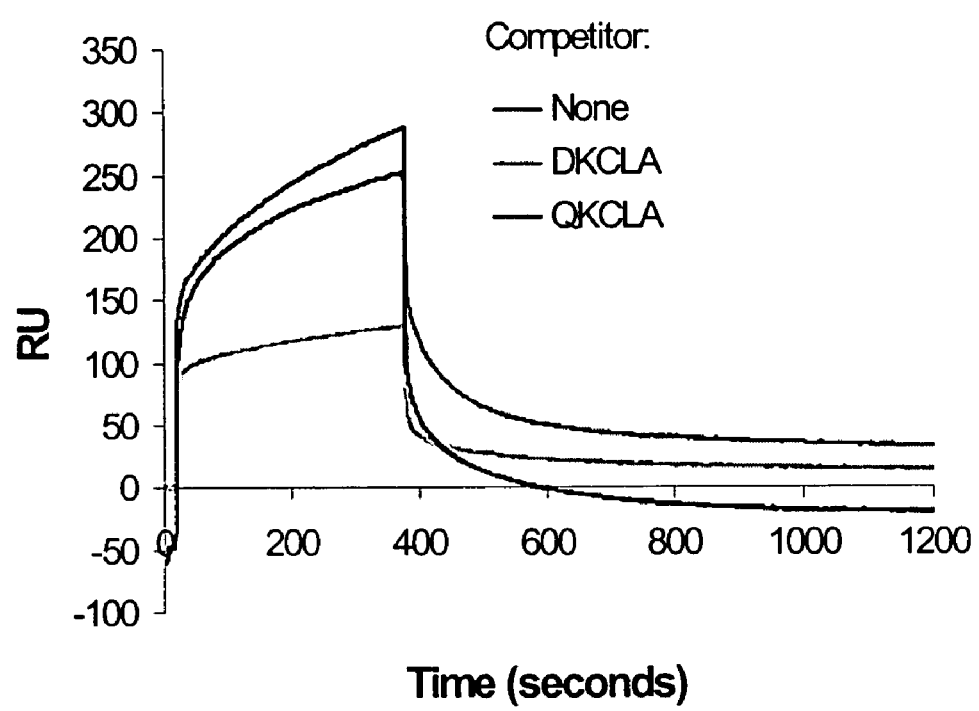
Figure 16B:
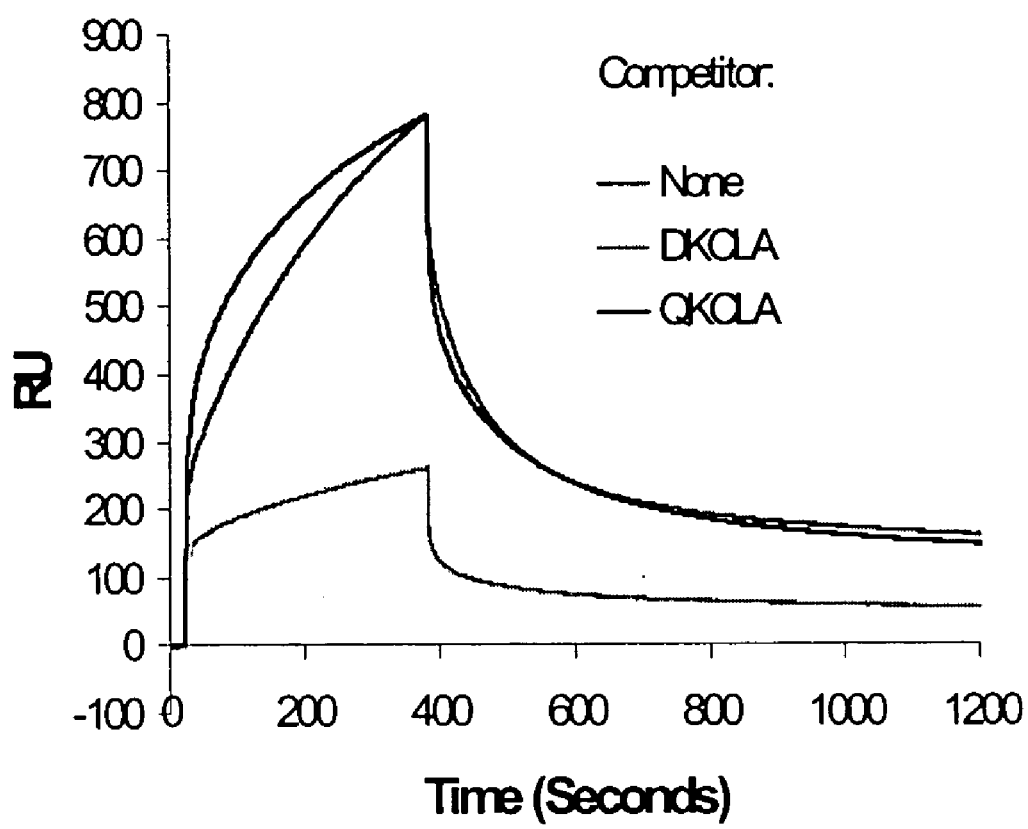
Figure 16C:
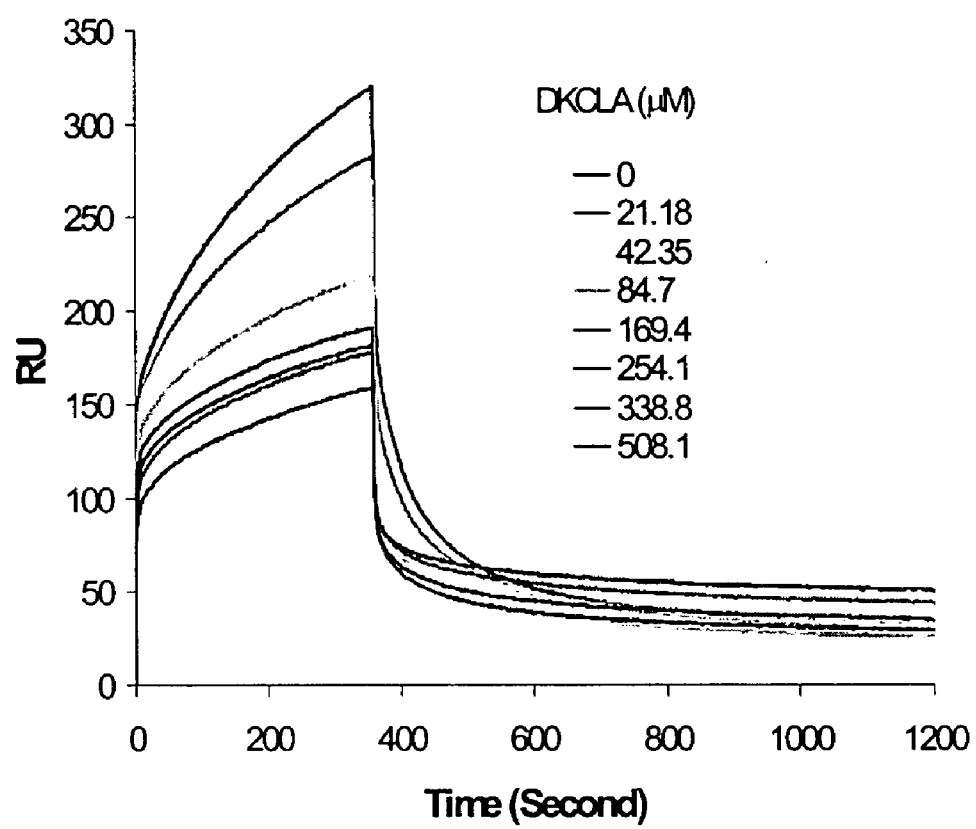
Figure 16D:
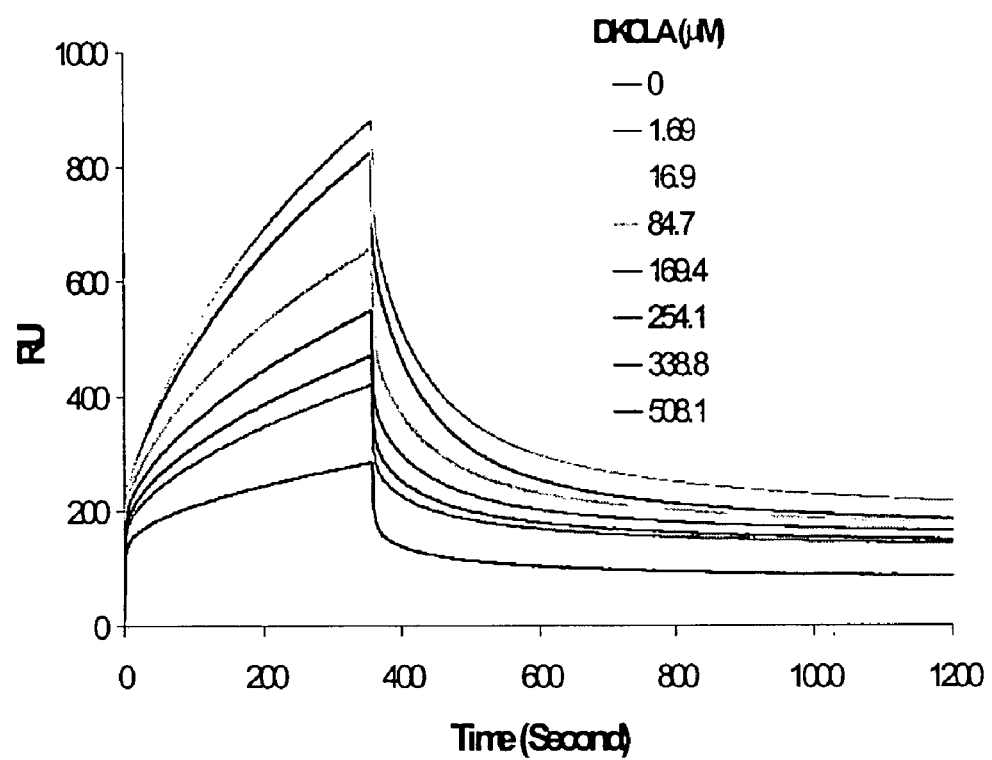

In order to determine whether DKCLA [SEQ ID NO: 16] and shared epitope-expressing peptides compete for the same binding site on calreticulin, competitive binding studies were performed in which the calreticulin binding activity of 14-mer shared epitope-expressing peptides was determined in the presence or absence of different pentapeptides. As can be seen in FIG. 16A and FIG. 16B, DKCLA [SEQ ID NO: 16] effectively and specifically blocked binding of 14-mer peptides corresponding to the 65–78 region of DRB1*0401 (65–78*0401, FIG. 3A) and DRB1*0404 (65–78*0404, FIG. 3B). Dose response analysis of DKCLA [SEQ ID NO: 16] inhibitory activity (FIG. 16C and FIG. 16D) revealed $IC_{50}$ values at the low-uM range. Thus, a Q70D substitution produces a shared epitope-antagonistic effect.

EXAMPLE 14

In this example, the shared epitope antagonsist peptide DKCLA [SEQ ID NO: 16] is shown to block NO induction by shared epitope-expressing peptide 65–79*401 in cells, demonstrating that shared epitope antagonist-containg peptides have inhibitory effects on shared epitope-triggered pro-oxidative signalling.

DKCLA [SEQ ID NO: 16] binds to calreticulin, and inhibits binding of shared epitope-expressing peptides which trigger pro-oxidative signaling (FIG. 9). In follow up experiments the functional activity of DKCLA [SEQ ID NO: 16] was determined by measuring its effect on NO production by shared epitope-expressing peptides (i.e. 65–79*0401) and a control peptide, 65–79*0402. Human fibroblastoid M1 cells were pre-incubated overnight with or without 50 υg/ml of DKCLA. Subsequently culture medium was changed to NO assay buffer (20 mM Tris, pH7.6, 100 mM NaCl, 0.1 mM EDTA), and cells were stimulated for 1–30 min with Sepharose bead-bound peptide 65–79*0401 or control peptide 65–79*0402. At different time points, cultures were collected and NO levels were measured. Briefly, supernatants were collected and spun down to remove cell debris. Nitrate in the supernatant were first transformed to nitrite by incubation with nitrate reductase for 60 min in room temperature. Then, DAN was added to yield fluorescent 2,3-naphthotriazole. Fluorescence was measured with a Perkin-Elmer Fusion™ Universal Microplate Analyzer, using a wavelength excitation of 375 nm and an emission wavelength of 415 nm.

1. Cells and Culture Conditions

Human fibroblastoid M1 were grown in Dulbecco's modified Eagle's medium (DMEM) containing 10% fetal bovine serum (FBS), penicillin/streptomycin, and 10 mM HEPES buffer solution.

2. Peptide Synthesis and Purification

Peptides were synthesized at the University of Michigan Protein Structure Facility on the Rainin PTI Synphony automated peptide synthesizer. Each residue was coupled twice with 200 mM HOBt+HBTU and 400 mM N-Methylmorpholine for 60 min, and capped with 50% acetic anhydride in DMF. The resins used were Fmoc-PAL-PEG resins from Applied Biosystems. Peptides were purified >90% by HPLC.

3. Bead Conjugation Protocol

Cyanogen bromide-activated Sepharose 4B was washed with 1 mM HCl and incubated with peptides in 0.1 M $NaHCO_3$ and 0.5 M NaCl (pH 8) buffer overnight at 4° C. For each peptide, 5 mg was used per milliliter of Sepharose 4B. Free Sepharose groups were blocked with 0.2 M glycine (pH 8) for 2 hours at room temperature. Columns were washed at 4° C. with the following buffers: 0.1 M.$NaHCO_3$, 0.5 M NaCl (pH 8) buffer; then 0.5 M $CH_3COONa$ (pH 4) buffer; and finally PBS at pH 7.5.

4. Assay of Nitrate and Nitrite

The nitrite and nitrate assay was a modified method from fluorometric determination of nitrite [Thomas Pet al. *Anal. Biochem.*, 214:11–16, (1993), Miles AM et al. *Methods* 7: 40–47, (1995)]. Cell culture medium was changed to NO assay buffer (20mM Tris, pH7.6, 100 mM NaCl, 0.1 mM EDTA) and was treated by bead bound peptides. After treatment, supernatant was spun down to remove cell debris. Nitrate in the supernatant was first transformed to nitrite by incubation with Nitrate Reductase for 60min in room temperature. Then 2,3-diaminonaphthalene (DAN) was added to yield fluorescent 2,3-naphthotriazole. Fluorescence was measured by a FUSION™ Universal Microplate Analyzer with excitation at 375 nM and emission at 415 nM.

As can be seen in FIG. 17, DKCLA [SEQ ID NO: 16] blocked NO induction by shared epitope-expressing peptide 65–79*0401. There was no measureable effect of DKCLA [SEQ ID NO: 16] on baseline NO levels, and no impact on the control peptide 65–79*0402 could be detected. Dose-response analyses estimate the IC50 of DKCLA [SEQ ID NO: 16] at ~35×10$^{-6}$ M.

REFERANCES

Aho K, Koskenvuo M, Tuominen J, Kaprio J. Occurrence of rheumatoid arthritis in a nationwide series of twins. *J Rheumatol* 13: 899–902, 1986.

Allen M. Miles, Yan Chen, Michael W. Owens, and Matthew B Grisham. Fluorometric Determination of Nitric Oxide. *Methods,* 7, 40–47, 1995.

Auger I, Escola J M, Gorvel J P and Roudier J. HLA-DR4 and HLA-DR10 motifs that carry susceptibility to rheumatoid arthritis bind 70-kD heat shock proteins. *Nature Med* 2: 306–310, 1996.

Baksh S, Bums K, Busaa J, and Michalak M. Expression and purification of recombinant and native calreticulin. *Protein Expr Purif.,* 3, 322–331, 1992.

Bashir S, Harris G, Denman M A, Blake D R and Winyard P G. Oxidative DNA damage and cellular sensitivity to oxidative stress in human autoimmune diseases. *Ann Rheum Dis* 52:659–666, 1993.

Basu S, Binder R J, Ramalingam T and Seivastava P. CD91 is a common receptor for heat shock proteins gp96, hsp70 and calreticulin. *Immunity* 14: 303–313, 2001.

Bhayani H R and Hedrick S M. The role of polymorphic amino acids of the MHC molecule in the selection of the T cell repertoire. *J Immunol* 146: 1093–1098, 1991.

Brown K A. The polymorphonuclear cell in rheumatoid arthritis. *Br J Rheumatol* 27: 150–155, 1988.

Cannons J L, Karsh J, Bimboim C and Goldstein R. HPRT mutant T cells in the peripheral blood and synovial tissue of patients with rheumatoid arthritis. *Arthritis Rheum* 41: 1772–1782, 1998.

Cava A L et al. Genetic bias in immune responses to a cassette shared by different microorganisms in patients with rheumatoid arthritis. *J Clin Invest* 100: 658–663, 1997.

Cemerski S, Cantagrel A, Van Meerwijk J P and Romagnoli P. Reactive oxygen species differentially affect T cell receptor-signaling pathways. *J Biol Chem* 277: 19585–19593, 2002.

Cemerski S, van Meerwijk J P, Romagnoli P. Oxidative-stress-induced T lymphocyte hyporesponsiveness is caused by structural modification rather than proteasomal degradation of crucial TCR signaling molecules. *Eur J Immunol* 33: 2178–2185, 2003.

Chemelli R M et al. Narcolepsy in orexin knockout mice: Molecular genetics of sleep regulation. *Cell* 98: 437–451, 1999.

Colaco C B, Harris G, Lawley P D, Lylyard P M and Roitt I M. Deficient repair of O$_6$-methylguanine in lymphocytes from rheumatoid arthritis families may be an acquired defect. *Clin Exp Immunol* 72:15–19, 1988.

Coppolino M, Leung-Hagesteijn C, Dedhar S and Wilkins J. Inducible interaction of integrin 2 1 with calreticulin. Depaendence on the activation state of the integrin. *J Biol Chem* 270: 23132–23138, 1995.

de Vries N, Tijssen H, van Riel P. L. C. M., van de Putte L. B. A. Reshaping the Shared Epitope Hypothesis HLA-Associated Risk for Rheumatoid Arthritis Is Encoded by Amino Acid Substitutions at Positions 67–74 of the HLA-DRB1 Molecule. *Arthritis Rheum* 46: 921–928, 2002.

Doherty D G et al. Allelic variation in the HLA class II genes and proteins in patients with autoimmune hepatitis. *Hepatology* 19: 609–615, 1994.

Dorak M T, Machulla H K, Hentschel M, Mills K I, Langner J and Burnett A K. Influence of the major histocompatibility complex on age at onset of chronic lymphoid leukemia. *Int J Cancer* 65: 134–139, 1996.

Eggleton P and Llewllyn D H. Pathophysiological roles of calreticulin in autoimmune disease. *Scand. J. Immunol* 49: 466–473, 1999.

Fraser S A, Karimi R, Michalak M and Hudig D. Perforin lytic activity is controlled by calreticulin. *J Immunol* 164: 4150–4155, 2000.

Grant D D, Goldstein R, Karsh J and Bimboim H C. Nitric oxide donors induce large-scale deletion mutations in human lymphoblastoid cells: implications for mutations in T-lymphocytes from arthritis patients. *Environ Mol Mutagen* 38: 261–267, 2001.

Gregersen P K, Silver J and Winchester R J. The shared epitope hypothesis: An approach to understanding the molecular genetics of susceptibility to rheumatoid arthritis. *Arthritis Rhem* 30: 1205–1213, 1987.

Hajeer A H, Worthington J, Silman A J and Ollier WER. Association of tumor necrosis factor microsatellite polymorphism with HLA-DRB1*04-bearing haplotypes in rheumatoid arthritis patients. *Arthritis Rheum* 39: 1109–1114, 1996.

Harris G et al. Radiosensitivity of peripheral blood lymphocytes in autoimmune disease. *Int J Radiat Biol Relat Stud Phys Chem Med* 47:689–699, 1985.

Haworth S, Ridgeway J, Stewart I, Pepper L and Ollier W. Polymyalgia rheumatica is associated with both HLA-DRB1*0401 and DRB1*0404. *Br J Rheumatol* 35: 632–635, 1996.

Henson P M, Bratton D L and Fadok V. The phosphatidylserine receptor: a crucial molecular switch? *Nat Rev Mol Cell Biol* 2: 627–633, 2001.

Holmdahl R, Bockermann R, Backlund J and Yamada H. The molecular pathogenesis of collagen-induced arthritis in mice—a model for rheumatoid arthritis. *Ageing Res Rev.* 1, 135–147, 2002.

Holoshitz J, Naparstek Y, Ben-Nun A and Cohen I R. Lines of T lymphocytes induce or vaccinate against autoimmune arthritis. *Science* 219, 56–58, 1983.

Holoshitz J and Ling S. Methods and compositions for the treatment of diseases associated with signal transduction aberrations. US Patent Pending. Publication Number: US 2003/0096748 A1. May 22, 2003.

Jikimoto T, Nishikubo Y, Koshiba M et al. Thioredoxine as a biomarker for oxidative stress in patients with rheumatoid arthritis. *Mol Immunol* 38: 765–772, 2001.

Johnsson B, Löfås S, Lindquist G, Edström A, Hillgren R M, Hansson A. Comparison of methods for immobilization to carboxymethyl dextran sensor surfaces by analysis of the specific activity of monoclonal antibodies. *J Mol Recognit.,* 8, 125–131, 1995.

Johnson S, Michalak M Opas M and Eggleton P. The ins and outs of calreticulin: from the ER lumen to the extracellular space. *Trends Cell Biol* 11: 122–129, 2001.

Karlsson R and Fält A. Experimental design for kinetic analysis of protein-protein interactions with surface plasmon resonance biosensors. *J. Immunol. Methods,* 200, 121–133. 1997.

Kuwabara K Pinsky D J Schmidt A M, et al. Calreticulin, an antithrombotic agent which binds to vitamin K-dependent coagulation factors, stimulates endothelial nitric oxide production and limits thrombosis in canine coronary arteries. *J Biol Chem* 270: 8179–8187, 1995.

Kyburz D and Corr M. The KRN mouse model of inflammatory arthritis. *Springer Semin Immunopathol*, 25, 79–90, 2003.

Lee S-H, Chang D K, Goel A, Boland C R, Bugbee W, Boyle D L and Firestein G S. Microsatellite instability and suppressed DNA repair enzyme expression in rheumatoid arthritis. *J Immunol* 170: 2214–2220, 2003.

Löfås S, Johnsson B, Edström A, Hansson A, Lindquist G, Hillgren R M and Stigh L. Methods for site controlled coupling to carboxymethyldextran surfaces in surface plasmon resonance sensors. *Biosensors & Bioelectronics*, 10, 813–822, 1995.

Lysiak J J, Hussaini I M, Webb D J, Glass W F, Allieta M and Gonias S L. 2-macroglobulin functions as a cytokine carrier to induce nitric oxide synthesis and cause nitric oxide-dependent cytotoxicity in the RAW 264.7 macrophage cell line. *J Biol Chem* 270: 21919–21927, 1995.

Mattey D L, Dawes P T, Gonzalez-Gay M A, Garcia-Porrua C, Thomson W, Hajeer A H, Ollier W E. HLA-DRB1 alleles encoding an aspartic acid at position 70 protect against development of rheumatoid arthritis. *J Rheumatol* 28: 232–239, 2001.

Maurice M M, Nakamura H, Van der Vroot E A M, Van Vliet A I, Staal F J T, Tak P P, Breedveld F C and Veweij C L. Evidence for the role of an altered redox state in hyporesponsiveness of synovial T cells in rheumatoid arthritis. *J Immunol* 158: 1458–1465, 1997.

Max H, Halder T, Kalbus M, Gnau V, Jung G and Kalbacher H. A 16mer peptide of the human autoantigen calreticulin is a most prominent HLA-DR4Dw4-associated self-peptide. *Hum Immunol* 41: 39–45, 1994.

McCarthy P J, Sweetman S F, McKenna P G and McKelvey-Martin V J. Evaluation of manual and image analysis quantification of DNA damage in the alkaline comet assay. *Mutagenesis* 12: 209–214, 1997.

McCurdy D, Tai L Q, Frias S, and Wang Z. Delayed repair of DNA damage by ionizing radiation in cells from patients with juvenile systemic lupus erythematosus and rheumatoid arthritis. *Radiat Res* 147:48–54, 1997.

Migita K, Yamasaki S, Kita M, Ida H, Shibatomi K, Kawakami A, Aoyagi T and Eguchi K. Nitric oxide protects cultured rheumatoid synovial cells from Fas-induced apoptosis by inhibiting caspase-3. *Immunology* 103: 362–367, 2001.

Mignot E. Genetic and familial aspects of narcolepsy. *Neurology* 50: S16-S22, 1998 Lin L, et al. The sleep disorder canine narcolepsy is caused by a mutation in the hypocretin (orexin) receptor 2 gene. *Cell* 98: 365–376, 1999.

Miles A M, Chen Y, Owens M W, and Grisham M B. Fluorometric determination of nitric oxide. *Methods* 7: 40–47, 1995.

Misko T P, Schilling R J, Salvemini D, Moore W M, and Currie M G. A fluorometric assay for the measurement of nitrite in biological samples. *Anal Biochem* 214: 11–16, 1993.

Nepom G T, Byers P, Seyfried C, Healy L A, Wiske K R, Stage D and Nepom B S. HLA genes associated with rheumatoid arthritis: Identification of susceptibility alleles using specific oligonucleotide probes. *Arthritis Rheum* 32: 15–21, 1989.

Patel J M, Li Y D, Zhang J, Gelband C H, Razida M K and Block E R. Increased expression of calreticulin is linked to ANG IV-mediated of lung endothelial NOS. *Am J Physiol* 277: L794–801, 1999.

Pike S E et al. Calreticulin and calreticulin fragments are endothelial cell inhibitors that suppress tumor growth. *Blood* 94: 2461–2468, 1999.

Rall L C, Roubenoff R, Meydani S N, Han S N, Meydani M. Urinary 8-hydroxy-2'-deoxyguanosine (8-OHdG) as a marker of oxidative stress in rheumatoid arthritis and aging: effect of progressive resistance training. *J Nutr Biochem* 11: 581–584, 2000.

Sánchez D, Tu ková L, Sêbo P, Michalak M, Whelan A, Šterzl I, Jelínková L, Havrdová E, Imramovská M, Bene š Z, Krupi ková S and Tlaskalová-Hogenová H. Occurrence of IgA and IgG autoantibodies to calreticulin in coeliac disease and various autoimmune diseases. *J Autoimmunity* 15: 441–449, 2000.

Sakaguchi N, Takahashi T, Hata H, Nomura T, Tagami T, Yamazaki S, Sakihama T, Matsutani T, Negishi I, Nakatsuru S and Sakaguchi S. Altered thymic T-cell selection due to a mutation of the ZAP-70 gene causes autoimmune arthritis in mice. *Nature*. 426, 454–460, 2003.

Seki S S, Sugimura K, Ota M et al. Stratification analysis of MICA triplet repeat polymorphism and HLA antigens associated with ulcerative colitis in Japanese. *Tissue Antigens,* 58: 71–76, 2001.

Seldin M F, Amos C I, Ward R and Gregersen P K. The genetics revolution and the assault on rheumatoid arthritis. *Artritis Rheum* 42:1071–1079, 1999.

Siegel J M. Narcolepsy: A key role for hypocretins (orexins). *Cell* 98: 409–412, 1999.

Sontheimer R D, Lieu T S and Capra J D. Calreticulin: the diverse functional repertoire of a new human autoantigen. *Immunologist* 1: 155, 1993.

Strettell M D, Donaldson P T, Thompson L J, Santrach P J, Moore S B, Czaja A J and Williams R. Allelic basis for HLA-encoded susceptibility to type 1 autoimmune hepatitis. *Gastroenterology* 112: 2028–2035, 1997.

Tait B D, Drummond B P, Varney M D and Harrison L C. HLA-DRB1*0401 is associated with susceptibility to insulin-dependent diabetes mellitus independently of the DQB1 locus. *Eur J Immunogenet* 22: 289–297, 1995.

Taneja V and David C S. Association of MHC and rheumatoid arthritis. Regulatory role of HLA class II molecules in animal models of RA: studies on transgenic/knockout mice. *Arthritis Res.* 2, 205–207, 2000.

Thomas P. Misko, Roger J. Schilling, Daniela Salvemini, William M. Moore, and Mark G. Currie. A Fluorometric Assay for the Measurement of Nitrite in Biological Samples. *Anal. Biochem.,* 214, 11–16, 1993.

Ueki Y, Miyake S, Tominaga Y and Eguchi K. Increased nitric oxide levels in patients with rheumatoid arthritis. *J Rheumatol* 23: 230–236, 1996.

Verreck F A, Elfrink D, Vermeulen C J, Amos R, Breedveld F, de Vries R R P and Konig F. DR4Dw4/DR53 molecules contain a peptide from the autoantigen calreticulin. *Tissue Antigen* 45: 270–275, 1995.

Weyand C M, Hunder N N, Hicok K C, Hunder G G and Goronzy J J. HLA-DRB1 alleles in polymyalgia rheumatica, giant cell arteritis, and rheumatoid arthritis. *Arthritis Rheum* 37:514–520, 1994.

Wu Y, Zheng J, Linden J and Holoshitz J. Genoprotective pathways: I. Extracellular signaling through Gs protein-coupled adenosine receptors prevents oxidative DNA damage. *Mut Res* 546: 93–102, 2004.

Wucherpfenning K W and Stromiger J L. Selective binding of self peptides to disease-associated major histocompatibility complex (MHC) molecules: A mechanism for MHC-linked susceptibilty to human autoimmune diseases. *J Exp Med* 181: 1597–1601, 1995.

Wucherpfennig K W, Yu B, Bhol K, Monos D S, Argyris E, Karr R W, Ahmed A R and Strominger J L. Structural basis for major histocompatibility complex (MHC)-linked susceptibility to autoimmunity: Charged residues of a single MHC binding pocket confer selective presentation of self-peptides in pemphigus vulgaris. *Proc Natl Acad Sci(USA)* 92:11935–11939, 1995.

Yamanishi Y, Boyle D L, Rosengren S, Green D R, Zvaifler N J and Firestein G S. Regional analysis of p53 mutations in rheumatoid arthritis synovium. *Proc Natl Acad Sci (USA)* 99: 10025–10030, 2002.

Zamani M and Cassiman J J. Reevaluation of the importance of polymorphic HLA class II alleles and amino acids in the susceptibility of individuals of different populations to type I diabetes. *Am J Med genet* 76: 183–194, 1998.

Having fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

The invention claimed is:

1. A method, comprising:
   a) providing;
      i) a subject with one or more signs or symptoms of rheumatoid arthritis; and
      ii) a preparation comprising a synthetic shared epitope peptide, said peptide consisting of the sequence DKCLA (Asp Lys Cys Leu Ala) (SEQ ID NO: 16); and
   b) administering said preparation to said subject under conditions such that said one or more signs or symptoms are improved.

2. The method of claim 1, wherein said shared epitope peptide is conjugated to at feast one lipophilic moiety.

3. The method of claim 1, wherein said shared epitope peptide is conjugated to at least one carrier molecule.

4. The method of claim 1, wherein said preparation comprises an aqueous medium.

5. The method of claim 1, wherein said preparation comprises at least one compound selected from the group comprising a buffer, a preservative and a salt.

6. The method of claim 1, wherein said preparation comprises a local anesthetic.

7. The method of claim 1, wherein said preparation comprises at least one compound selected from the group consisting of a corticosteroid, a non-steroidal anti-inflammatory compound, an analgesic, gold, penicillamine, an antimalarial compound, sulfasazine, methotrexate, azathioprine, and cyclophosphamide.

* * * * *